US007932389B2

(12) United States Patent
Swinnen et al.

(10) Patent No.: US 7,932,389 B2
(45) Date of Patent: Apr. 26, 2011

(54) OCTAHYDROPYRROLO[2,3C]PYRIDINE DERIVATIVES AND PHARMACEUTICAL USE THEREOF

(75) Inventors: Dominique Swinnen, Beaumont (FR); Agnes Bombrun, Chambesy (CH)

(73) Assignee: Merck Serono S.A., Vaud (CH)

( * ) Notice: Subject to any disclaimer, the term of this patent is extended or adjusted under 35 U.S.C. 154(b) by 701 days.

(21) Appl. No.: 11/658,084

(22) PCT Filed: Jul. 20, 2005

(86) PCT No.: PCT/EP2005/053501
§ 371 (c)(1),
(2), (4) Date: Jan. 22, 2007

(87) PCT Pub. No.: WO2006/008303
PCT Pub. Date: Jan. 26, 2006

(65) Prior Publication Data
US 2008/0146806 A1 Jun. 19, 2008

Related U.S. Application Data

(60) Provisional application No. 60/589,621, filed on Jul. 21, 2004.

(30) Foreign Application Priority Data

Jul. 21, 2004 (EP) ..................................... 04103483

(51) Int. Cl.
*C07D 471/02* (2006.01)
(52) U.S. Cl. ...................................................... 546/113
(58) Field of Classification Search .................. 546/113; 514/300
See application file for complete search history.

(56) References Cited

FOREIGN PATENT DOCUMENTS

| WO | 00 44730 | 8/2000 |
|----|----------|--------|
| WO | 01 83461 | 8/2001 |
| WO | 02 070521 | 9/2002 |
| WO | 03 016248 | 2/2003 |

OTHER PUBLICATIONS

Elizabeth Ambrose Amin, et al., "Three-Dimensional Quantitative Structure-Activity Relationship (3D-QSAR) Models for a Novel Class of Piperazine-Based Stromelysin-1 (MMP-3) Inhibitors: Applying a "Divide and Conquer" Strategy", Journal of Medicinal Chemistry, vol. 44, No. 23, XP 002309081, pp. 3849-3855, 2001.
M. G. Belvisi, et al., "The Role of Matrix Metalloproteinases (MMPs) in the Pathophysiology of Chronic Obstructive Pulmonary Disease (COPD): A Therapeutic role for inhibitors of MMPs?", Inflammation Research, vol. 52, pp. 95-100, 2003.
O. Bulbena, et al., "Cytoprotective Activity in the Gastric Mucosa of Rats Exposed to Carbon Tetrachloride-Induced Liver Injury", Inflammation, vol. 21, No. 5, pp. 475-488, 1997.
Ian M Clark, et al., "Metalloproteinases: Their Role in Arthritis and Potential as Therapeutic Targets", Expert Opinion Therapeutic Patents, vol. 7, No. 1, pp. 19-34, 2003.

Terence M Doherty, et al., "Therapeutic Developments in Matrix Metalloproteinase Inhibition", Expert Opinion Therapeutic Patents, vol. 12, No. 5, pp. 665-707, 2002.
Barbara Fingleton, "Matrix Metalloproteinase Inhibitors for Cancer Therapy: The Current Situation and Future Prospects", Expert Opinion Therapeutic Patents, vol. 7, No. 3, pp. 385-397, 2003.
Michael H. Fisher, et al., "A Convenient Synthesis of 6-Azaindole", J. Heterocycl. Chem., vol, 6, pp. 775-776, 1969.
Zorina S. Galis, et al., "Matrix Metalloproteinases in Vascular Remodeling and Atherogenesis the Good, the Bad, and the Ugly", Circulation Research, vol. 90, pp. 251-262, 2002.
Y Henrotin, et al., "The Inhibition of Metalloproteinases to Treat Osteoarthritis: Reality and New Perspectives", Expert Opinion Therapeutic Patents, vol. 12, No. 1, pp. 29-43, 2002.
Nigel M. Hooper, et al., "Membrane Protein Secretases", Biochem. J., vol. 321, pp. 265-279, 1997.
Solveig Horstmann, et al.,"Profiles of Matrix Metalloproteinases, Their Inhibitors, and Laminin in Stroke Patients. Influence of Different Therapies", Stroke, vol. 34, No. 9, pp. 2165-2170, 2003.
Ingman T., et al., "Matrix Metalloproteinases and Their Inhibitors in Gingival Crevicular Fluid and Saliva of Periodontitis Patients", Journal of Clinical Periodontology, vol. 23, pp. 1127-1132, 1996.
Ganesh Krishna, et al., "New Therapies of Chronic Obstructive Pulmonary Disease", Expert Opinion Investig. Drugs, vol. 13, No. 3, pp. 255-267, 2004.
David Leppert, et al., "Matrix Metalloproteinases: Multifunctional Effectors of Inflammation in Multiple Sclerosis and Bacterial Meningitis", Brain Research Reviews, vol. 36, pp. 249-257, 2001.
Ghislain Opdenakker, et al., "Functional Roles and Therapeutic Targeting of Gelatinase B and Chemokines in Multiple Sclerosis", The Lancet Neurology, vol. 2, pp. 747-756, 2003.
J. Thomas Peterson, "Matrix Metalloproteinase Inhibitor Development and the Remodeling of Drug Discovery", Heart Failure Reviews, vol. 9, pp. 63-79, 2004.
Jerry W. Skiles, et al., "The design, Structure, and Therapeutic Application of Matrix Metalloproteinase Inhibitors", Current Medicinal Chemistry, vol. 8, pp. 425-474, 2001.
Jerauld S Skotnicki, et al., "Design Strategies for the Indentification of MMP-13 and Tace Inhibitors", Current Opinion in Drug Discovery and Development, vol. 6, No. 5, pp. 742-759, 2003.
Robert Visse, et al., "Matrix Metalloproteinases and Tissue Inhibitors of Metalloproteinases. Structure, Function, and Biochemistry", Circulation Research, vol. 92, pp. 827-839, 2003.
Catharina M. P. Vos, et al., "Matrix Metalloproteinase-12 is Expressed in Phagocytotic Macrophages in Active Multiple Sclerosis Lesions", Journal of Neuroimmunology, vol. 138, pp. 106-114, 2003.
Carol K. Wada, et al., "Phenoxyphenyl Sulfone N-Formylhydroxylamines (Retrohydroxamates) as Potent, Selective, Orally Bioavailable Matrix Metalloproteinase Inhibitors", Journal of Medicinal Chemistry, vol. 45, No. 1, pp. 219-232, 2002.
C. Graham Knight, et al., "A Novel Coumarin-Labelled Peptide for Sensitive Continuous Assays of the Matrix Metalloproteinases"., FEBS Letters, vol. 296, No. 3, pp. 263-266, 1992.

*Primary Examiner* — Nizal S Chandrakumar
(74) *Attorney, Agent, or Firm* — Oblon, Spivak, McClelland, Maier & Neustadt, L.L.P.

(57) ABSTRACT

The present invention is related to octahydropyrrolo[2,3,c] pyridine derivatives of Formula (I) and use thereof in particular for the treatment and/or prophylaxis of autoimmune disorders, inflammatory diseases, cardiovascular diseases, neurodegenerative diseases, cancer, respiratory diseases and fibrosis, including multiple sclerosis, arthritis, emphysema, chronic obstructive pulmonary disease, liver and pulmonary fibrosis.

10 Claims, No Drawings

OCTAHYDROPYRROLO[2,3C]PYRIDINE DERIVATIVES AND PHARMACEUTICAL USE THEREOF

CROSS REFERENCE TO RELATED APPLICATION

This application is a 371 of PCT/EP05/053501, filed on Jul. 20, 2005, which claims benefit of U.S. Provisional Application 60/589,621, filed on Jul. 21, 2004, and claims priority to European Patent Application No. 04103483.6, filed on Jul. 21, 2004.

FIELD OF THE INVENTION

The present invention is related to octahydropyrrolo[2,3,c]pyridine derivatives of Formula (I), pharmaceutical composition thereof and to their use for the treatment and/or prophylaxis of autoimmune disorders and/or inflammatory diseases, cardiovascular diseases, neurodegenerative diseases, cancer, respiratory diseases and fibrosis. Specifically, the present invention is related to octahydropyrrolo[2,3,c]pyridine derivatives for the modulation, notably the inhibition of the activity or function of matrix metalloproteinases, especially gelatinases and metalloelastase.

BACKGROUND OF THE INVENTION

Metalloproteinases are a superfamily of proteinases (enzymes) named for their dependence on a metal ion (zinc) in the active site.

The matrix metalloproteinases (MMPs) form a metalloproteinase sub-family having as one of major biological function to catalyse the breakdown of connective tissue or extracellular matrix through their ability to hydrolyse various components of the tissue or matrix, such as collagens, gelatins, proteoglycans, fibronectins and elastin.

The matrix metalloproteinase family is further divided according to their function and substrates (Visse al., 2003, Circ. Res., 92, 827-839) and comprises collagenases (MMP-1, MMP-8, MMP-13 and MMP-18), gelatinases (MMP-2 and MMP-9), stromelysins (MMP-3, MMP-10 and MMP-11), membrane-type MMPs (MT-MMP-1 to MT-MMP-6 and MMP-14, MMP-15, MMP-16, MMP-17, MMP-24 and MMP-25), matrilysins (MMP-7 and MMP-26) and other unclassified MMPs such as metalloelastase (MMP-12), enamelysin (MMP-20), epilysin (MMP-28), MMP-19, MMP-22 and MMP-23.

Apart from their role in degrading connective tissue, MMPs are involved in the biosynthesis of TNF-alpha and in the post translational proteolysis processing, or shedding of biologically important membrane proteins (Hooper et al., 1997, Biochem J., 321, 265-279). MMPs for example contribute to the local growth and spread of malignant lesions and therefore have been a target for anti-tumor drug development (Fingleton et al., 2003, Expert Opin. Ther. Targets, 7(3):385-397). Disorders such as inflammatory disorders like arthritis (Clark et al., 2003, Expert. Opin. Ther Targets, 7(1):19-34), respiratory disorders such as emphysema, atherosclerosis (Galis et al., 2002, Circ. Res., 90:251-262), neurological disorders such as degenerative nervous system diseases, multiple sclerosis (Leppert et al., 2001, Brain Res. Rev., 36:249-257), periodontitis (Ingman et al., 1996, J. clin. Periodontal., 23:127-1132) and wound healing have been demonstrated to be associated with MMPs expression and/or activity.

A wide variety of matrix metalloproteinase inhibitors (MMPIs) has been developed (Skiles et al., 2001, Current Medicinal Chemistry, 8, 425-474; Peterson, 2004, Heart Failure Reviews, 9, 63-79; Henrotin et al., 2002, Expert Opin. Ther. Patents, 12(1):29-43). However, many MMPIs exhibit a muscoskeletal syndrome (tendonitis, fibroplasias, mylasia, arthralasia) as a dose-limiting side effect. It has been proposed that inhibition of MMP-1 or MMP-14 may be responsible for these effects.

Therefore, there is an increasing need to develop matrix metalloproteinase inhibitors with a well-defined specificity profile.

Specific inhibitors, especially towards MMP-1, have been reported, including MMP-13 inhibitors (Stotnicki et al., 2003, Current Opinion in Drug Discovery and Development, 6(5):742-759), MMP-12 inhibitors (WO 01/83461), MMP-2 and MMP-9 inhibitors (Wada et al., 2002, J. Biol. Chem. 45, 219-232).

The high relevance of the metalloproteinase pathway in some widely spread diseases stresses the need to develop inhibitors, including selective inhibitors of MMPs, especially of gelatinases such as MMP-2 and/or MMP-9 and/or MMP-12.

SUMMARY OF THE INVENTION

It is an object of the invention to provide substances which are suitable for the treatment and/or prevention of disorders related to autoimmune disorders and/or inflammatory diseases, cardiovascular diseases, neurodegenerative diseases, pre-term labor, stroke cancer, respiratory diseases, endometriosis and fibrosis.

It is further an object of the present invention to provide substances which are suitable for the treatment and/or prevention of multiple sclerosis, arthritis, emphysema, chronic obstructive pulmonary disease and fibrosis.

It is notably an object of the present invention to provide chemical compounds which are able to modulate, especially inhibit the activity or function of matrix metalloproteinases, especially gelatinases and elastase in mammals, especially in humans.

It is furthermore an object of the present invention to provide a new category of pharmaceutical formulations for the treatment of and/or diseases mediated selected from autoimmune disorders, inflammatory diseases, cardiovascular diseases, neurodegenerative diseases, pre-term labor, stroke, cancer, respiratory diseases, endometriosis and fibrosis.

It is furthermore an object of the present invention to provide a process for making chemical compounds according to the invention.

It is finally an object of the present invention to provide a method for the treatment and/or prevention of disorders selected from autoimmune disorders, inflammatory diseases, cardiovascular diseases, neurodegenerative diseases, pre-term labor, cancer, respiratory diseases, stroke, endometriosis and fibrosis.

In a first aspect, the invention provides octahydropyrrolo [2,3,c]pyridine derivatives of Formula (I):

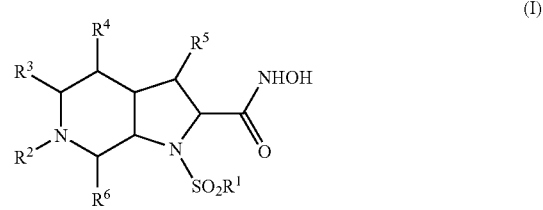

wherein $R^1$, $R^2$, $R^3$, $R^4$, $R^5$ and $R^6$ are defined in the detailed description.

In a second aspect, the invention provides a compound according to Formula (I) for use as a medicament.

In a third aspect, the invention provides a use of a compound according to Formula (I) for the preparation of a pharmaceutical composition for the treatment of a disorder selected from autoimmune disorders, inflammatory diseases, cardiovascular diseases, stroke, neurodegenerative diseases, pre-term labor, cancer, respiratory diseases, endometriosis and fibrosis.

In a fourth aspect, the invention provides a pharmaceutical composition comprising at least one a compound according to Formula (I) and a pharmaceutically acceptable carrier, diluent or excipient thereof.

In a fifth aspect, the invention provides a method of treatment comprising the administration of a compound according to Formula (I) in a patient in need thereof.

In a sixth aspect, the invention provides methods of synthesis of a compound according to Formula (I).

In a seventh aspect, the invention provides compounds according to Formula (IV):

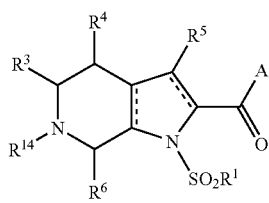

IV wherein $R^1$, $R^2$, $R^3$, $R^4$, $R^5$, $R^6$, $R^{14}$ and A are defined in the detailed description.

DETAILED DESCRIPTION OF THE INVENTION

The following paragraphs provide definitions of the various chemical moieties that make up the compounds according to the invention and are intended to apply uniformly throughout the specification and claims unless an otherwise expressly set out definition provides a broader definition.

The term "MMPs" refers to "matrix metalloproteinases". For recent reviews of MMPs, see Visse et al., 2003 above; Fingleton et al., 2003, above; Clark et al., 2003, above and Doherty et al., 2002, *Expert Opinion Therapeutic Patents* 12(5):665-707.

Illustrative but not limiting examples of such MMPs are:

Collagenases: usually associated with diseases linked to breakdown of collagen-based tissue e.g. rheumatoid arthritis and osteoarthritis:

MMP-1 (also known as collagenase 1, or fibroblast collagenase), substrates collagen I, collagen II, collagen III, gelatin, proteoglycans. Over-expression of this enzyme is believed to be associated with emphysema, with hyperkeratosis and atherosclerosis, overexpressed alone in papillary carcinoma.

MMP-8 (also known as collagenase 2, or neutrophil collagenase), substrates collagen I, collagen II, collagen III, collagen V, collagen VII, collagen IX, gelatin over-expression of which can lead to non-healing chronic ulcers.

MMP-13 (also known as collagenase 3), substrates collagen I, collagen II, collagen III, collagen IV, collagen IX, collagen X, collagen XIV, fibronectin, gelatin, recently identified as being over-expressed alone in breast carcinoma and involved in rheumatoid arthritis.

Stromelysins:

MMP-3 (also known as stromelysin 1), substrates collagen III, collagen IV, collagen V, collagen IX, collagen X, laminin, nidogen, over-expression believed to be involved in atherosclerosis, aneurysm and restenosis.

Gelatinases—inhibition believed to exert a favorable effect on cancer, in particular invasion and metastasis.

MMP-2 (also known as gelatinase A, 72 kDa gelatinase, basement membrane collagenase, or proteoglycanase), substrates Collagen I, Collagen II, Collagen IV, Collagen V, Collagen VII, Collagen X, Collagen XI, collagen XIV, elastin, fibronectin, gelatin, nidogen, believed to be associated with tumor progression through specificity for type IV Collagen (high expression observed in solid tumors and believed to be associated with their ability to grow, invade, develop new blood vessels and metastasize) and to be involved in acute lung inflammation and in respiratory distress syndrome (Krishna et al., 2004, *Expert Opin. Invest. Drugs*, 13(3):255-267).

MMP-9 (also known as gelatinase B, or 92 kDa gelatinase), substrates Collagen I, Collagen III, Collagen IV, Collagen V, Collagen VII, collagen X, Collagen XIV, elastin, fibronectin, gelatin, nidogen. The above enzyme is believed to be associated with tumor progression through specificity for type IV Collagen, to be released by eosinophils in response to exogenous factors such as air pollutants, allergens and viruses, to be involved in the inflammatory response in multiple sclerosis (Opdenakker et al., 2003, *The Lancet Neurology*, 2, 747-756) and asthma and to be involved in acute lung inflammation, respiratory distress syndrome, chronic obstructive pulmonary disorder (COPD) and/or asthma (Krishna et al., 2004, above). MMP-9 is also thought to be involved in stroke (Horstmann et al., 2003, *Stroke* 34(9), 2165-70).

Unclassified MMPs:

MMP-12 (also known as metalloelastase, human macrophage elastase, or HME), substrates fibronectin, larninin, believed to play a role in tumour growth inhibition and regulation of inflammation such as multiple sclerosis (Vos et al., 2003, *Journal of Neuroimmunology*, 138, 106-114) and to play a pathological role in emphysema, COPD (Belvisi et al., 2003, *Inflamm. Res.* 52; 95-100) and in atherosclerosis, aneurysm and restenosis.

The expression "MMP-associated disorder" refers to a disorder which is treatable according to the invention and that encompasses all disorders in which the expression and/or activity of at least one MMP needs to be decreased irrespective of the cause of such disorders. Such disorders include, for example, those caused by inappropriate extracellular matrix (ECM) degradation.

Illustrative but not limiting examples of such MMP-associated disorders are:

Cancer such as breast cancer and solid tumors; inflammatory disorders such as for example inflammatory bowel diseases and neuroinflammation such as multiple sclerosis; lung diseases such as chronic obstructive pulmonary disorder (COPD), emphysema, asthma, acute lung injury, and acute respiratory distress syndrome; dental diseases such as periodontal disease and gingivitis; joint and bone diseases such as osteoarthritis and rheumatoid arthritis; liver diseases such as liver fibrosis, cirrhosis and chronic liver disease; fibrotic diseases such as pulmonary fibrosis, pancreatitis, lupus, glomerulosclerosis, systemic sclerosis, skin fibrosis, post-radiation fibrosis and cystic fibrosis; vascular pathologies such as aortic aneurysm, atherosclerosis, hypertension, cardiomyopathy, stroke and myocardial infarction; restenosis; opthalmological disorders such as diabetic retinopathy, dry eye syndrome, macula degeneration and corneal ulceration and degenerative diseases of the central nervous system such as amyotrophic lateral sclerosis; endometriosis and pre-term labor.

"$C_1$-$C_6$-alkyl" refers to monovalent alkyl groups having 1 to 6 carbon atoms. This term is exemplified by groups such as methyl, ethyl, n-propyl, isopropyl, n-butyl, isobutyl, tert-butyl, n-hexyl, methyl butanoyl and the like. By analogy, "$C_1$-$C_{12}$-alkyl" refers to monovalent alkyl groups having 1 to 12 carbon atoms, including "$C_1$-$C_6$-alkyl" groups and heptyl, octyl, nonyl, decanoyl, undecanoyl and dodecanoyl groups and "$C_1$-$C_{10}$-alkyl" refers to monovalent alkyl groups having 1 to 10 carbon atoms, "$C_1$-$C_8$-alkyl" refers to monovalent alkyl groups having 1 to 8 carbon atoms and "$C_1$-$C_5$-alkyl" refers to monovalent alkyl groups having 1 to 5 carbon atoms.

"Heteroalkyl" refers to $C_1$-$C_{12}$-alkyl, preferably $C_1$-$C_6$-alkyl, wherein at least one carbon has been replaced by a heteroatom selected from O, N or S, including 2-methoxy ethyl.

"Aryl" refers to an unsaturated aromatic carbocyclic group of from 6 to 14 carbon atoms having a single ring (e.g., phenyl) or multiple condensed rings (e.g., naphthyl). Aryl include phenyl, naphthyl, phenantrenyl and the like.

"$C_1$-$C_6$-alkyl aryl" refers to aryl groups having a $C_1$-$C_6$-alkyl substituent, including methyl phenyl, ethyl phenyl and the like.

"Aryl $C_1$-$C_6$-alkyl" refers to $C_1$-$C_6$-alkyl groups having an aryl substituent, including 3-phenylpropanoyl, benzyl and the like.

"Heteroaryl" refers to a monocyclic heteroaromatic, or a bicyclic or a tricyclic fused-ring heteroaromatic group. Particular examples of heteroaromatic groups include optionally substituted pyridyl, pyrrolyl, pyrimidinyl, furyl, thienyl, imidazolyl, oxazolyl, isoxazolyl, thiazolyl, isothiazolyl, pyrazolyl, 1,2,3-triazolyl, 1,2,4-triazolyl, 1,2,3-oxadiazolyl, 1,2,4-oxadiazolyl, 1,2,5-oxadiazolyl, 1,3,4-oxadiazolyl, 1,3,4-triazinyl, 1,2,3-triazinyl, benzofuryl, [2,3-dihydro]benzofuryl, isobenzofuryl, benzothienyl, benzotriazolyl, isobenzothienyl, indolyl, isoindolyl, 3H-indolyl, benzimidazolyl, imidazo[1,2-a]pyridyl, benzothiazolyl, benzoxazolyl, quinolizinyl, quinazolinyl, pthalazinyl, quinoxalinyl, cinnolinyl, napthyridinyl, pyrido[3,4-b]pyridyl, pyrido[3,2-b]pyridyl, pyrido[4,3-b]pyridyl, quinolyl, isoquinolyl, tetrazolyl, 5,6,7,8-tetrahydroquinolyl, 5,6,7,8-tetrahydroisoquinolyl, purinyl, pteridinyl, carbazolyl, xanthenyl or benzoquinolyl.

"$C_1$-$C_6$-alkyl heteroaryl" refers to heteroaryl groups having a $C_1$-$C_6$-alkyl substituent, including methyl furyl and the like.

"Heteroaryl $C_1$-$C_6$-alkyl" refers to $C_1$-$C_6$-alkyl groups having a heteroaryl substituent, including furyl methyl and the like.

"$C_2$-$C_6$-alkenyl" refers to alkenyl groups preferably having from 2 to 6 carbon atoms and having at least 1 or 2 sites of alkenyl unsaturation. Preferable alkenyl groups include ethenyl (—CH═$CH_2$), n-2-propenyl (allyl, —$CH_2$CH═$CH_2$) and the like.

"$C_2$-$C_6$-alkenyl aryl" refers to an aryl groups having a $C_2$-$C_6$-alkenyl substituent, including vinyl phenyl and the like.

"Aryl $C_2$-$C_6$-alkenyl" refers to a $C_2$-$C_6$-alkenyl groups having an aryl substituent, including phenyl vinyl and the like.

"$C_2$-$C_6$-alkenyl heteroaryl" refers to heteroaryl groups having a $C_2$-$C_6$-alkenyl substituent, including vinyl pyridinyl and the like.

"Heteroaryl $C_2$-$C_6$-alkenyl" refers to $C_2$-$C_6$-alkenyl groups having a Heteroaryl substituent, including pyridinyl vinyl and the like.

"$C_2$-$C_6$-alkynyl" refers to alkynyl groups preferably having from 2 to 6 carbon atoms and having at least 1-2 sites of alkynyl unsaturation, preferred alkynyl groups include ethynyl (—C≡CH), propargyl (—$CH_2$C≡CH), and the like.

"$C_3$-$C_8$-cycloalkyl" refers to a saturated carbocyclic group of from 3 to 8 carbon atoms having a single ring (e.g., cyclohexyl) or multiple condensed rings (e.g., norbornyl). $C_3$-$C_8$-cycloalkyl include cyclopentyl, cyclohexyl, norbornyl and the like.

"Heterocycloalkyl" refers to a $C_3$-$C_8$-cycloalkyl group according to the definition above, in which up to 3 carbon atoms are replaced by heteroatoms chosen from the group consisting of O, S, NR, R being defined as hydrogen or methyl. Heterocycloalkyl include pyrrolidine, piperidine, piperazine, morpholine, tetrahydrofurane and the like.

"$C_1$-$C_6$-alkyl cycloalkyl" refers to $C_3$-$C_8$-cycloalkyl groups having a $C_1$-$C_6$-alkyl substituent, including methyl cyclopentyl and the like.

"Cycloalkyl $C_1$-$C_6$-alkyl" refers to $C_1$-$C_6$-alkyl groups having a $C_3$-$C_8$-cycloalkyl substituent, including 3-cyclopentylpropanoyl and the like.

"$C_1$-$C_6$-alkyl heterocycloalkyl" refers to heterocycloalkyl groups having a $C_1$-$C_6$-alkyl substituent, including 1-methylpiperazine and the like.

"Heterocycloalkyl $C_1$-$C_6$-alkyl" refers to $C_1$-$C_6$-alkyl groups having a heterocycloalkyl substituent, including 4-methyl piperidyl and the like.

"Carboxy" refers to the group —C(O)OH.

"Carboxy $C_1$-$C_6$-alkyl" refers to $C_1$-$C_6$-alkyl groups having an carboxy substituent, including 2-carboxyethyl and the like.

"Acyl" refers to the group —C(O)R where R includes "$C_1$-$C_{12}$-alkyl", preferably "$C_1$-$C_6$-alkyl", "aryl", "heteroaryl", "$C_3$-$C_8$-cycloalkyl", "heterocycloalkyl", "aryl $C_1$-$C_6$-alkyl", "heteroaryl $C_1$-$C_6$-alkyl", "$C_3$-$C_8$-cycloalkyl $C_1$-$C_6$-alkyl" or "heterocycloalkyl $C_1$-$C_6$-alkyl".

"Acyl $C_1$-$C_6$-alkyl" to $C_1$-$C_6$-alkyl groups having an acyl substituent, including acetyl, 2-acetylethyl and the like.

"Acyl aryl" refers to aryl groups having an acyl substituent, including 2-acetylphenyl and the like.

"Acyloxy" refers to the group —OC(O)R where R includes H, "$C_1$-$C_6$-alkyl", "$C_2$-$C_6$-alkenyl", "$C_2$-$C_6$-alkynyl", "$C_3$-$C_8$-cycloalkyl", "heterocycloalkyl", "aryl", "heteroaryl", "aryl $C_1$-$C_6$-alkyl" or "heteroaryl $C_1$-$C_6$-alkyl", "aryl $C_2$-$C_6$-alkenyl", "heteroaryl $C_2$-$C_6$-alkenyl", "aryl $C_2$-$C_6$-alkynyl", "heteroaryl $C_2$-$C_6$-alkynyl", "cycloalkyl $C_1$-$C_6$-alkyl", "heterocycloalkyl $C_1$-$C_6$-alkyl".

"Acyloxy $C_1$-$C_6$-alkyl" refers to $C_1$-$C_6$-alkyl groups having an acyloxy substituent, including amino-propionic acid ethyl ester and the like.

"Alkoxy" refers to the group —O—R where R includes "$C_1$-$C_6$-alkyl" or "aryl" or "heteroaryl" or "aryl $C_1$-$C_6$-alkyl" or "heteroaryl $C_1$-$C_6$-alkyl". Preferred alkoxy groups include for example, methoxy, ethoxy, phenoxy and the like.

"Alkoxy $C_1$-$C_6$-alkyl" refers to alkoxy groups having an $C_1$-$C_6$-alkyl substituent, including methoxy, methoxyethyl and the like.

"Alkoxycarbonyl" refers to the group —C(O)OR where R includes H, "$C_1$-$C_6$-alkyl" or "aryl" or "heteroaryl" or "aryl $C_1$-$C_6$-alkyl" or "heteroaryl $C_1$-$C_6$-alkyl" or "heteroalkyl".

"Alkoxycarbonyl $C_1$-$C_6$-alkyl" refers to $C_1$-$C_5$-alkyl groups having an alkoxycarbonyl substituent, including 2-(benzyloxycarbonyl)ethyl and the like.

"Aminocarbonyl" refers to the group —C(O)NRR' where each R, R' includes independently hydrogen or $C_1$-$C_6$-alkyl or aryl or heteroaryl or "aryl $C_1$-$C_6$-alkyl" or "heteroaryl $C_1$-$C_6$-alkyl", including N-phenyl formamide.

"Aminocarbonyl $C_1$-$C_6$-alkyl" refers to $C_1$-$C_6$-alkyl groups having an aminocarbonyl substituent, including 2-(dimethylaminocarbonyl)ethyl, N-ethyl acetamide, N,N-Diethyl-acetamide and the like.

"Acylamino" refers to the group —NRC(O)R' where each R, R' is independently hydrogen, "$C_1$-$C_6$-alkyl", "$C_2$-$C_6$-alkenyl", "$C_2$-$C_6$-alkynyl", "$C_3$-$C_8$-cycloalkyl", "heterocycloalkyl", "aryl", "heteroaryl", "aryl $C_1$-$C_6$-alkyl" or "heteroaryl $C_1$-$C_6$-alkyl", "aryl $C_2$-$C_6$-alkenyl", "heteroaryl $C_2$-$C_6$-alkenyl", "aryl $C_2$-$C_6$-alkynyl", "heteroaryl $C_2$-$C_6$-alkynyl", "cycloalkyl $C_1$-$C_6$-alkyl", "heterocycloalkyl $C_1$-$C_6$-alkyl".

"Acylamino $C_1$-$C_6$-alkyl" refers to $C_1$-$C_6$-alkyl groups having an acylamino substituent, including 2-(propionylamino)ethyl and the like.

"Ureido" refers to the group —NRC(O)NR'R" where each R, R', R" is independently hydrogen, "$C_1$-$C_6$-alkyl", "$C_2$-$C_6$-alkenyl", "$C_2$-$C_6$-alkynyl", "$C_3$-$C_8$-cycloalkyl", "heterocycloalkyl", "aryl", "heteroaryl", "aryl $C_1$-$C_6$-alkyl" or "heteroaryl $C_1$-$C_6$-alkyl", "aryl $C_2$-$C_6$-alkenyl", "heteroaryl $C_2$-$C_6$-alkenyl", "aryl $C_2$-$C_6$-alkynyl", "heteroaryl $C_2$-$C_6$-alkynyl", "cycloalkyl $C_1$-$C_6$-alkyl", "heterocycloalkyl $C_1$-$C_6$-alkyl", and where R' and R", together with the nitrogen atom to which they are attached, can optionally form a 3-8-membered heterocycloalkyl ring.

"Ureido $C_1$-$C_6$-alkyl" refers to $C_1$-$C_6$-alkyl groups having an ureido substituent, including 2-(N'-methylureido)ethyl and the like.

"Carbamate" refers to the group —NRC(O)OR' where each R, R' is independently hydrogen, "$C_1$-$C_6$-alkyl", "$C_2$-$C_6$-alkenyl", "$C_2$-$C_6$-alkynyl", "$C_3$-$C_8$-cycloalkyl", "heterocycloalkyl", "aryl", "heteroaryl", "$C_1$-$C_6$-alkyl aryl" or "heteroaryl $C_1$-$C_6$-alkyl", "aryl $C_2$-$C_6$-alkenyl", "heteroaryl $C_2$-$C_6$-alkenyl", "aryl $C_2$-$C_6$-alkynyl", "heteroaryl $C_2$-$C_6$-alkynyl", "cycloalkyl $C_1$-$C_6$-alkyl", "heterocycloalkyl $C_1$-$C_6$-alkyl".

"Amino" refers to the group —NRR' where each R,R' is independently hydrogen or "$C_1$-$C_6$-alkyl" or "aryl" or "heteroaryl" or "$C_1$-$C_6$-alkyl aryl" or "$C_1$-$C_6$-alkyl heteroaryl", or "cycloalkyl", or "heterocycloalkyl", and where R and R', together with the nitrogen atom to which they are attached, can optionally form a 3-8-membered heterocycloalkyl ring.

"Amino $C_1$-$C_6$-alkyl" refers to $C_1$-$C_5$-alkyl groups having an amino substituent, including 2-(1-pyrrolidinyl)ethyl and the like.

"Ammonium" refers to a positively charged group —N$^+$RR'R", where each R,R',R" is independently "$C_1$-$C_6$-alkyl" or "$C_1$-$C_6$-alkyl aryl" or "$C_1$-$C_6$-alkyl heteroaryl", or "cycloalkyl", or "heterocycloalkyl", and where R and R', together with the nitrogen atom to which they are attached, can optionally form a 3-8-membered heterocycloalkyl ring.

"Ammonium $C_1$-$C_6$-alkyl" refers to $C_1$-$C_6$-alkyl groups having an ammonium substituent, including 1-ethylpyrrolidinium and the like.

"Halogen" refers to fluoro, chloro, bromo and iodo atoms.

"Sulfonyloxy" refers to a group —OSO$_2$—R wherein R is selected from H, "$C_1$-$C_6$-alkyl", "$C_1$-$C_6$-alkyl" substituted with halogens, e.g., an —OSO$_2$—CF$_3$ group, "$C_2$-$C_6$-alkenyl", "$C_2$-$C_6$-alkynyl", "$C_3$-$C_8$-cycloalkyl", "heterocycloalkyl", "aryl", "heteroaryl", "aryl $C_1$-$C_6$-alkyl" or "heteroaryl $C_1$-$C_6$-alkyl", "aryl $C_2$-$C_6$-alkenyl", "heteroaryl $C_2$-$C_6$-alkenyl", "aryl $C_2$-$C_6$-alkynyl", "heteroaryl $C_2$-$C_6$-alkynyl", "cycloalkyl $C_1$-$C_6$-alkyl", "heterocycloalkyl $C_1$-$C_6$-alkyl".

"Sulfonyloxy $C_1$-$C_6$-alkyl" refers to $C_1$-$C_6$-alkyl groups having a sulfonyloxy substituent, including 2-(methylsulfonyloxy)ethyl and the like.

"Sulfonyl" refers to group "—SO$_2$—R" wherein R is selected from H, "aryl", "heteroaryl", "$C_1$-$C_6$-alkyl", "$C_1$-$C_6$-alkyl" substituted with halogens, e.g., an —SO$_2$—CF$_3$ group, "$C_2$-$C_6$-alkenyl", "$C_2$-$C_6$-alkynyl", "$C_3$-$C_8$-cycloalkyl", "heterocycloalkyl", "aryl", "heteroaryl", "aryl $C_1$-$C_6$-alkyl" or "heteroaryl $C_1$-$C_6$-alkyl", "aryl $C_2$-$C_6$-alkenyl", "heteroaryl $C_2$-$C_6$-alkenyl", "aryl $C_2$-$C_6$-alkynyl", "heteroaryl $C_2$-$C_6$-alkynyl", "cycloalkyl $C_1$-$C_6$-alkyl", "heterocycloalkyl $C_1$-$C_6$-alkyl".

"Sulfonyl $C_1$-$C_6$-alkyl" refers to $C_1$-$C_5$-alkyl groups having a sulfonyl substituent, including 2-(methylsulfonyl)ethyl and the like.

"Sulfinyl" refers to a group "—S(O)—R" wherein R is selected from H, "$C_1$-$C_6$-alkyl", "$C_1$-$C_6$-alkyl" substituted with halogens, e.g., a —SO—CF$_3$ group, "$C_2$-$C_6$-alkenyl", "$C_2$-$C_6$-alkynyl", "$C_3$-$C_8$-cycloalkyl", "heterocycloalkyl", "aryl", "heteroaryl", "aryl $C_1$-$C_6$-alkyl" or "heteroaryl $C_1$-$C_6$-alkyl", "aryl $C_2$-$C_6$-alkenyl", "heteroaryl $C_2$-$C_6$-alkenyl", "aryl $C_2$-$C_6$-alkynyl", "heteroaryl $C_2$-$C_6$-alkynyl", "cycloalkyl $C_1$-$C_6$-alkyl", "heterocycloalkyl $C_1$-$C_6$-alkyl".

"Sulfinyl $C_1$-$C_6$-alkyl" refers to $C_1$-$C_6$-alkyl groups having a sulfinyl substituent, including 2-(methylsulfinyl)ethyl and the like.

"Sulfanyl" refers to groups —S—R where R includes H, "$C_1$-$C_6$-alkyl", "$C_1$-$C_6$-alkyl" substituted with halogens, e.g., a —SO—CF$_3$ group, "$C_2$-$C_6$-alkenyl", "$C_2$-$C_6$-alkynyl", "$C_3$-$C_8$-cycloalkyl", "heterocycloalkyl", "aryl", "heteroaryl", "aryl $C_1$-$C_6$-alkyl" or "heteroaryl $C_1$-$C_6$-alkyl", "aryl $C_2$-$C_6$-alkenyl", "heteroaryl $C_2$-$C_6$-alkenyl", "aryl $C_2$-$C_6$-alkynyl", "alkynylheteroaryl $C_2$-$C_6$", "cycloalkyl $C_1$-$C_6$-alkyl", "heterocycloalkyl $C_1$-$C_6$-alkyl". Preferred sulfanyl groups include methylsulfanyl, ethylsulfanyl, and the like.

"Sulfanyl $C_1$-$C_6$-alkyl" refers to $C_1$-$C_5$-alkyl groups having a sulfanyl substituent, including 2-(ethylsulfanyl)ethyl and the like.

"Sulfonylamino" refers to a group —NRSO$_2$—R' where each R, R' includes independently hydrogen, "$C_1$-$C_6$-alkyl", "$C_2$-$C_6$-alkenyl", "$C_2$-$C_6$-alkynyl", "$C_3$-$C_8$-cycloalkyl", "heterocycloalkyl", "aryl", "heteroaryl", "aryl $C_1$-$C_6$-alkyl" or "heteroaryl $C_1$-$C_6$-alkyl", "aryl $C_2$-$C_6$-alkenyl", "heteroaryl $C_2$-$C_6$-alkenyl", "aryl $C_2$-$C_6$-alkynyl", "heteroaryl $C_2$-$C_6$-alkynyl", "cycloalkyl $C_1$-$C_6$-alkyl", "heterocycloalkyl $C_1$-$C_6$-alkyl".

"Sulfonylamino $C_1$-$C_6$-alkyl" refers to $C_1$-$C_6$-alkyl groups having a sulfonylamino substituent, including 2-(ethylsulfonylamino)ethyl and the like.

"Aminosulfonyl" refers to a group —SO$_2$—NRR' where each R, R' includes independently hydrogen, "$C_1$-$C_6$-alkyl", "$C_2$-$C_6$-alkenyl", "$C_2$-$C_6$-alkynyl", "$C_3$-$C_8$-cycloalkyl", "heterocycloalkyl", "aryl", "heteroaryl", "aryl $C_1$-$C_6$-alkyl" or "heteroaryl $C_1$-$C_6$-alkyl", "aryl $C_2$-$C_6$-alkenyl", "heteroaryl $C_2$-$C_6$-alkenyl", "aryl $C_2$-$C_6$-alkynyl", "heteroaryl $C_2$-$C_6$-alkynyl", "cycloalkyl $C_1$-$C_6$-alkyl", "heterocycloalkyl $C_1$-$C_6$-alkyl".

"Aminosulfonyl $C_1$-$C_6$-alkyl" refers to $C_1$-$C_6$-alkyl groups having an aminosulfonyl substituent, including 2-(cyclohexylaminosulfonyl)ethyl and the like.

"Substituted or unsubstituted": Unless otherwise constrained by the definition of the individual substituent, the above set out groups, like "alkenyl", "alkynyl", "aryl", "heteroaryl", "cycloalkyl", "heterocycloalkyl" etc. groups can optionally be substituted with from 1 to 5 substituents selected from the group consisting of "$C_1$-$C_6$-alkyl", "$C_2$-$C_6$-alkenyl", "$C_2$-$C_6$-alkynyl", "cycloalkyl", "heterocycloalkyl", "aryl $C_1$-$C_6$-alkyl", "heteroaryl $C_1$-$C_6$-alkyl", "cycloalkyl $C_1$-$C_6$-alkyl", "heterocycloalkyl $C_1$-$C_6$-alkyl", "amino", "ammonium", "acyl", "acyloxy", "acylamino", "aminocarbonyl", "alkoxycarbonyl", "ureido", "aryl", "carbamate", "heteroaryl", "sulfinyl", "sulfonyl", "alkoxy", "sulfanyl", "halogen", "carboxy", trihalomethyl, cyano, hydroxy, mercapto, nitro, and the like.

"Pharmaceutically acceptable salts or complexes" refers to salts or complexes of the below-identified compounds of Formula (I) that retain the desired biological activity. Examples of such salts include, but are not restricted to acid addition salts formed with inorganic acids (e.g., hydrochloric acid, hydrobromic acid, sulfuric acid, phosphoric acid, nitric acid, and the like), and salts formed with organic acids such as acetic acid, oxalic acid, tartaric acid, succinic acid, malic acid, fumaric acid, maleic acid, ascorbic acid, benzoic acid, tannic acid, pamoic acid, alginic acid, polyglutamic acid, naphthalene sulfonic acid, naphthalene disulfonic acid, and poly-galacturonic acid. Said compounds can also be administered as pharmaceutically acceptable quaternary salts known by a person skilled in the art, which specifically include the quarternary ammonium salt of the formula —NR, R',R"+Z−, wherein R, R', R" is independently hydrogen, alkyl, or benzyl, $C_1$-$C_6$-alkyl, $C_2$-$C_6$-alkenyl, $C_2$-$C_6$-alkynyl, aryl $C_1$-$C_6$-alkyl, heteroaryl $C_1$-$C_6$-alkyl, cycloalkyl, heterocycloalkyl, and Z is a counterion, including chloride, bromide, iodide, —O-alkyl, toluenesulfonate, methylsulfonate, sulfonate, phosphate, or carboxylate (such as benzoate, succinate, acetate, glycolate, maleate, malate, fumarate, citrate, tartrate, ascorbate, cinnamoate, mandeloate, and diphenylacetate).

"Pharmaceutically active derivative" refers to any compound that upon administration to the recipient, is capable of providing directly or indirectly, the activity disclosed herein. The term "indirectly" also encompasses prodrugs which may be converted to the active form of the drug via endogenous enzymes or metabolism. Said prodrug is comprised of the active drug compound itself and a chemical masking group.

An "interferon" or "IFN", as used herein, is intended to include any molecule defined as such in the literature, comprising for example any types of IFNs mentioned in the above section "Background of the Invention". In particular, IFN-α, IFN-β and IFN-γ are included in the above definition. IFN-β is the preferred IFN according to the present invention. IFN-β suitable in accordance with the present invention is commercially available e.g. as Rebif® (Serono), Avonex® (Biogen) or Betaferon® (Schering).

The term "interferon-beta (IFN-beta or IFN-β)", as used herein, is intended to include fibroblast interferon in particular of human origin, as obtained by isolation from biological fluids or as obtained by DNA recombinant techniques from prokaryotic or eukaryotic host cells, as well as its salts, functional derivatives, variants, analogs and active fragments. Preferably, IFN-beta is intended to mean recombinant Interferon beta-1a.

IFN-β suitable in accordance with the present invention is commercially available e.g. as Rebif® (Serono), Avonex® (Biogen) or Betaferon® (Schering). The use of interferons of human origin is also preferred in accordance with the present invention. The term interferon, as used herein, is intended to encompass salts, functional derivatives, variants, analogs and active fragments thereof.

Rebif® (recombinant interferon-β) is the latest development in interferon therapy for multiple sclerosis (MS) and represents a significant advance in treatment. Rebif® is interferon (IFN)-beta 1a, produced from mammalian cell lines. It was established that interferon beta-1a given subcutaneously three times per week is efficacious in the treatment of Relapsing-Remitting Multiple Sclerosis (RRMS). Interferon beta-1a can have a positive effect on the long-term course of MS by reducing number and severity of relapses and reducing the burden of the disease and disease activity as measured by MRI.

The dosing of IFN-β in the treatment of relapsing-remitting MS according to the invention depends on the type of IFN-β used.

In accordance with the present invention, where IFN is recombinant IFN-β1b produced in *E. Coli*, commercially available under the trademark Betaseron®, it may preferably be administered sub-cutaneously every second day at a dosage of about of 250 to 300 μg or 8 MIU to 9.6 MIU per person.

In accordance with the present invention, where IFN is recombinant IFN-β1a, produced in Chinese Hamster Ovary cells (CHO cells), commercially available under the trademark Avonex®, it may preferably be administered intra-muscularly once a week at a dosage of about of 30 μg to 33 μg or 6 MIU to 6.6 MIU per person.

In accordance with the present invention, when IFN is recombinant IFN-β1a, produced in Chinese Hamster Ovary cells (CHO cells), commercially available under the trademark Rebif®, it may preferably be administered sub-cutaneously three times a week (TIW) at a dosage of 22 to 44 μg or 6 MIU to 12 MIU per person.

It has now been found that compounds of the present invention are modulators of the matrix metalloproteinases, especially gelatinases and elastase. When the matrix metalloproteinase enzyme is inhibited by the compounds of the present invention, the inhibited MMP(s) is (are) unable to exert its enzymatic, biological and/or pharmacological effects. The compounds of the present invention are therefore useful in the treatment and prevention of autoimmune disorders and/or inflammatory diseases, cardiovascular diseases, neurodegenerative diseases, cancer, pre-term labor, endometriosis, respiratory diseases and fibrosis.

General Formula (I) according to the present invention also comprises its tautomers, its geometrical isomers, its optically active forms as enantiomers, diastereomers and its racemate forms, as well as pharmaceutically acceptable salts thereof. Preferred pharmaceutically acceptable salts of the Formula (I) are acid addition salts formed with pharmaceutically acceptable acids like hydrochloride, hydrobromide, sulfate or bisulfate, phosphate or hydrogen phosphate, acetate, benzoate, succinate, fumarate, maleate, lactate, citrate, tartrate, gluconate, methanesulfonate, benzenesulfonate, and para-toluenesulfonate salts.

The compounds according to Formula (I) are suitable for the modulation, notably the inhibition of the activity of matrix metalloproteinases. It is therefore believed that the compounds of the present invention are also particularly useful for the treatment and/or prevention of disorders which are mediated by matrix metalloproteinases, especially gelatinases and elastases. Said treatment involves the modulation—notably the inhibition or the down regulation—of the MMPs, including MMP-2 and/or MMP-9 and/or MMP-12.

In one embodiment, the invention provides derivatives of Formula (I) wherein $R^1$ is selected from optionally substituted aryl, optionally substituted heteroaryl, optionally substituted $C_3$-$C_8$-cycloalkyl and optionally substituted heterocycloalkyl; $R^2$ is selected from hydrogen, optionally substituted $C_1$-$C_6$ alkyl, optionally substituted $C_2$-$C_6$ alkenyl, optionally substituted $C_2$-$C_6$ alkynyl, optionally substituted acyl, optionally substituted acyl $C_1$-$C_6$-alkyl, optionally substituted aminocarbonyl, optionally substituted aminocarbonyl $C_1$-$C_6$-alkyl, optionally substituted alkoxycarbonyl and optionally substituted sulfonyl. $R^3$, $R^4$, $R^5$ and $R^6$ are independently selected from hydrogen, halogen and optionally substituted $C_1$-$C_6$ alkyl.

In a preferred embodiment, the invention provides derivatives of Formula (I) wherein $R^1$ is optionally substituted aryl.

In a further preferred embodiment, the invention provides derivatives of Formula (I) wherein $R^1$ is optionally substituted phenyl, including phenyl, 4-methoxyphenyl and 4-(pyridin-4-yloxy)phenyl.

In another preferred embodiment, the invention provides derivatives of Formula (I) wherein $R^1$ is optionally substituted heteroaryl, including pyridinyl.

In another preferred embodiment, the invention provides derivatives of Formula (I) wherein $R^2$ is selected from hydrogen, —$(CH_2)_nC(O)$—$(CH_2)_m$—$R^8$, —$C(O)$—$O$—$R^{10}$, —$(CH_2)_nC(O)NR^8R^9$ and —$SO_2$—$R^{15}$; $R^8$ and $R^9$ are independently selected from hydrogen, optionally substituted $C_1$-$C_{12}$ alkyl, including $C_1$-$C_6$ alkyl, methyl, ethyl, 3-methyl butanoyl and dodecanoyl; optionally substituted $C_2$-$C_6$ alkenyl; optionally substituted $C_2$-$C_6$ alkynyl; optionally substituted aryl, including phenyl, biphenyl and 4-methoxyphenyl; optionally substituted heteroaryl; optionally substituted $C_3$-$C_8$-cycloalkyl, including cyclopentyl and optionally substituted heterocycloalkyl; $R^{10}$ is selected from optionally substituted $C_1$-$C_6$ alkyl; optionally substituted $C_2$-$C_6$ alkenyl; optionally substituted $C_2$-$C_6$ alkynyl; optionally substituted heteroalkyl, including 2-methoxy ethyl; optionally substituted aryl, including phenyl; optionally substituted heteroaryl; optionally substituted $C_3$-$C_8$-cycloalkyl and optionally substituted heterocycloalkyl; $R^{15}$ is selected from optionally substituted $C_1$-$C_{12}$ alkyl, including methyl, ethyl, 3-methyl butanoyl and dodecanoyl; optionally substituted $C_2$-$C_6$ alkenyl; optionally substituted $C_2$-$C_6$ alkynyl; optionally substituted aryl, including phenyl, biphenyl and 4-methoxyphenyl; optionally substituted heteroaryl; optionally substituted $C_3$-$C_8$-cycloalkyl, including cyclopentyl and optionally substituted heterocycloalkyl; m and n are independently selected from 0, 1 and 2.

In another preferred embodiment, the invention provides derivatives of Formula (I) wherein $R^3$, $R^4$, $R^5$ and $R^6$ are hydrogen.

In another preferred embodiment, the invention provides derivatives of Formula (I) wherein n is selected from 0 and 1.

In another preferred embodiment, the invention provides derivatives of Formula (I) wherein $R^1$ is optionally substituted phenyl; $R^2$ is selected from hydrogen, —$(CH_2)_nC(O)$—$(CH_2)_m$—$R^8$, —$C(O)$—$O$—$R^{10}$ and —$(CH_2)_nC(O)NR^8R^9$; $R^8$ is selected from hydrogen, optionally substituted $C_1$-$C_{10}$ alkyl, including methyl, ethyl, 3-methyl butanoyl and dodecanoyl; optionally substituted $C_2$-$C_6$ alkenyl; optionally substituted $C_2$-$C_6$ alkynyl; optionally substituted aryl, including phenyl, biphenyl and 4-methoxyphenyl; optionally substituted heteroaryl; optionally substituted $C_3$-$C_8$-cycloalkyl, including cyclopentyl and optionally substituted heterocycloalkyl; $R^9$ is H; $R^{10}$ is selected from optionally substituted $C_1$-$C_6$ alkyl; optionally substituted $C_2$-$C_6$ alkenyl; optionally substituted $C_2$-$C_6$ alkynyl; optionally substituted aryl, including phenyl; optionally substituted heteroaryl; optionally substituted $C_3$-$C_8$-cycloalkyl and optionally substituted heterocycloalkyl; $R^3$, $R^4$, $R^5$ and $R^6$ are hydrogen; m is selected from 0, 1 and 2 and n is selected from 0 and 1.

In another preferred embodiment, the invention provides derivatives of Formula (I) wherein $R^1$ is phenyl, $R^2$ is —$SO_2$—$R^{15}$; $R^{15}$ is selected from optionally substituted $C_1$-$C_6$ alkyl, optionally substituted aryl, optionally substituted heteroaryl, optionally substituted $C_3$-$C_8$-cycloalkyl and optionally substituted heterocycloalkyl; $R^3$, $R^4$, $R^5$ and $R^6$ are hydrogen.

In another preferred embodiment, the invention provides derivatives of Formula (I) wherein $R^1$ is phenyl, $R^2$ is selected from hydrogen, —$(CH_2)_n$—$C(O)$—$(CH_2)_m$—$R^8$, —$C(O)$—$O$—$R^{10}$ and —$(CH_2)_nC(O)NHR^8$; $R^8$ is selected from optionally substituted $C_1$-$C_6$ alkyl, optionally substituted $C_2$-$C_6$ alkenyl, optionally substituted $C_2$-$C_6$ alkynyl, optionally substituted aryl, optionally substituted heteroaryl, optionally substituted $C_3$-$C_8$-cycloalkyl and optionally substituted heterocycloalkyl; $R^3$, $R^4$, $R^5$ and $R^6$ are hydrogen; $R^{10}$ is selected from optionally substituted $C_1$-$C_6$ alkyl, optionally substituted $C_2$-$C_6$ alkenyl, optionally substituted $C_2$-$C_6$ alkynyl, optionally substituted aryl, optionally substituted heteroaryl, optionally substituted $C_3$-$C_8$-cycloalkyl and optionally substituted heterocycloalkyl; m is selected from 0, 1 and 2 and n is selected from 0 and 1.

Compounds of the present invention include in particular those of the group consisting of:

rel-(2S,3aS,7aR)-6-benzoyl-N-hydroxy-1-[(4-methoxyphenyl)sulfonyl]octahydro-1H-pyrrolo[2,3-c]pyridine-2-carboxamide;

rel-(2S,3aS,7aR)-6-acetyl-N-hydroxy-1-[(4-methoxyphenyl)sulfonyl]octahydro-1H-pyrrolo[2,3-c]pyridine-2-carboxamide;

rel-(2S,3aS,7aR)—N-hydroxy-1-[(4-methoxyphenyl)sulfonyl]-6-(3-methylbutanoyl) octahydro-1H-pyrrolo[2,3-c]pyridine-2-carboxamide;

rel-(2S,3aS,7aR)-6-(3-cyclopentylpropanoyl)-N-hydroxy-1-[(4-methoxyphenyl)sulfonyl]octahydro-1H-pyrrolo[2,3-c]pyridine-2-carboxamide;

2-methoxyethyl-rel-(2S,3aS,7aR)-2-[(hydroxyamino)carbonyl]-1-[(4-methoxyphenyl)sulfonyl]octahydro-6H-pyrrolo[2,3-c]pyridine-6-carboxylate;

rel-(2S,3aS,7aR)-6-dodecanoyl-N-hydroxy-1-[(4-methoxyphenyl)sulfonyl]octahydro-1H-pyrrolo[2,3-c]pyridine-2-carboxamide;

rel-(2S,3aS,7aR)-6-(cyclopentylcarbonyl)-N-hydroxy-1-[(4-methoxyphenyl)sulfonyl]octahydro-1H-pyrrolo[2,3-c]pyridine-2-carboxamide;

rel-(2S,3aS,7aR)—N-hydroxy-1-[(4-methoxyphenyl)sulfonyl]-6-(3-phenylpropanoyl)octahydro-1H-pyrrolo[2,3-c]pyridine-2-carboxamide;

rel-(2S,3aS,7aR)—N-hydroxy-1-[(4-methoxyphenyl)sulfonyl]-6-(methylsulfonyl)octahydro-1H-pyrrolo[2,3-c]pyridine-2-carboxamide;

rel-(2S,3aS,7aR)—N-hydroxy-1,6-bis[(4-methoxyphenyl)sulfonyl]octahydro-1H-pyrrolo[2,3-c]pyridine-2-carboxamide;

rel-(2S,3aS,7aR)—N-hydroxy-6-(methylsulfonyl)-1-{[4-(pyridin-4-yloxy)phenyl]sulfonyl}octahydro-1H-pyrrolo[2,3-c]pyridine-2-carboxamide;

rel-(2S,3aS,7aR)-6-(biphenyl-4-ylcarbonyl)-N-hydroxy-1-[(4-methoxyphenyl)sulfonyl]octahydro-1H-pyrrolo[2,3-c]pyridine-2-carboxamide;

rel-(2S,3aS,7aR)-6-(biphenyl-4-ylsulfonyl)-N-hydroxy-1-[(4-methoxyphenyl)sulfonyl]octahydro-1H-pyrrolo[2,3-c]pyridine-2-carboxamide;

rel-(2S,3aS,7aR)-6-[2-(diethylamino)-2-oxoethyl]-N-hydroxy-1-[(4-methoxyphenyl)sulfonyl]octahydro-1H-pyrrolo[2,3-c]pyridine-2-carboxamide;

rel-(2S,3aS,7aR)-6-[2-(ethylamino)-2-oxoethyl]-N-hydroxy-1-[(4-methoxyphenyl)sulfonyl]octahydro-1H-pyrrolo[2,3-c]pyridine-2-carboxamide;

rel-(2S,3aS,7aR)—$N^2$-hydroxy-1-[(4-methoxyphenyl)sulfonyl]-$N^6$-phenyloctahydro-6H-pyrrolo[2,3-c]pyridine-2,6-dicarboxamide;

rel-(2S,3aS,7aR)—N-hydroxy-1-[(4-methoxyphenyl)sulfonyl]octahydro-1H-pyrrolo[2,3-c]pyridine-2-carboxamide;

benzyl rel-(2S,3aS,7aR)-2-[(hydroxyamino)carbonyl]-1-[(4-methoxyphenyl)sulfonyl]octahydro-6H-pyrrolo[2,3-c]pyridine-6-carboxylate.

In another embodiment of the invention, are provided octahydropyrrolo[2,3,c]pyridine derivatives according to Formula (I) for use as a medicament.

In another embodiment of the invention, is provide a use of octahydropyrrolo[2,3,c]pyridine derivatives according to Formula (I) for the preparation of a medicament for the prophylaxis and/or treatment of a disorder selected from autoimmune disorders, inflammatory diseases, cardiovascular diseases, neurodegenerative diseases, stroke, pre-term labor, cancer, respiratory diseases, fibrosis, endometriosis, especially including multiple sclerosis, arthritis, emphysema, chronic obstructive pulmonary disease (COPD), liver, skin and pulmonary fibrosis.

In another embodiment of the invention, is provided a use of octahydropyrrolo[2,3,c]pyridine derivatives according to Formula (I) for the modulation, in particular for the inhibition, of the matrix metalloproteinase activity. Particularly, is provided a use according to the invention wherein said matrix metalloproteinase is selected from MMP-2, MMP-9 and MMP-12.

In another embodiment, the invention provides a method of treatment and/or prophylaxis of a disease comprising the administration of a compound according to Formula (I), in a patient in need thereof and wherein the disease is selected from autoimmune disorders, inflammatory diseases, cardiovascular diseases, neurodegenerative diseases, stroke, preterm labor, cancer, respiratory diseases, fibrosis, endometriosis, especially including multiple sclerosis, arthritis, emphysema, chronic obstructive pulmonary disease (COPD), liver, skin and pulmonary fibrosis.

In another embodiment, the invention provides a process for the preparation of an octahydropyrrolo[2,3,c]pyridine derivative, according to the invention, comprising the step of reacting a compound of Formula (IIa) with a protected or non protected hydroxylamine $H_2NO—R^{12}$ derivative:

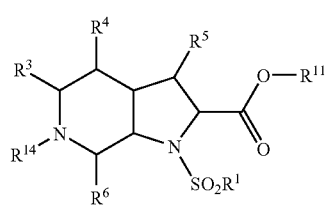

(IIa)

wherein $R^1$, $R^2$, $R^3$, $R^4$, $R^5$ and $R^6$ are defined above; $R^{11}$ is selected from H and optionally substituted $C_1$-$C_6$ alkyl; $R^{14}$ is selected from hydrogen, $R^2$ and a protective group such as Boc, Fmoc, Benzyloxycarbonyl or benzyl; $R^{12}$ is selected from H and a protecting group such as t-butyl, benzyl, trialkylsilyl or tetrahydropyranyl (THP). The resulting compound may then be deprotected by known methods to provide an octahydropyrrolo[2,3,c]pyridine derivative according to Formula (I).

A preferred process for the preparation octahydropyrrolo [2,3,c]pyridine of Formula (I) is represented on Scheme 3 below and consists of converting the intermediate carboxylic ester of Formula (IIa')—wherein $R^{11}$ is $C_1$-$C_6$ alkyl; $R^{13}$ is H, —$SO_2R^1$ and a protective group such as Boc, Fmoc, Benzyloxycarbonyl or benzyl; $R^{14}$ is H, $R^2$ and a protective group such as Boc, Fmoc, Benzyloxycarbonyl or benzyl—into a carboxylic acid of Formula (IIa) wherein $R^{11}$ is H; $R^{13}$ and $R^{14}$ as above defined. The carboxylic acids of Formula (IIa') may then be converted to compound of Formula (Ia) by its reaction with a protected hydroxylamine $H_2NO—R^{12}$ and an amide-coupling reagent to give intermediate of Formula (Ia) where $R^{12}$ is a t-butyl, benzyl or trialkylsilyl moiety.

Alternatively, intermediate of formula (Ia) can be prepared by reacting the carboxylic esters of Formula (IIa') with trimethylaluminium and a protected hydroxylamine derivative $H_2NO—R^{12}$, wherein $R^{12}$ is a benzyl (Scheme 3 below). Octahydropyrrolo[2,3,c]pyridine of Formula (I) may then be obtained by the deprotection of its precursor of Formula (Ia) by known methods.

A more economical process consists of converting the carboxylic ester of Formula (IIa')—wherein $R^{11}$ is $C_1$-$C_6$ alkyl; $R^{13}$ is H, —$SO_2R^1$ and a protective group such as Boc, Fmoc, Benzyloxycarbonyl or benzyl; $R^{14}$ is H, $R^2$ and a protective group such as Boc, Fmoc, Benzyloxycarbonyl or benzyl— into compound of Formula (Ia) by its reaction with hydroxylamine in polar solvent such as ethanol. The carboxylic acids of Formula (IIa') may also be reacted with hydroxylamine and an amid-coupling reagent to give directly octahydropyrrolo [2,3,c]pyridine of Formula (I).

Scheme 3

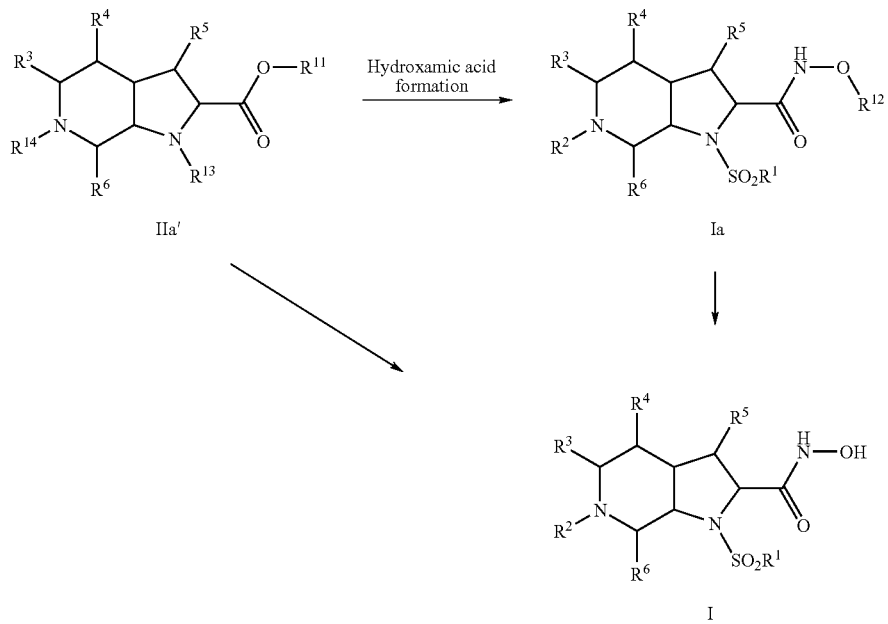

In another embodiment, the invention provides a compound according to Formula (IV):

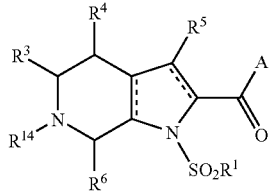

IV wherein $R^1$, $R^2$, $R^3$, $R^4$, $R^5$ and $R^6$ are defined above; $R^{14}$ is selected from H, $R^2$ and a protecting group selected from Boc, Benzyloxycarbonyl, benzyl or Fmoc; A is selected from —OH, $C_1$-$C_6$ alkoxy and —$NHOR^{12}$; $R^{12}$ is selected from H and a protecting group such as t-butyl, benzyl, trialkylsilyl or tetrahydropyranyl (THP).

In another embodiment, the invention provides a compound according to Formula (IV) selected from the group:
ethyl rel-(2S,3aS,7aR)-6-benzoyl-1-[(4-methoxyphenyl)sulfonyl]octahydro-1H-pyrrolo[2,3-c]pyridine-2-carboxylate;
rel-(2S,3aS,7aR)-6-benzoyl-1-[(4-methoxyphenyl)sulfonyl]octahydro-1H-pyrrolo[2,3-c]pyridine-2-carboxylic acid;
rel-(2S,3aS,7aR)-6-benzoyl-N-(benzyloxy)-1-[(4-methoxyphenyl)sulfonyl]octahydro-1H-pyrrolo[2,3-c]pyridine-2-carboxamide;
ethyl 6-acetyl-1-[(4-methoxyphenyl)sulfonyl]-4,5,6,7-tetrahydro-1H-pyrrolo[2,3-c]pyridine-2-carboxylate;
ethyl rel-(2S,3aS,7aR)-6-acetyl-1-[(4-methoxyphenyl)sulfonyl]octahydro-1H-pyrrolo[2,3-c]pyridine-2-carboxylate;
rel-(2S,3aS,7aR)-6-acetyl-1-[(4-methoxyphenyl)sulfonyl]octahydro-1H-pyrrolo[2,3-c]pyridine-2-carboxylic acid;
rel-(2S,3aS,7aR)-6-acetyl-N-(benzyloxy)-1-[(4-methoxyphenyl) sulfonyl]octahydro-1H-pyrrolo[2,3-c]pyridine-2-carboxamide;
ethyl rel-(2S,3aS,7aR)-1-[(4-methoxyphenyl)sulfonyl]-6-(3-methyl butanoyl)octahydro-1H-pyrrolo[2,3-c]pyridine-2-carboxylate;
rel-(2S,3aS,7aR)—N-(benzyloxy)-1-[(4-methoxyphenyl) sulfonyl]-6-(3-methylbutanoyl) octahydro-1H-pyrrolo[2,3-c]pyridine-2-carboxamide;
ethyl rel-(2S,3aS,7aR)-6-[2-(ethylamino)-2-oxoethyl]-1-[(4-methoxy phenyl)sulfonyl]octahydro-1H-pyrrolo[2,3-c]pyridine-2-carboxylate;
rel-(2S,3aS,7aR)-6-[2-(ethylamino)-2-oxoethyl]-1-[(4-methoxyphenyl)sulfonyl]octahydro-1H-pyrrolo[2,3-c]pyridine-2-carboxylic acid;
rel-(2S,3aS,7aR)—N-(benzyloxy)-6-[2-(ethylamino)-2-oxoethyl]-1-[(4-methoxyphenyl)sulfonyl]octahydro-1H-pyrrolo[2,3-c]pyridine-2-carboxamide;
ethyl rel-(2S,3aS,7aR)-6-(anilinocarbonyl)-1-[(4-methoxyphenyl)sulfonyl]octahydro-1H-pyrrolo[2,3-c]pyridine-2-carboxylate;
rel-(2S,3aS,7aR)-6-(anilinocarbonyl)-1-[(4-methoxyphenyl)sulfonyl]octahydro-1H-pyrrolo[2,3-c]pyridine-2-carboxylic acid;
rel-(2S,3aS,7aR)—N2-(benzyloxy)-1-[(4-methoxyphenyl)sulfonyl]-N6-phenyloctahydro-6H-pyrrolo[2,3-c]pyridine-2,6-dicarboxamide;
6-benzyl 2-ethyl rel-(2S,3aS,7aR)-1-[(4-methoxyphenyl) sulfonyl]octahydro-6H-pyrrolo[2,3-c]pyridine-2,6-dicarboxylate;
rel-(2S,3aS,7aR)-6-[(benzyloxy)carbonyl]-1-[(4-methoxyphenyl)sulfonyl]octahydro-1H-pyrrolo[2,3-c]pyridine-2-carboxylic acid;
benzyl rel-(2S,3aS,7aR)-2-{[(benzyloxy)amino]carbonyl}-1-[(4-methoxyphenyl)sulfonyl]octahydro-6H-pyrrolo[2,3-c]pyridine-6-carboxylate;
rel-(2S,3aS,7aR)-6-[(benzyloxy)carbonyl]-1-[(4-methoxyphenyl)sulfonyl]octahydro-1H-pyrrolo[2,3-c]pyridine-2-carboxylic acid;
6-acetyl-1-[(4-methoxyphenyl)sulfonyl]-4,5,6,7-tetrahydro-1H-pyrrolo[2,3-c]pyridine-2-carboxylic acid;
6-acetyl-N-(benzyloxy)-1-[(4-methoxyphenyl)sulfonyl]-4,5,6,7-tetrahydro-1H-pyrrolo[2,3-c]pyridine-2-carboxamide.

The compounds of invention have been named according to the standards used in the program "ACD/Name" from Advanced Chemistry Development Inc., ACD/Labs (7.00 Release).

The compounds of Formula (I) are useful for the treatment and/or prophylaxis of autoimmune disorders, inflammatory diseases, cardiovascular diseases, neurodegenerative diseases, cancer, respiratory diseases and fibrosis, including multiple sclerosis, arthritis, emphysema, chronic obstructive pulmonary disease, liver and pulmonary fibrosis.

The derivatives exemplified in this invention may be prepared from readily available starting materials using the following general methods and procedures. It will be appreciated that where typical or preferred experimental conditions (i.e. reaction temperatures, time, moles of reagents, solvents etc.) are given, other experimental conditions can also be used unless otherwise stated. Optimum reaction conditions may vary with the particular reactants or solvents used, but such conditions can be determined by the person skilled in the art, using routine optimisation procedures.

In an embodiment, the compounds of the invention can be used in the treatment of autoimmune diseases, especially demyelinating diseases such as multiple sclerosis, alone or in combination with a co-agent useful in the treatment of autoimmune diseases, wherein the co-agent is for example selected from the following compounds:
  (a) Interferons, e.g. pegylated or non-pegylated interferons, e.g. administered by sub-cutaneous, intramuscular or oral routes, preferably interferon beta;
  (b) Glatiramer, e.g. in the acetate form;
  (c) Immunosuppressants with optionally antiproliferative/antineoplastic activity, e.g. mitoxantrone, methotrexate, azathioprine, cyclophosphamide, or steroids, e.g. methylprednisolone, prednisone or dexamethasone, or steroid-secreting agents, e.g. ACTH;
  (d) Adenosine deaminase inhibitors, e.g. Cladribine;
Inhibitors of VCAM-1 expression or antagonists of its ligand, e.g. antagonists of the α4/β1 integrin VLA-4 and/or alpha-4-beta-7 integrins, e.g. natalizumab (ANTEGRENO).

When employed as pharmaceuticals, the compounds of the present invention are typically administered in the form of a pharmaceutical composition. Hence, pharmaceutical compositions comprising a compound of Formula (I) and a pharmaceutically acceptable carrier, diluent or excipient therefore are also within the scope of the present invention. A person skilled in the art is aware of a whole variety of such carrier, diluent or excipient compounds suitable to formulate a pharmaceutical composition.

The compounds of the invention, together with a conventionally employed adjuvant, carrier, diluent or excipient may be placed into the form of pharmaceutical compositions and unit dosages thereof, and in such form may be employed as solids, such as tablets or filled capsules, or liquids such as solutions, suspensions, emulsions, elixirs, or capsules filled with the same, all for oral use, or in the form of sterile injectable solutions for parenteral (including subcutaneous use). Such pharmaceutical compositions and unit dosage forms thereof may comprise ingredients in conventional proportions, with or without additional active compounds or principles, and such unit dosage forms may contain any suitable effective amount of the active ingredient commensurate with the intended daily dosage range to be employed.

Pharmaceutical compositions containing an octahydropyrrolo[2,3,c]pyridine derivatives of this invention can be prepared in a manner well known in the pharmaceutical art and comprise at least one active compound. Generally, the compounds of this invention are administered in a pharmaceutically effective amount. The amount of the compound actually administered will typically be determined by a physician, in the light of the relevant circumstances, including the condition to be treated, the chosen route of administration, the actual compound administered, the age, weight, and response of the individual patient, the severity of the patient's symptoms, and the like.

The pharmaceutical compositions of the present invention can be administered by a variety of routes including oral, rectal, transdermal, subcutaneous, intravenous, intramuscular and intranasal. The compositions for oral administration can take the form of bulk liquid solutions or suspensions, or bulk powders. More commonly, however, the compositions are presented in unit dosage forms to facilitate accurate dosing. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient. Typical unit dosage forms include prefilled, premeasured ampoules or syringes of the liquid compositions or pills, tablets, capsules or the like in the case of solid compositions. In such compositions, the derivative of the invention is usually a minor component (from about 0.1 to about 50% by weight or preferably from about 1 to about 40% by weight) with the remainder being various vehicles or carriers and processing aids helpful for forming the desired dosing form.

Liquid forms suitable for oral administration may include a suitable aqueous or nonaqueous vehicle with buffers, suspending and dispensing agents, colorants, flavors and the like. Solid forms may include, for example, any of the following ingredients, or compounds of a similar nature: a binder such as microcrystalline cellulose, gum tragacanth or gelatine; an excipient such as starch or lactose, a disintegrating agent such as alginic acid, Primogel, or corn starch; a lubricant such as magnesium stearate; a glidant such as colloidal silicon dioxide; a sweetening agent such as sucrose or saccharin; or a flavoring agent such as peppermint, methyl salicylate, or orange flavoring.

Injectable compositions are typically based upon injectable sterile saline or phosphate-buffered saline or other injectable carriers known in the art. As above mentioned, the an octahydropyrrolo[2,3,c]pyridine derivatives derivatives of Formula (I) in such compositions is typically a minor component, frequently ranging between 0.05 to 10% by weight with the remainder being the injectable carrier and the like.

The above described components for orally administered or injectable compositions are merely representative. Further materials as well as processing techniques and the like are set out in Part 5 of *Remington's Pharmaceutical Sciences*, 20$^{th}$ Edition, 2000, Marck Publishing Company, Easton, Pa., which is incorporated herein by reference.

The compounds of this invention can also be administered in sustained release forms or from sustained release drug delivery systems. A description of representative sustained release materials can also be found in the incorporated materials in *Remington's Pharmaceutical Sciences*.

Synthesis of Compounds of the Invention:

The novel derivatives according to Formula (I) can be prepared from readily available starting materials by several synthetic approaches, using both solution-phase and solid-phase chemistry protocols. Examples of synthetic pathways for the compounds of the invention will be described below.

The following abbreviations refer respectively to the definitions below:

Atm (atmosphere), min (minute), eq (equivalent), g (gram), hr (hour), kDa (KiloDalton), kg (kilogram), mg (milligram), μg (microgram), MHz (Megahertz), mL (milliliter), μl (microliter), mmol (millimole), mM (millimolar), rt (room temperature), ALAT (Alanine Amino Transferase), AMEBA (4-(4-Formyl-3-methoxyphenoxy)-butyryl AM resin), ASAT (Aspartate Amino Transferase), Boc (tert-butoxycarbonyl), CMC (carboxymethylcellulose), DCM (dichloromethane), DMF (dimethylformamide), DMSO (Dimethyl Sulfoxide), EDTA (ethylene diamine tetraacetic acid), Fmoc (9-Fluorenylmethoxycarbonyl), HPLC (High Performance Liquid Chromatography), IL-2 (Interleukin-2), i.p. (intra-peritoneal), LC (Liquid Chromatography), MMP (matrix metalloproteinase), NMM (N-methyl morpholine), NMR (Nuclear Magnetic Resonance), PBS (Phosphate Buffered Saline), p.o. (per os), s.c. (sub-cutaneous), SPE (Solid phase Extraction), TEA (triethylamine), TFA (trifluoro-acetic acid), THF (tetrahydrofuran), THP (Tetrahydropyranyl), TLC (Thin Layer Chromatography), Z (Benzyloxycarbonyl).

Synthetic Approaches:

One synthetic approach (Scheme 1 below) for the preparation of octahydropyrrolo[2,3,c]pyridine of Formula (I) consists in converting the carboxylic acids of Formula (IIa)—wherein $R^{11}$ is H; $R^{13}$ is selected from H, $SO_2R^1$ and a protective group such as Boc, Fmoc, Z or benzyl; $R^{14}$ is selected from H, $R^2$ and a protective group such as Boc, Fmoc, Z or benzyl—into the corresponding acid chloride or anhydride, or by reacting it with a suitable peptide coupling reagent, followed by reaction with hydroxylamine, or with a protected hydroxylamine $H_2NO—R^{12}$ derivative to give a compound of Formula (Ia) where $R^{12}$ is H or a protecting group such as t-butyl, benzyl, trialkylsilyl or a suitable protecting group. The latter compound may then be deprotected by known methods to provide an octahydropyrrolo[2,3,c]pyridine derivative of Formula (I).

Scheme 1

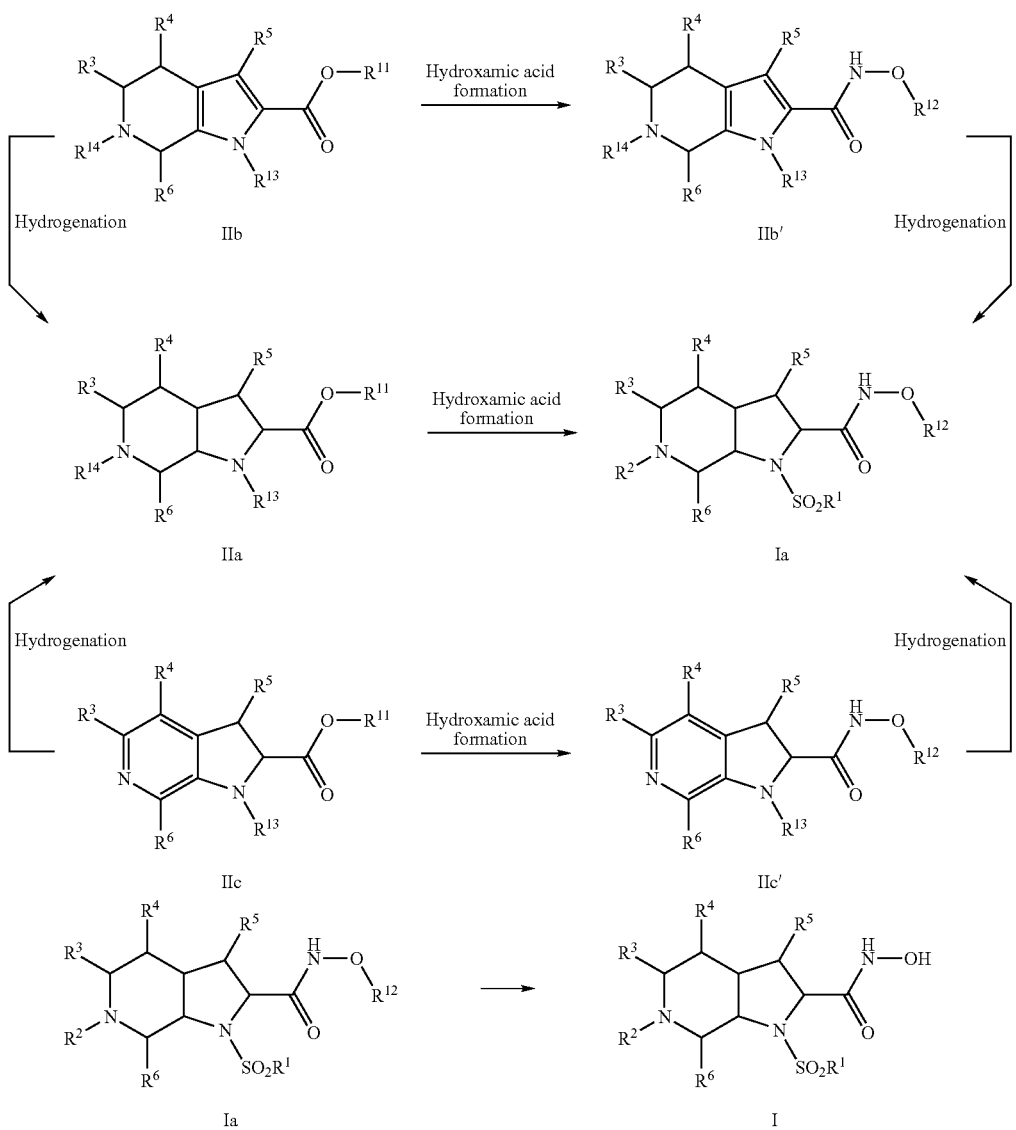

Alternatively, the octahydropyrrolo[2,3,c]pyridine of Formula (I) can be prepared according to Scheme 1 by converting the carboxylic esters of formula (IIa)—where $R^{11}$ is $C_1$-$C_6$ alkyl, $R^{13}$ is H, —$SO_2R^1$ or a protective group (such as Boc, Fmoc, Benzyloxycarbonyl, or benzyl); $R^{14}$ is H, $R^2$ or a protective group (such as Boc, Fmoc, Benzyloxycarbonyl, or benzyl)—into the corresponding protected derivative of formula (Ia), wherein $R^{12}$ is a t-butyl, benzyl, trialkylsilyl or other suitable protecting group by reacting the carboxylic esters of formula (IIa) with trimethylaluminium and a protected hydroxylamine derivative $H_2NO$—$R^{12}$. The latter compound may then carboxylic esters of formula (IIa) be deprotected by known methods to provide to provide an octahydropyrrolo[2,3,c]pyridine derivative of Formula (I).

According another process, the octahydropyrrolo[2,3,c] pyridine of Formula (I) can be prepared by converting the carboxylic acids or esters of formulae (IIb) or (IIc)—where $R^{11}$ is H or $C_1$-$C_6$ alkyl, $R^{13}$ is H, —$SO_2R^1$ or a protective group such as Boc, Fmoc, Benzyloxycarbonyl, or benzyl; $R^{14}$ is H, $R^2$ or a protective group such as Boc, Fmoc, Benzyloxycarbonyl, or benzyl—into the corresponding hydroxamic acids (IIb') or (IIc') respectively following a procedure as mentioned above, followed by the hydrogenation of the pyrrole ring of the structure of formula (IIb') or of the pyridine ring of the structures of formula (IIc') by their reaction with a suitable catalyst such as Pd/C, Rh/Al$_2$O$_3$ or the Wilkinson's catalyst.

The carboxylic acids or esters of formula (IIa), precursors of the octahydropyrrolo[2,3,c]pyridine of Formula (I), may be prepared by the hydrogenation of the insaturations of the pyrrole ring of the structure of formula (IIb) or of the pyridine ring of the structures of formula (IIc) with a suitable catalyst to give carboxylic acids or esters of formula (IIa).

Carboxylic acids or esters of formulae II (a-c) can be prepared according to Scheme 2 below by reduction of a compound of formula (III) with a suitable catalyst such as Pd/C, Rh/Al$_2$O$_3$ or the Wilkinson's catalyst.

Scheme 2

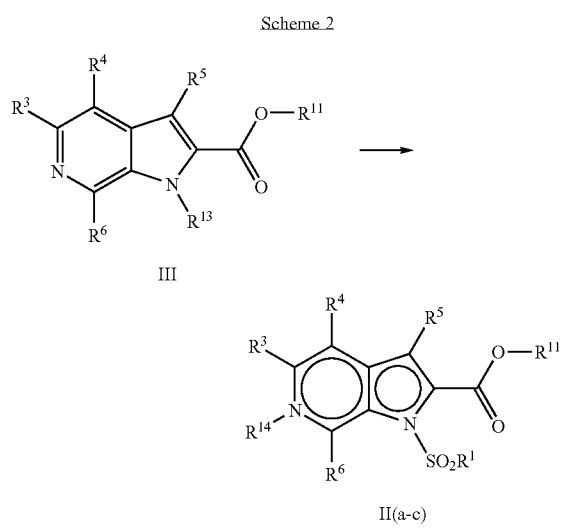

Compounds of the invention of Formula (I) and their precursors of formulae (IIa), (IIb), (IIc), (IIb'), (IIc') and (III) can be prepared by modifying or introducing the substituents $R^2$ and —$SO_2R^1$ at any stage of the synthesis, wherein $R^2$ may be H, optionally substituted $C_1$-$C_6$ alkyl, optionally substituted $C_2$-$C_6$ alkenyl, optionally substituted $C_2$-$C_6$ alkynyl, optionally substituted acyl, optionally substituted acyl $C_1$-$C_6$-alkyl, such as a —$(CH_2)_nC(O)$—$(CH_2)_m$—$R^8$ moiety, optionally substituted alkoxycarbonyl such as a —C(O)—O—$R^{10}$ moiety, optionally substituted sulfonyl, such as a —$SO_2$—$R^{15}$ moiety, optionally substituted aminocarbonyl or optionally substituted $C_1$-$C_6$ alkyl aminocarbonyl moiety, including a —$(CH2)_nC(O)NR^8R^9$ moiety; $R^1$, $R^8$, $R^9$, $R^{10}$, $R^{15}$, m and n are defined above.

The introduction of $R^2$ or $R^{14}$ onto precursors of formulae (I), (IIa), (IIb), (IIc), (IIb'), (IIc') and (III) when $R^2$ or $R^{14}$ of is an acyl moiety —$COR^8$ or a sulfonyl moiety —$SO_2R^{15}$ can be preformed from the corresponding amines of formulae (I), (IIa), (IIb), (IIc), (IIb'), (IIc') and (III) where $R^2$ or $R^{14}$ is H. The processes referred above consist in preparing an amide bond from an amine and a carboxylic acid or carboxylic acid derivative (e.g. acid chloride) or in preparing a sulfonamide bond from an amine and a sulfonic acid derivatives (e.g. sulfonyl chloride) under conditions and methods well known to those skilled in the art.

The introduction of $R^2$ or $R^{14}$ onto precursors of formulae (I), (IIa), (IIb), (IIc), (IIb'), (IIc') and (III) when $R^2$ or $R^{14}$ of is an alkyl group, —$(CH_2)nC(O)NR^8R^9$ or —$(CH2)_nC(O)$—$(CH_2)_m$—$R^8$ wherein $R^8$ and $R^9$ are defined as above and wherein n is not 0, can be preformed from the corresponding amine and an alkylating agent (i.e. alkyl halides) or from the corresponding amine, a carbonyl compound (i.e. aldehydes or ketones) and a reducing agent (such as $NaBH(OAc)_3$, $NABH_3CN$, $NaBH_4$ or hydrogen with an appropriate catalyst).

The introduction of $R^2$ onto precursors of Formulae (I), (IIa), (IIb), (IIc), (IIb'), (IIc') and (III) when $R^2$ is a carboxamide moiety —$C(O)NR^8R^9$, can be preformed from the corresponding amines of Formulae (I), (IIa), (IIb), (IIc), (IIb'), (IIc') and (III) where $R^2$ is H using conditions and methods well known to those skilled in the art to prepare an urea from an amine and a isocyanate derivative or from two different amines and phosgene or phosgene equivalent (e.g. triphosgene).

According to a further general process, compounds of Formula (I) can be converted to alternative compounds of Formula (I), employing suitable interconversion techniques well known by a person skilled in the art.

If the above set of general synthetic methods are not applicable to obtain compounds according to Formula (I) and/or necessary intermediates for the synthesis of compounds of Formula (I), suitable methods of preparation known by a person skilled in the art should be used. In general, the synthesis pathways for any individual compound of Formula (I) will depend on the specific substitutents of each molecule and upon the ready availability of intermediates necessary; again such factors being appreciated by those of ordinary skill in the art. For all the protection and deprotection methods, see Philip J. Kocienski, in "*Protecting Groups*", Georg Thieme Verlag Stuttgart, New York, 1994 and, Theodora W. Greene and Peter G. M. Wuts in "*Protective Groups in Organic Synthesis*", Wiley Interscience, 3$^{rd}$ Edition 1999. Those skilled in the art will recognize that certain reactions are best carried out when potentially reactive functionality on the molecule is masked or protected, thus avoiding side reactions and/or increasing the yield of the reaction. Examples of protecting group moieties may be found in Philip J. Kocienski, 1994 above and in Greene et al., 1999, above. The need and choice of protecting groups for a particular reaction is known to those skilled in the art and depends on the nature of the functional group to be protected (hydroxy, amino, carboxy, etc.), the structure and the stability of the molecule of which the substituent is part of the reaction conditions.

Compounds of this invention can be isolated in association with solvent molecules by crystallization from evaporation of an appropriate solvent. The pharmaceutically acceptable acid addition salts of the compounds of Formula (I), which contain a basic center, may be prepared in a conventional manner. For example, a solution of the free base may be treated with a suitable acid, either neat or in a suitable solution, and the resulting salt isolated either by filtration or by evaporation under vacuum of the reaction solvent. Pharmaceutically acceptable base addition salts may be obtained in an analogous manner by treating a solution of compound of Formula (I) with a suitable base. Both types of salts may be formed or interconverted using ion-exchange resin techniques.

In the following the present invention shall be illustrated by means of some examples, which are not construed to be viewed as limiting the scope of the invention.

The following reagents/resins commercially available were used:

Ethyl 1H-pyrrolo[2,3-c]pyridine-2-carboxylate (following the preparation of Fisher et al., 1969, *J. Heterocycl. Chem.*, 6, 775-776); Di-tertbutyl dicarbonate (from Aldrich); N-methylmorpholine (from Fluka); Isobutyl chloroformate (from Aldrich); O-benzylhydroxylamine (from Lancaster); 3-methylbutanoyl chloride (from Aldrich); Propylamine (from Fluka); p-anisoyl chloride (from Aldrich); 3-cyclopentyl-propionyl chloride (from Aldrich); 4-methoxy-benzenesulfonyl chloride (from Fluka); 2-methoxy ethyl chloroformate (from Aldrich); Lauroyl chloride (from Aldrich); Cyclopentanecarbonyl chloride (from Aldrich); 3-phenyl-propionyl chloride (from Aldrich); Methanesulfonyl chloride (from Fluka); 4-(pyridin-4-yloxy)-benzenesulfonyl hydrochloride (from Array); 4-biphenylcarbonyl chloride (from Aldrich); 2-chloro-N,N-diethyl acetamide (from Aldrich); t-butylammonium iodide (from Aldrich); (N-chloroacetyl)ethylamine (from Aldrich); O-benzylhydroxylamine hydrochloride (from Aldrich); Phenyl isocyanate (from Aldrich); Morpholinomethyl polystyrene resin (from Novabiochem); Aminomethyl polystyrene (from PolymerLab); Carbonate resin (from Argonaut).

Example 1

Preparation of rel-(2S,3aS,7aR)-6-benzoyl-N-hydroxy-1-[(4-methoxy phenyl)sulfonyl]octahydro-1H-pyrrolo[2,3-c]pyridine-2-carboxamide (1)

Step a) Formation of 1-tert-butyl 2-ethyl 1H-pyrrolo[2,3-c]pyridine-1,2-dicarboxylate (Compound of Formula IIc wherein $R^{11}$ is ethyl, $R^{13}$ is Boc)

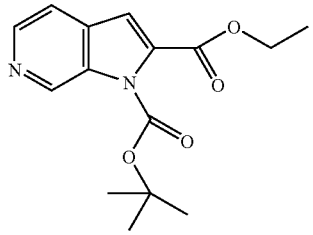

To a solution ethyl 1H-pyrrolo[2,3-c]pyridine-2-carboxylate (Fisher et al., 1969, above) (480 mg, 2.52 mmol) in DMF (12 mL) at 0° C. was added 60% sodium hydride (121 mg, 3.02 mmol, 1.2 eq.). The reaction mixture was stirred at 0° C. for 30 min and di-tertbutyl dicarbonate solution (1 M in DMF, 659 mg, 3.02 mmol, 1.2 eq.) was added. The reaction mixture was stirred at rt for 24 hours and was partitioned between water and DCM. The combined organic layers were dried over $Na_2SO_4$ and concentrated. Remaining DMF was evaporated and resulting residue was purified by column chromatography (c-Hex/EtOAc gradient: 80/20 to 30/70 in 25 minutes) to give the title compound (656 mg, 90%). HPLC purity: 99%. $^1$H NMR (300 MHz, $CDCl_3$) δ 1.41 (t, 3H, J=7.1 Hz), 1.67 (s, 9H), 4.42 (q, 2H, J=7.1 Hz), 7.01 (s, 1H), 7.55 (d, 1H, J=4.9 Hz), 8.47 (br s, 1H), 9.41 (br s, 1H). $R_f$(c-Hex/EtOAc 70/30)=0.2.

Step b) Formation of 1-tert-butyl 2-ethyl rel-(2S,3aS, 7aR)-octahydro-1H-pyrrolo[2,3-c]pyridine-1,2-dicarboxylate (Compound of Formula IIa wherein $R^{11}$ is ethyl, $R^{13}$ is Boc, $R^3$, $R^4$, $R^5$, $R^6$ and $R^{14}$ are H)

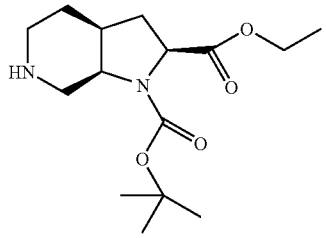

1-tert-butyl 2-ethyl 1H-pyrrolo[2,3-c]pyridine-1,2-dicarboxylate (290 mg, 1 mmol) obtained under step a) was dissolved in THF (20 mL) and 5% $Rh/Al_2O_3$ (411 mg, 0.2 eq.) was added. The suspension was hydrogenated under 25 Bars at rt for 5 days then under 45 Bars at 50° C. for 1 day. The catalyst was removed by filtration through a Celite pad, was washed with THF and the filtrate was evaporated. Column chromatography (EtOAc/TEA 90/10) followed by removing of remaining catalyst with active charcoal in EtOAc afforded the title compound (210 mg, 70%).

$M^+$(LC-MS (ESI)): 299. $^1$H NMR (300 MHz, $CDCl_3$) δ 1.27 (m, 3H), 1.41 (d, 9H, J=12.6 Hz), 1.62 (d, 1H, J=13.7 Hz), 1.78-1.95 (m, 1H), 1.95-2.10 (m, 2H), 2.10-2.23 (m, 1H), 2.32-2.50 (m, 1H), 2.64 (dq, 2H, J1=3.0 Hz, J2=12.5 Hz), 2.83 (d d, 1H, J1=5.1 Hz, J2=12.6 Hz), 3.31 (dq, 1H, J1=5.7 Hz, J2=32.2 Hz), 3.78-3.97 (m, 1H), 4.08-4.30 (m, 3H). $R_f$(EtOAc/TEA 90/10)=0.2.

Step c) Formation of 1-tert-butyl 2-ethyl rel-(2S,3aS, 7aR)-6-benzoyloctahydro-1H-pyrrolo[2,3-c]pyridine-1,2-dicarboxylate (Compound of Formula IIa wherein $R^{11}$ is ethyl, $R^{13}$ is Boc, $R^{14}$ is —C(O)Ph, $R^3$, $R^4$, $R^5$ and $R^6$ are H)

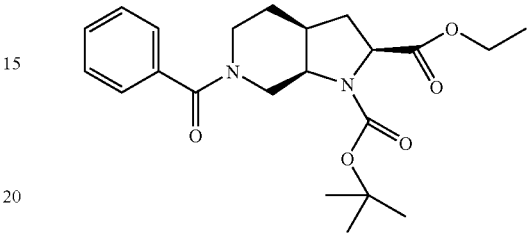

A solution of 1-tert-butyl 2-ethyl rel-(2S,3aS,7aR)-octahydro-1H-pyrrolo[2,3-c]pyridine-1,2-dicarboxylate (160 mg, 0.54 mmol) obtained under step b) and morpholinomethyl polystyrene resin (318 mg, 1.08 mmol, 2 eq.) in DCM (3.18 mL) was cooled to 0° C. and stirred for 10 minutes. Benzoyl chloride (75 μL, 0.65 mmol, 1.2 eq.) was added and the reaction was stirred at rt for 14 hours. Aminomethyl polystyrene (280 mg, 0.54 mmol, 1 eq.) was added and the reaction mixture was stirred at rt for 2 hours. Resins were removed by filtration, washed with DCM and EtOAc and the filtrate was evaporated to give the title compound (196 mg, 91%). HPLC purity: 89%. $M^+$(LC-MS (ESI)): 403. $^1$H NMR (300 MHz, $CDCl_3$) δ 1.13-1.38 (m, 12H), 1.71 (d, 1H, J=12.8 Hz), 1.83-2.14 (m, 2H), 2.19-2.32 (m, 1H), 2.41-2.57 (m, 1H), 2.80-3.20 (m, 2H), 3.67-3.81 (m, 1H), 3.90-4.03 (m, 1H), 4.03-4.28 (m, 3H), 4.38 (d, 1H, J=12.4 Hz), 7.37 (s, 5H). $R_f$ (c-Hex/EtOAc 50/50)=0.2.

Step d) Formation of ethyl rel-(2S,3aS,7aR)-6-benzoyloctahydro-1H-pyrrolo[2,3-c]pyridine-2-carboxylate (Compound of Formula IIa wherein $R^{11}$ is ethyl, $R^{13}$ is H, $R^{14}$ is —C(O)Ph, $R^3$, $R^4$, $R^5$, $R^6$ and $R^6$ are H)

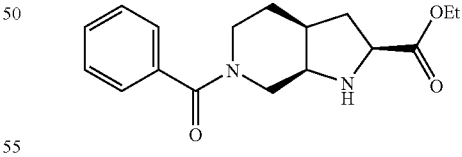

1-tert-butyl 2-ethyl rel-(2S,3aS,7aR)-6-benzoyloctahydro-1H-pyrrolo[2,3-c]pyridine-1,2-dicarboxylate (196 mg, 0.49 mmol) obtained under step c) was dissolved in DCM (5 mL), HCl solution (4 M in dioxane, 2.45 mL, 20 eq.) was added and the reaction mixture was stirred at rt for 8 hours. The reaction mixture was partitioned between saturated aqueous solution of $NaHCO_3$ and DCM. The combined organic layers were dried over $Na_2SO_4$ and concentrated to afford the title compound (147 mg, 100%).

$M^+$(LC-MS (ESI)): 303. $^1$H NMR (300 MHz, $CDCl_3$) δ 1.25 (t, 3H, J=7.2 Hz), 1.42-1.60 (m, 1H), 1.69-1.83 (m, 1H), 2.16-2.30 (m, 2H), 2.39 (s, 1H), 3.00-3.74 (m, 5H), 3.74-3.88 (m, 1H), 4.17 (q, 2H, J=7.2 Hz), 7.35 (m, 5H). $R_f$ (EtOAc/TEA 90/10)=0.5.

Step e) Formation of ethyl rel-(2S,3aS,7aR)-6-benzoyl-1-[(4-methoxyphenyl)sulfonyl]octahydro-1H-pyrrolo[2,3-c]pyridine-2-carboxylate (Compound of Formula IIa wherein $R^{11}$ is ethyl, $R^{13}$ is —$SO_2$-4-methoxyphenyl, $R^{14}$ is —C(O)Ph and $R^3$, $R^4$, $R^5$ and $R^6$ are H)

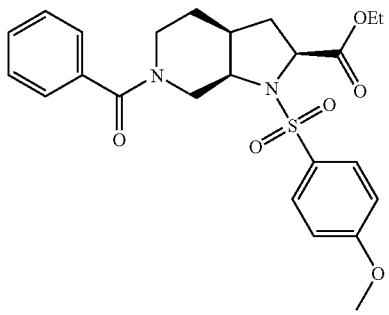

A solution of ethyl rel-(2S,3aS,7aR)-6-benzoyloctahydro-1H-pyrrolo[2,3-c]pyridine-2-carboxylate (147 mg, 0.49 mmol) obtained under step d) and morpholinomethyl polystyrene resin (288 mg, 0.98 mmol, 2 eq.) in THF (2.88 mL) was cooled to 0° C. and stirred for 10 minutes. 4-methoxybenzenesulfonyl chloride (122 mg, 0.59 mmol, 1.2 eq.) was added and the reaction was stirred at rt for 14 hours. Aminomethyl polystyrene (381 mg, 0.49 mmol, 1 eq.) was added and the reaction mixture was stirred at rt for 6 hours. Resins were removed by filtration, washed with DCM and EtOAc and the filtrate was evaporated to give the title compound (203 mg, 88%). HPLC purity: 95%. M⁺(LC-MS (ESI)): 473. ¹H NMR (300 MHz, CDCl₃) δ 1.27 (t, 3H, J=7.2 Hz), 1.56-1.74 (m, 1H), 1.78-1.85 (m, 2H), 1.99-2.30 (m, 3H), 2.82-3.22 (m, 2H), 3.65-3.76 (m, 2H), 3.82 (s, 3H), 4.14-4.32 (m, 3H), 6.78-7.02 (m, 2H), 7.29-7.43 (m, 5H), 7.59-7.90 (m, 2H). $R_f$ (c-Hex/EtOAc 50/50)=0.1.

Step f) Formation of rel-(2S,3aS,7aR)-6-benzoyl-1-[(4-methoxyphenyl)sulfonyl]octahydro-1H-pyrrolo[2,3-c]pyridine-2-carboxylic acid (Compound of Formula IIa wherein $R^{11}$ is H, $R^{13}$ is —$SO_2$-4-methoxyphenyl, $R^{14}$ is —C(O)Ph, and $R^3$, $R^4$, $R^5$ and $R^6$ are H)

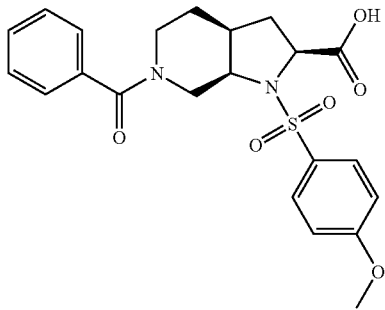

To a solution of ethyl rel-(2S,3aS,7aR)-6-benzoyl-1-[(4-methoxyphenyl)sulfonyl]octahydro-1H-pyrrolo[2,3-c]pyridine-2-carboxylate (203 mg, 0.43 mmol) obtained under step e) in ethanol (4 mL) at room temperature was added sodium hydroxide solution (103 mg, 2.58 mmol, 6 eq., in 4 mL H₂O). The reaction mixture was stirred at rt for 3 hours and partitioned between 1 N HCl and DCM. The combined organic layers were washed with brine, dried over Na₂SO₄ and concentrated to give the title compound (101 mg, 53%). HPLC purity: 96%. M⁺(LC-MS (ESI)): 445, M⁻(LC-MS (ESI)): 443

¹H NMR (300 MHz, CDCl₃) δ 1.49-2.01 (m, 2H), 2.05-2.32 (m, 3H), 2.89-3.31 (m, 2H), 3.51-3.81 (m, 2H), 3.85 (s, 3H), 4.12-4.62 (m, 2H), 6.80-7.09 (m, 2H), 7.30-7.48 (m, 5H), 7.59-7.99 (m, 2H). $R_f$ (EtOAc/EtOH 80/20)=0.1.

Step g) Formation of rel-(2S,3aS,7aR)-6-benzoyl-N-(benzyloxy)-1-[(4-methoxyphenyl)sulfonyl]octahydro-1H-pyrrolo[2,3-c]pyridine-2-carboxamide (Compound of Formula Ia wherein $R^{12}$ is —$CH_2$-Ph; $R^{13}$ is —$SO_2$-4-methoxyphenyl, $R^{14}$ is —C(O)Ph and $R^3$, $R^4$, $R^5$ and $R^6$ are H)

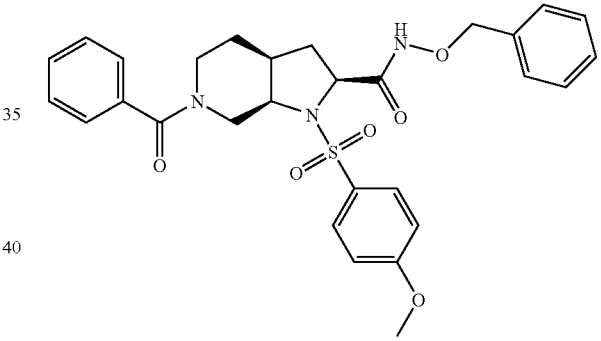

A solution of rel-(2S,3aS,7aR)-6-benzoyl-1-[(4-methoxyphenyl)sulfonyl]octahydro-1H-pyrrolo[2,3-c]pyridine-2-carboxylic acid (63 mg, 0.14 mmol) obtained under step f) and N-methylmorpholine (18 μL, 0.17 mmol, 1.2 eq.) in THF (1 mL) was cooled to −15° C. and isobutyl chloroformate (19 μL, 0.15 mmol, 1.1 eq.) was added. The reaction was kept under these conditions and stirred for 30 minutes. O-benzylhydroxylamine (21 mg, 0.17 mmol, 1.2 eq) was added. The reaction mixture was stirred at rt for 2 hours and was partitioned between water and EtOAc. The combined organic layers were dried over Na₂SO₄ and concentrated. Column chromatography (c-Hex/EtOAc 20/80) afforded the title compound (54 mg, 69%). HPLC purity: 95%. M⁺(LC-MS (ESI)): 550, M⁻(LC-MS (ESI)): 548. ¹H NMR (300 MHz, CDCl₃) δ 1.38-1.83 (m, 2H), 1.96-2.10 (m, 2H), 2.10-2.28 (m, 1H), 2.88-3.18 (m, 2H), 3.25-3.79 (m, 2H), 3.85 (s, 3H), 4.01-4.21 (m, 2H), 4.80-5.04 (m, 2H), 6.93 (br s, 2H), 7.25-7.50 (m, 10H), 7.54-7.90 (m, 2H), 9.10-9.97 (m, 1H). $R_f$ (c-Hex/EtOAc 20/80)=0.2.

Step h) Formation of rel-(2S,3aS,7aR)-6-benzoyl-N-hydroxy-1-[(4-methoxyphenyl)sulfonyl]octahydro-1H-pyrrolo[2,3-c]pyridine-2-carboxamide (1) (Compound of Formula (I) wherein $R^1$ is 4-methoxyphenyl, $R^2$ is —C(O)phenyl, $R^3$, $R^4$, $R^5$ and $R^6$ are H)

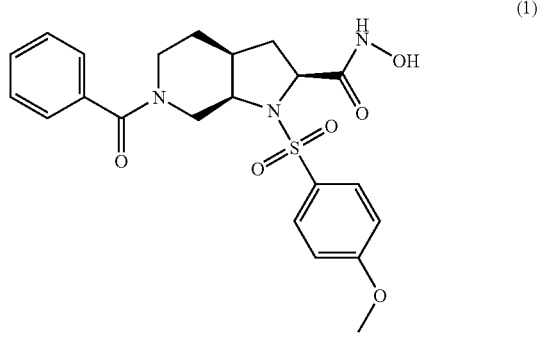

(1)

rel-(2S,3aS,7aR)-6-benzoyl-N-(benzyloxy)-1-[(4-methoxyphenyl)sulfonyl]octahydro-1H-pyrrolo[2,3-c]pyridine-2-carboxamide (50 mg, 0.09 mmol) obtained under step g) was dissolved in ethanol (1 mL) and 10% Pd/C (20 mg, 0.2 eq.) was added. The suspension was hydrogenated (1 Bar) at rt for 5 hours. The catalyst was removed by filtration through a Celite pad, washed with ethanol and the filtrate was evaporated to give the title compound (1) (41 mg, 98%). HPLC purity: 100%. $M^+$(LC-MS (ESI)): 460, $M^-$(LC-MS (ESI)): 458

$^1$H NMR (300 MHz, CDCl$_3$) δ 1.40-1.87 (m, 2H), 1.89-2.14 (m, 2H), 2.16-2.39 (m, 1H), 3.07-3.54 (m, 2H), 3.56-3.81 (m, 2H), 3.86 (s, 3H), 3.94-4.39 (m, 2H), 6.98 (br s, 2H), 7.40 (s, 5H), 7.59-7.99 (m, 2H), 9.00-10.51 (br s, 1H). $R_f$ (EtOAc)=0.1.

Example 2

Preparation of rel-(2S,3aS,7aR)-6-acetyl-N-hydroxy-1-[(4-methoxy phenyl)sulfonyl]octahydro-1H-pyrrolo[2,3-c]pyridine-2-carboxamide (2)

Step a) Formation of ethyl 4,5,6,7-tetrahydro-1H-pyrrolo[2,3-c]pyridine-2-carboxylate (Compound of Formula IIb wherein $R^{11}$ is ethyl, $R^3$, $R^4$, $R^5$, $R^6$, $R^{13}$ and $R^{14}$ are H)

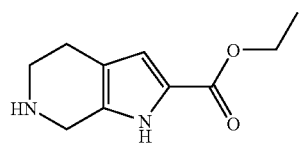

Ethyl 1H-pyrrolo[2,3-c]pyridine-2-carboxylate (4.225 g, 22.21 mmol) was dissolved in acetic acid (150 mL) and 5% Rh/Al$_2$O$_3$ (9.144 g, 0.2 eq.) was added. The suspension was hydrogenated (45 Bars) at rt for 4 days then at 50° C. for 7 days. The catalyst was removed by filtration through a Celite pad, was washed with acetic acid and the filtrate was evaporated. The residue was dissolved in DCM, washed with saturated aqueous solution of NaHCO$_3$ and aqueous phases were extracted with DCM. The combined organic layers were washed with brine, dried over Na$_2$SO$_4$ and concentrated to give the title compound (4.183 g, 97%). HPLC purity: 92%. $M^+$(LC-MS (ESI)): 195, $M^-$(LC-MS (ESI)): 193

$^1$H NMR (300 MHz, CDCl$_3$) δ 1.31 (t, 3H, J=7.1 Hz), 2.69 (t, 2H, J=5.6 Hz), 3.17 (t, 2H, J=6.0 Hz), 4.00 (s, 2H), 4.25 (q, 2H, J=7.1 Hz), 6.59 (s, 1H), 8.38 (br s, 1H).

Step b) Formation of ethyl 6-acetyl-4,5,6,7-tetrahydro-1H-pyrrolo[2,3-c]pyridine-2-carboxylate (Compound of Formula IIb wherein $R^{11}$ is ethyl, $R^3$, $R^4$, $R^5$, $R^6$, $R^{13}$ are H, $R^{14}$ is Ac)

To a solution of ethyl 4,5,6,7-tetrahydro-1H-pyrrolo[2,3-c]pyridine-2-carboxylate obtained under step a) (2.000 g, 10.30 mmol) in DCM (64 mL) at 0° C. were added TEA (2.14 mL, 15.45 mmol, 1.5 eq.) and acetic anhydride (1.27 mL, 13.39 mmol, 1.3 eq.). The reaction was stirred at rt for 2 hours. The reaction mixture was concentrated and the residue was partitioned between saturated aq solution of NaHCO$_3$ and DCM. The combined organic layers were dried over Na$_2$SO$_4$ and concentrated to afford the title compound (1.900 g, 78%). HPLC purity: 97%. $M^+$(LC-MS (ESI)): 237, $M^-$(LC-MS (ESI)): 235

$^1$H NMR (300 MHz, CDCl$_3$) δ 1.34 (t, 3H, J=7.2 Hz), 2.17 (d, 3H, J=8.3 Hz), 2.63 (d t, 2H, J1=5.7 Hz, J2=17.7 Hz), 3.74 (dt, 2H, J1=5.6 Hz, J2=51.6 Hz), 4.30 (q, 2H, J=7.2 Hz), 4.62 (d, 2H, J=16.2 Hz), 6.70 (d, 1H, J=2.3 Hz), 8.89 (br s, 1H).

Step c) Formation of ethyl 6-acetyl-1-[(4-methoxyphenyl)sulfonyl]-4,5,6,7-tetrahydro-1H-pyrrolo[2,3-c]pyridine-2-carboxylate (Compound of Formula IIb wherein $R^{11}$ is ethyl, $R^{13}$ is —SO$_2$-4-methoxyphenyl, $R^3$, $R^4$, $R^5$, $R^6$ are H and $R^{14}$ is Ac)

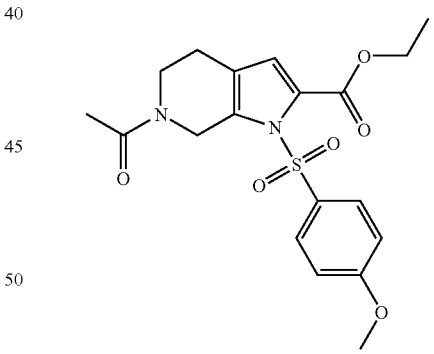

To a solution of ethyl 6-acetyl-4,5,6,7-tetrahydro-1H-pyrrolo[2,3-c]pyridine-2-carboxylate obtained under step b) (1.800 g, 7.62 mmol) in DMF (36 mL) at 0° C. was added 60% sodium hydride (366 mg, 9.14 mmol, 1.2 eq.). The reaction mixture was stirred at 0° C. for 30 min and 4-methoxybenzenesulfonyl chloride (1.889 g, 9.14 mmol, 1.2 eq.) was added. The reaction mixture was stirred at rt for 2 hours and was partitioned between brine and DCM. The combined organic layers were dried over Na$_2$SO$_4$ and concentrated. Purification on SPE NH$_2$ column (from Isolute, elution in DCM) then on silica column (CHCl$_3$) afforded the title compound (1.730 g, 56%). HPLC purity 95%. $M^+$(LC-MS (ESI)): 407, $M^-$(LC-MS (ESI)): 405. $^1$H NMR (300 MHz, CDCl$_3$) δ 1.30 (t, 3H, J=7.2 Hz), 2.17 (s, 3H), 2.50-2.63 (m, 2H), 3.72 (m, 2H), 3.86

(s, 3H), 4.25 (q, 2H, J=7.2 Hz), 4.92 (d, 2H, J=47.4 Hz), 6.73 (m, 1H), 6.97-7.05 (m, 2H), 7.93-8.15 (m, 2H). R$_f$ (CHCl$_3$/MeOH 98/02)=0.4.

Step d) Formation of ethyl rel-(2S,3aS,7aR)-6-acetyl-1-[(4-methoxyphenyl)sulfonyl]octahydro-1H-pyrrolo[2,3-c]pyridine-2-carboxylate (Compound of Formula IIa wherein R$^{11}$ is ethyl, R$^{13}$ is —SO$_2$-4-methoxyphenyl, R$^3$, R$^4$, R$^5$, R$^6$ are H and R$^{14}$ is Ac)

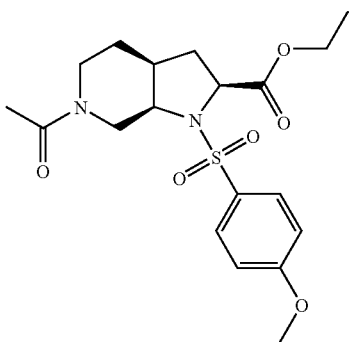

Ethyl-6-acetyl-1-[(4-methoxyphenyl)sulfonyl]-4,5,6,7-tetrahydro-1H-pyrrolo[2,3-c]pyridine-2-carboxylate obtained under step c) (200 mg, 0.49 mmol) was dissolved in THF (6 mL) and 10% Pd/C (210 mg, 0.4 eq.) was added. The suspension was hydrogenated (40 Bars) at 90° C. for 48 hours. The catalyst was removed by filtration through a Celite pad, was washed with THF and the filtrate was evaporated. Column chromatography (EtOAc) afforded the title compound (147 mg, 73%). HPLC purity: 95%. M$^+$(LC-MS (ESI)): 411. $^1$H NMR (300 MHz, CDCl$_3$) δ 1.31 (t, 3H, J=7.2 Hz), 1.55 (d, 1H, J=14.7 Hz), 1.65-1.83 (m, 1H), 2.11 (s, 3H), 2.94 (dt, 1H, J1=3.8 Hz, J2=10.6 Hz), 3.45 (dd, 1H, J1=8.6 Hz, J2=13.5 Hz), 3.61-3.81 (m, 2H), 3.87 (s, 3H), 3.98 (d, 1H, J=13.2 Hz), 4.23 (q, 2H, J=7.2 Hz), 7.00 (d, 2H, J=8.6 Hz), 7.81 (d, 2H, J=9.0 Hz). R$_f$(EtOAc)=0.2.

Step e) Formation of rel-(2S,3aS,7aR)-6-acetyl-1-[(4-methoxyphenyl)sulfonyl]octahydro-1H-pyrrolo[2,3-c]pyridine-2-carboxylic acid (Compound of Formula IIb wherein R$^{11}$ is H, R$^{13}$ is —SO$_2$-4-methoxyphenyl, R$^3$, R$^4$, R$^5$, R$^6$ are H and R$^{14}$ is Ac)

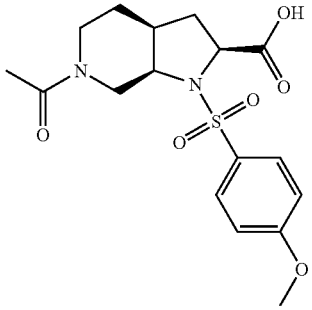

To a solution of ethyl rel-(2S,3aS,7aR)-6-acetyl-1-[(4-methoxyphenyl)sulfonyl]octahydro-1H-pyrrolo[2,3-c]pyridine-2-carboxylate obtained under step d) (82 mg, 0.20 mmol) in ethanol (2 mL) at rt was added sodium hydroxide solution (48 mg, 1.2 mmol, 6 eq., in 2 mL H$_2$O). The reaction mixture was stirred at rt for 14 hours and partitioned between 1 N HCl and EtOAc. The combined organic layers were washed with brine, dried over Na$_2$SO$_4$ and concentrated to give the title compound (39 mg, 51%). HPLC purity: 92%. M$^+$(LC-MS (ESI)): 383, M$^-$(LC-MS (ESI)): 381. $^1$H NMR (300 MHz, DMSO-d$_6$) δ 1.38-1.58 (m, 2H), 1.60-1.90 (m, 2H), 1.99 (d, 3H, J=19.6 Hz), 2.05-2.23 (m, 1H), 3.00 (dt, 1H, J1=10.9 Hz, J2=63.3 Hz), 3.42-3.78 (m, 3H), 3.85 (d, 3H, J=1.1 Hz), 3.87-4.07 (m, 2H), 7.14 (dd, 2H, J1=2.6 Hz, J2=9.0 Hz), 7.81 (dd, 2H, J1=9.0 Hz, J2=15.4 Hz), 12.70 (br s, 1H).

Step f) Formation of rel-(2S,3aS,7aR)-6-acetyl-N-(benzyloxy)-1-[(4-methoxyphenyl)sulfonyl]octahydro-1H-pyrrolo[2,3-c]pyridine-2-carboxamide (Compound of Formula Ia wherein R$^{12}$ is —CH$_2$-Ph, R$^{13}$ is —SO$_2$-4-methoxyphenyl, R$^3$, R$^4$, R$^5$, R$^6$ are H and R$^{14}$ is Ac)

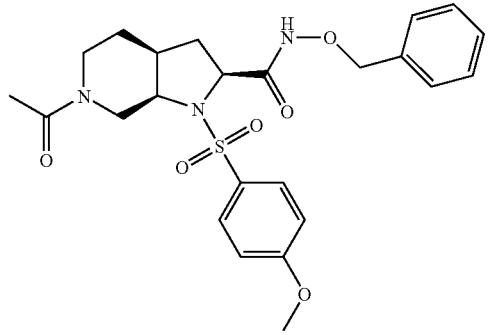

A solution of rel-(2S,3aS,7aR)-6-acetyl-1-[(4-methoxyphenyl)sulfonyl]octahydro-1H-pyrrolo[2,3-c]pyridine-2-carboxylic acid (36 mg, 0.09 mmol) obtained under step e) and N-methylmorpholine (12 μL, 0.11 mmol, 1.2 eq.) in THF (2 mL) was cooled to −15° C. and isobutyl chloroformate (13 μL, 0.10 mmol, 1.1 eq.) was added. The reaction was kept under these conditions and stirred for 30 minutes. O-benzylhydroxylamine (14 mg, 0.11 mmol, 1.2 eq.) was added. The reaction mixture was stirred at rt for 2 hours and was partitioned between brine and DCM. The combined organic layers were dried over Na$_2$SO$_4$ and concentrated. Column chromatography (EtOAc) afforded the title compound (13 mg, 28%). M$^+$(LC-MS (ESI)): 488, M$^-$(LC-MS (ESI)): 486. $^1$H NMR (300 MHz, CDCl$_3$) δ 1.39-1.51 (m, 1H), 1.54-1.71 (m, 1H), 1.72-2.00 (m, 2H), 2.09 (s, 3H), 2.12-2.26 (m, 1H), 2.89-3.11 (m, 1H), 3.13-3.28 (m, 1H), 3.51-3.67 (m, 2H), 3.68-3.81 (m, 1H), 3.88 (s, 3H), 3.96-4.05 (m, 1H), 4.84-5.04 (m, 2H), 7.01 (d, 2H, J=8.3 Hz), 7.30-7.42 (m, 3H), 7.46 (d, 2H, J=6.8 Hz), 7.74 (d, 2H, J=8.7 Hz), 9.31 (m, 1H). R$_f$(EtOAc)=0.1.

Step g) Formation of rel-(2S,3aS,7aR)-6-acetyl-N-hydroxy-1-[(4-methoxyphenyl)sulfonyl]octahydro-1H-pyrrolo[2,3-c]pyridine-2-carboxamid (2) (Compound of Formula (I) wherein $R^1$ is 4-methoxyphenyl; $R^2$ is Ac; $R^3$, $R^4$, $R^5$ and $R^6$ are H)

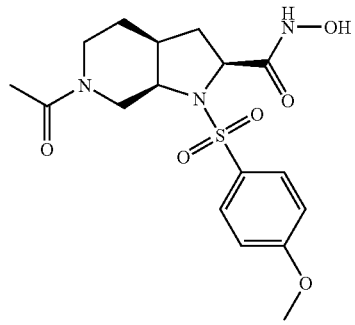

(2)

rel-(2S,3aS,7aR)-6-acetyl-N-(benzyloxy)-1-[(4-methoxyphenyl)sulfonyl]octahydro-1H-pyrrolo[2,3-c]pyridine-2-carboxamide (13 mg, 0.03 mmol) obtained under step f) was dissolved in ethanol (0.5 mL) and 10% Pd/C (7 mg, 0.2 eq.) was added. The suspension was hydrogenated (1 Bar) at rt for 14 hours. The catalyst was removed by filtration through a Celite pad, was washed with ethanol and the filtrate was evaporated to give the title compound (2) (8.4 mg, 79%). HPLC purity: 90%. M+(LC-MS (ESI)): 398, M−(LC-MS (ESI)): 396. $^1$H NMR (300 MHz, CDCl$_3$) δ 1.42-1.78 (m, 3H), 1.83-2.35 (m, 7H), 3.27-3.43 (m, 2H), 3.49-3.67 (m, 2H), 3.89 (s, 3H), 4.05-4.28 (m, 1H), 7.04 (d, 2H, J=7.9 Hz), 7.79 (d, 2H, J=8.3 Hz), 9.70 (m, 1H).

Example 3

Preparation of rel-(2S,3aS,7aR)—N-hydroxy-1-[(4-methoxyphenyl)sulfonyl]-6-(3-methylbutanoyl)octahydro-1H-pyrrolo[2,3-c]pyridine-2-carboxamide Step a) Formation of 1-tert-butyl 2-ethyl rel-(2S,3aS,7aR)-6-(3-methylbutanoyl)octahydro-1H-pyrrolo[2,3-c]pyridine-1,2-dicarboxylate (Compound of Formula IIa wherein $R^{11}$ is ethyl, $R^{13}$ is Boc, $R^3$, $R^4$, $R^5$, $R^6$ are H and $R^{14}$ is 3-methylbutanoyl)

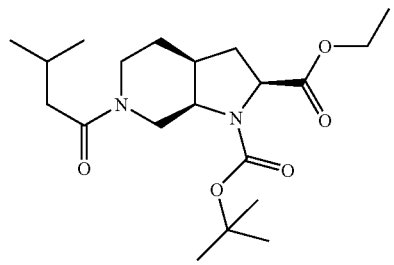

A solution was made of 1-tert-butyl 2-ethyl rel-(2S,3aS,7aR)-octahydro-1H-pyrrolo[2,3-c]pyridine-1,2-dicarboxylate obtained in Example 1 under step b) (100 mg, 0.335 mmol) in DCM (5 mL). Carbonate resin (268 mg, 0.67 mmol, 2.5 mmol/g loading) was then added and the suspension shaken. 3-methylbutanoyl chloride was then added (0.402 mmol) and the reaction shaken overnight before addition of propylamine on AMEBAII resin (251 mg, 0.201 mmol 0.8 mmol/g loading). The reaction was shaken for a further 4 hours before the resins were filtered off and washed with DCM (3×20 mL). The filtrates were collected and the solvent removed in vacuo to give the title compound. The product was used in the next step with no further purification.

Step b) Formation of ethyl rel-(2S,3aS,7aR)-6-(3-methylbutanoyl)octahydro-1H-pyrrolo[2,3-c]pyridine-2-carboxylate (Compound of Formula IIa wherein $R^{11}$ is ethyl, $R^3$, $R^4$, $R^6$, $R^{13}$ are H and $R^{14}$ is 3-methylbutanoyl)

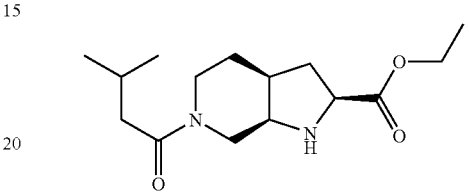

A solution was made of 1-tert-butyl 2-ethyl rel-(2S,3aS,7aR)-6-(3-methyl butanoyl)octahydro-1H-pyrrolo[2,3-c]pyridine-1,2-dicarboxylate obtained under step a) (0.335 mmol) in DCM (2.5 mL), to which TFA (2.5 mL) was added. The reaction was left to stir for 1 hour after which time it was checked by TLC (60% EtOAc in heptanes). If the reaction had not gone to completion after this time it was left stirring and checked after every additional ½. Generally this took 2 hours. When the reaction had gone to completion the TFA/DCM was removed in vacuo before being placed on a high vacuum line for 2 hours. The product was used in the next step with no further purification.

Step c) Formation of ethyl rel-(2S,3aS,7aR)-1-[(4-methoxyphenyl)sulfonyl]-6-(3-methyl butanoyl)octahydro-1H-pyrrolo[2,3-c]pyridine-2-carboxylate (Compound of Formula IIa wherein $R^{11}$ is ethyl, $R^{13}$ is —SO$_2$-4-methoxyphenyl, $R^3$, $R^4$, $R^5$, $R^6$ are H and $R^{14}$ is 3-methylbutanoyl)

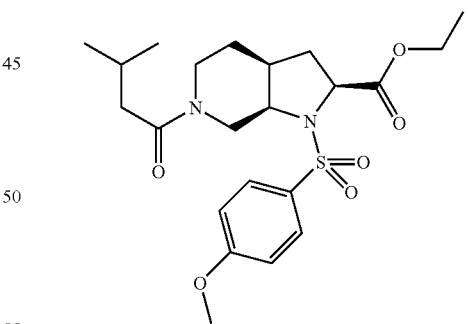

A solution was made of ethyl rel-(2S,3aS,7aR)-6-(3-methylbutanoyl)octahydro-1H-pyrrolo[2,3-c]pyridine-2-carboxylate obtained under step b) (0.335 mmol) in DCM (5 mL). Carbonate resin (268 mg, 0.67 mmol, 2.5 mmol/g loading) and p-anisoyl chloride was then added (0.402 mmol) and the reaction shaken overnight before addition of propylamine on AMEBAII resin (251 mg, 0.201 mmol 0.8 mmol/g loading). The reaction was shaken for a further 4 hours before the resins were filtered off and washed with DCM (3×20 mL). The filtrates were collected and the solvent removed in vacuo. The product was purified by silica gel chromatography.

Step d) Formation of rel-(2S,3aS,7aR)—N-(benzyloxy)-1-[(4-methoxyphenyl)sulfonyl]-6-(3-methylbutanoyl)octahydro-1H-pyrrolo[2,3-c]pyridine-2-carboxamide (Compound of Formula Ia wherein R$^{12}$ is —CH$_2$-Ph; R$^{13}$ is R$^{13}$ is —SO$_2$-4-methoxyphenyl, R$^3$, R$^4$, R$^5$, R$^6$ are H and R$^{14}$ is 3-methylbutanoyl)

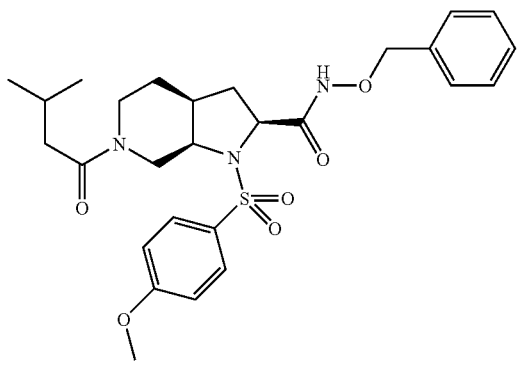

A solution was made containing ethyl rel-(2S,3aS,7aR)-1-[(4-methoxyphenyl)sulfonyl]-6-(3-methylbutanoyl)octahydro-1H-pyrrolo[2,3-c]pyridine-2-carboxylate obtained under step c) (0.3 mmol) in dry DCM (5 mL). O-benzylhydroxylamine hydrochloride was added (239 mg, 1.5 mmol) and the reaction vessel flushed with argon. The reaction was then stirred for 1 hour before trimethyl aluminium (0.750 mL, 1.5 mmol, 2.0 M in heptane) was cautiously added at room temperature. The reaction was then stirred for between 2 and 5 days depending on the rate of conversion. When complete the reaction was quenched with sat. Rochelle's Salt. The quenched product mixture was then combined with fresh sat. Rochelle's salt and extracted with ethyl acetate (3×20 mL). The organic layers were combined, dried over magnesium sulfate, and the solvent removed in vacuo. The product was purified by silica gel chromatography.

Step e) Formation of rel-(2S,3aS,7aR)—N-hydroxy-1-[(4-methoxyphenyl)sulfonyl]-6-(3-methylbutanoyl)octahydro-1H-pyrrolo[2,3-c]pyridine-2-carboxamide (3) (Compound of Formula (I) wherein R$^1$ is 4-methoxyphenyl, R$^2$ is —C(O)-2-methylbutyl, R$^3$, R$^4$, R$^5$, R$^6$ are H)

(3)

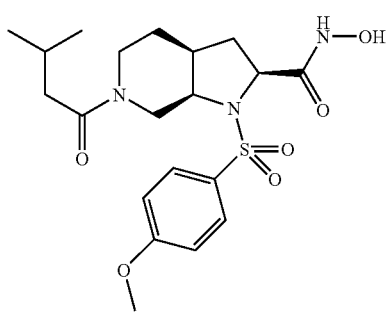

To a solution of rel-(2S,3aS,7aR)—N-(benzyloxy)-1-[(4-methoxyphenyl)sulfonyl]-6-(3-methylbutanoyl)octahydro-1H-pyrrolo[2,3-c]pyridine-2-carboxamide obtained under step d) (0.2 mmol) in ethanol (5 mL), was added 10% palladium on activated carbon (0.02 mmol). The reaction was placed under hydrogen (1.1 atm) and stirred for 24 hours. The reaction mixture was filtered and washed with ethanol (3×5 mL). The filtrates were collected and the solvent removed in vacuo to give the title compound (3) as a pink oil (10 mg). No purification was necessary. M$^+$(LC-MS (ESI)): 440. $^1$H NMR (400 MHz, CDCl$_3$); 0.9 (m, 6H), 1.0-2.2 (m, 8H), 3.2-3.3 (m, 1H), 3.5-3.7 (m, 4H), 3.8 (br s, 3H), 4.0-4.1 (m, 1H), 6.9 (m, 2H), 7.7 (m, 2H).

Example 4

Preparation of rel-2S,3aS,7aR)-6-(3-cyclopentylpropanoyl)-N-hydroxy-1-[(4-methoxyphenyl)sulfonyl]octahydro-1H-pyrrolo[2,3-c]pyridine-2-carboxamide (4) (Compound of Formula (I) wherein R$^1$ is 4-methoxyphenyl; R$^2$ is —C(O)-3-cyclopentylpropanoyl, R$^3$, R$^4$, R$^5$, R$^6$ are H)

(4)

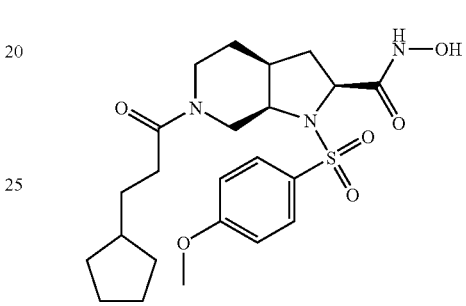

The same procedure as employed in the preparation of Example 3 but using 3-cyclopentyl-propionyl chloride (in step a) and 4-methoxy-benzenesulfonyl chloride (in step c) gave the title compound (4) as a pink oil (36 mg). M$^+$(LC-MS (ESI)): 480. $^1$H NMR (400 MHz, CDCl$_3$); 1.0-1.7 (m, 16H), 2.1-2.4 (m, 2H), 3.2-3.3 (m, 1H), 3.5-3.8 (m, 4H), 3.8 (s, 3H), 4.0-4.1 (m, 1H), 6.9 (m, 2H), 7.7 (m, 2H), 9.5-10.2 (br, 1H).

Example 5

Preparation of 2-methoxyethyl rel-(2S,3aS,7aR)-2-[(hydroxyamino)carbonyl]-1-[(4-methoxyphenyl)sulfonyl]octahydro-6H-pyrrolo[2,3-c]pyridine-6-carboxylate (5) (Compound of Formula (I) wherein R$^1$ is 4-methoxyphenyl, R$^2$ is —C(O)O-2-methoxyethyl, R$^3$, R$^4$, R$^5$, R$^6$ are H)

(5)

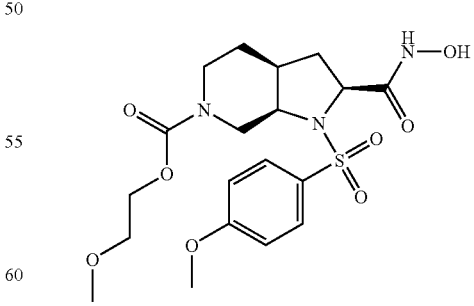

The same procedure as employed in the preparation of Example 3 but using 2-methoxy ethyl chloroformate (in step a) and 4-methoxy-benzenesulfonyl chloride (in step c) gave the title compound (5) as a brown oil (10 mg). M$^+$(LC-MS (ESI)): 458. $^1$H NMR (400 MHz, CDCl$_3$); 1.3-1.6 (m, 3H), 1.9-2.0 (m, 1H), 2.1-2.2 (m, 1H), 2.8-3.1 (m, 1H), 3.3-3.7 (m, 7H), 3.8-3.9 (m, 3H), 4.0-4.2 (m, 4H), 4.4-4.6 (m, 1H), 6.9-7.0 (m, 2H), 7.7-7.8 (m, 2H).

Example 6

Preparation of rel-(2S,3aS,7aR)-6-dodecanoyl-N-hydroxy-1-[(4-methoxy phenyl)sulfonyl]octahydro-1H-pyrrolo[2,3-c]pyridine-2-carboxamide (6) (Compound of Formula (I) wherein $R^1$ is 4-methoxyphenyl, $R^2$ is —C(O)-dodecanoyl, $R^3$, $R^4$, $R^5$, $R^6$ are H)

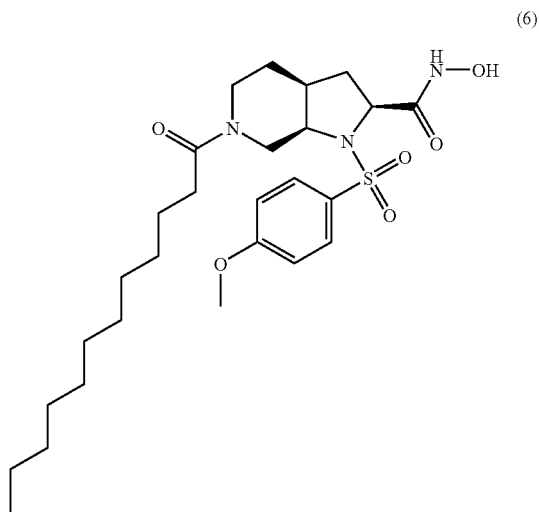

(6)

The same procedure as employed in the preparation of Example 3 but using lauroyl chloride (in step a) and 4-methoxy-benzenesulfonyl chloride (in step c) gave the title compound (6) as a pink solid (62 mg). M$^+$(LC-MS (ESI)): 538. $^1$H NMR (400 MHz, CDCl$_3$); 0.8 (t, 3H), 1.2 (m, 18H), 1.3-1.9 (m, 5H), 2.1-2.3 (m, 2H), 3.2-3.3 (m, 1H), 3.5-3.8 (m, 4H), 3.8 (m, 3H), 4.1-4.2 (m, 1H), 6.9 (m, 2H), 7.7 (m, 2H), 8.3-8.7 (br, <1H), 9.6-10.0 (br, 1H).

Example 7

Preparation of rel-2S,3aS,7aR)-6-cyclopentylcarbonyl)-N-hydroxy-1-[(4-methoxyphenyl)sulfonyl]octahydro-1H-pyrrolo[2,3-c]pyridine-2-carboxamide (7) (Compound of Formula (I) wherein $R^1$ is 4-methoxyphenyl, $R^2$ is —C(O)-cyclopentyl, $R^3$, $R^4$, $R^5$, $R^6$ are H)

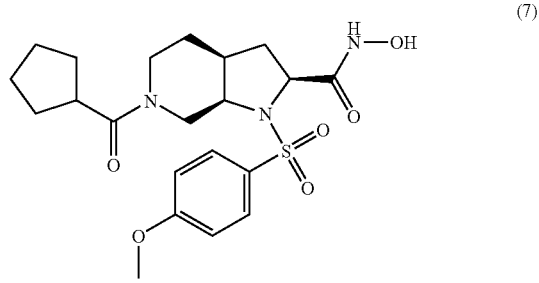

(7)

The same procedure as employed in the preparation of Example 3 but using cyclopentanecarbonyl chloride (in step a) and 4-methoxy-benzenesulfonyl chloride (in step c) gave the title (7) compound as a pink solid (47 mg). M$^+$(LC-MS (ESI)): 452. $^1$H NMR (400 MHz, CDCl$_3$); 1.3-1.9 (m, 13H), 2.0-2.3 (m, 1H), 2.7-3.2 (m, 2H), 3.4-3.8 (m, 6H), 4.0-4.4 (m, 1H), 6.8-7.0 (m, 2H), 7.7-7.8 (m, 2H).

Example 8

Preparation of rel-(2S,3aS,7aR)—N-hydroxy-1-[(4-methoxyphenyl)sulfonyl]-6-(3-phenylpropanoyl)octahydro-1H-pyrrolo[2,3-c]pyridine-2-carboxamide (8) (Compound of Formula (I) wherein $R^1$ is 4-methoxyphenyl, $R^2$ is —C(O)-phenyl ethyl, $R^3$, $R^4$, $R^5$, $R^6$ are H)

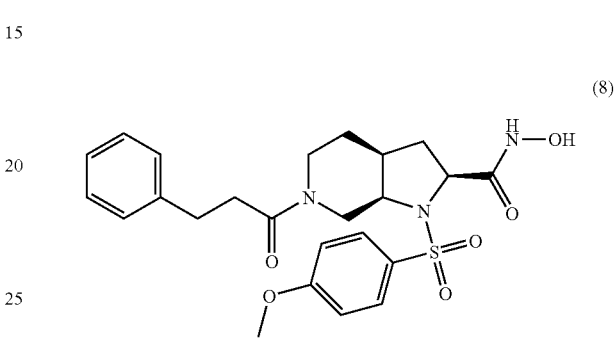

(8)

The same procedure as employed in the preparation of Example 3 but using 3-phenyl-propionyl chloride (in step a) and 4-methoxy-benzenesulfonyl chloride (in step c) gave the title compound (8) as a pink solid (44 mg). M$^+$(LC-MS (ESI)): 488. $^1$H NMR (400 MHz, CDCl$_3$); 1.3-1.5 (m, 2H), 1.6-2.0 (m, 2H), 2.1 (m, 1H), 2.4-2.7 (m, 2H), 2.9 (m, 2H), 3.0-3.2 (m, 2H), 3.6 (m, 1H), 3.7 (m, 2H), 3.8 (m, 3H), 4.0-4.2 (m, 1H), 6.9 (m, 2H), 7.1-7.3 (m, 5H), 7.7 (m, 2H), 9.6-10.2 (br, <1H).

Example 9

Preparation of rel-(2S,3aS,7aR)—N-hydroxy-1-[(4-methoxyphenyl)sulfonyl]-6-(methylsulfonyl)octahydro-1H-pyrrolo[2,3-c]pyridine-2-carboxamide (9) (Compound of Formula (I) wherein $R^1$ is 4-methoxyphenyl, $R^2$ is —SO$_2$-Me, $R^3$, $R^4$, $R^5$, $R^6$ are H)

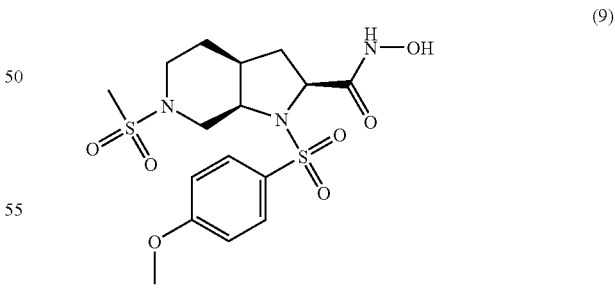

(9)

The same procedure as employed in the preparation of Example 3 but using methanesulfonyl chloride (in step a) and 4-methoxy-benzenesulfonyl chloride (in step c) gave the title compound (9) as a pink solid (10.4 mg). M$^+$(LC-MS (ESI)): 434. $^1$H NMR (400 MHz, CD$_3$OD); 1.5-1.8 (m, 3H), 1.9-2.1 (m, 2H), 2.7-2.8 (m, 4H), 2.9-3.0 (m, 1H), 3.3-3.4 (m, 1H), 3.6-3.7 (m, 1H), 3.7-3.8 (m, 1H), 3.8 (s, 3H), 3.8-3.9 (m, 1H), 7.0-7.1 (m, 2H), 7.7-7.8 (m, 2H).

Example 10

Preparation of rel-(2S,3aS,7aR)—N-hydroxy-1,6-bis[(4-methoxyphenyl)sulfonyl]octahydro-1H-pyrrolo[2,3-c]pyridine-2-carboxamide (10) (Compound of Formula (I) wherein $R^1$ is 4-methoxyphenyl, $R^2$ is —$SO_2$-4-methyoxyphenyl, $R^3$, $R^4$, $R^5$, $R^6$ are H)

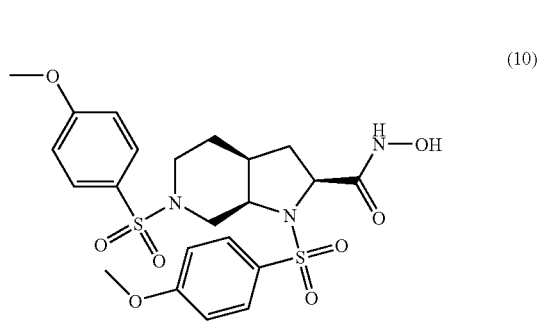

(10)

The same procedure as employed in the preparation of Example 3 but using 4-methoxy-benzenesulfonyl chloride (in step a and c) gave the title compound (10) as a white solid (33 mg). M+(LC-MS (ESI)): 526. $^1$H NMR (400 MHz, $CD_3COCD_3$); 1.5-2.0 (m, 5H), 2.3-2.5 (m, 1H), 2.6-2.7 (m, 1H), 3.4-3.5 (m, 1H), 3.7-3.8 (m, 1H), 3.8-4.0 (m, 8H) 7.1-7.2 (m, 4H), 7.7-7.8 (m, 2H), 7.9-8.0 (m, 2H).

Example 11

Preparation of rel-(2S,3aS,7aR)—N-hydroxy-6-(methylsulfonyl)-1-{[4-(pyridin-4-yloxy)phenyl]sulfonyl}octahydro-1H-pyrrolo[2,3-c]pyridine-2-carboxamide (11) (Compound of Formula (I) wherein $R^1$ is 4-methoxyphenyl; $R^2$ is —$SO_2$-Me; $R^3$, $R^4$, $R^5$ and $R^6$ are H)

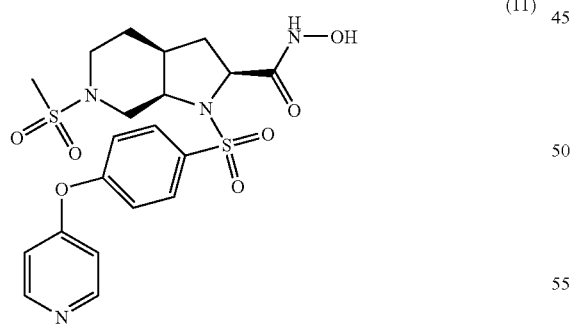

(11)

The same procedure as employed in the preparation of Example 3 but using methanesulfonyl chloride (in step a) and 4-(pyridin-4-yloxy)-benzenesulfonyl hydrochloride (in step c) gave the title compound (11) as a brown solid (7.7 mg). M+(LC-MS (ESI)): 497. $^1$H NMR (400 MHz, $CD_3OD$); 1.7-2.0 (m, 3H), 2.0-2.2 (m, 2H), 2.8-2.9 (m, 4H), 3.0-3.1 (m, 1H), 3.4-3.5 (m, 1H), 3.5-3.6 (m, 1H), 3.9-4.0 (m, 1H), 4.1-4.2 (m, 1H), 7.5-7.6 (m, 4H), 8.1-8.2 (m, 2H), 8.7-8.8 (m, 2H).

Example 12

Preparation of rel-(2S,3aS,7aR)-6-(biphenyl-4-ylcarbonyl)-N-hydroxy-1-[(4-methoxyphenyl)sulfonyl]octahydro-1H-pyrrolo[2,3-c]pyridine-2-carboxamide (12) (Compound of Formula (I) wherein $R^1$ is 4-methoxyphenyl; $R^2$ is —C(O)-biphenyl; $R^3$, $R^4$, $R^5$, $R^6$ are H)

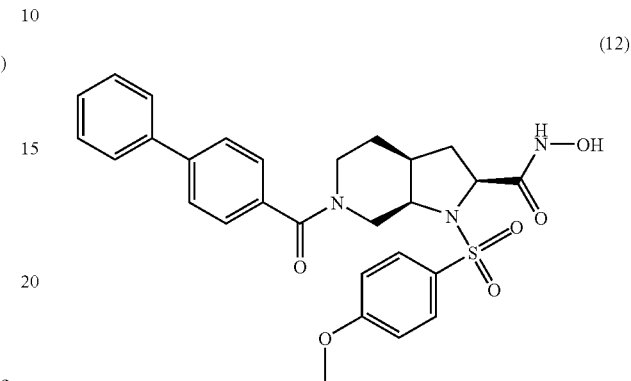

(12)

The same procedure as employed in the preparation of Example 3 but using 4-biphenylcarbonyl chloride (in step a) and 4-methoxy-benzenesulfonyl chloride (in step c) gave the title compound (12) as a pink solid (26 mg). M+(LC-MS (ESI)): 536. $^1$H NMR (400 MHz, $CDCl_3$); 1.5-2.6 (m, 5H), 3.2-3.8 (m, 3H), 3.8-4.1 (m, 4H), 4.1-4.5 (m, 2H), 6.9-7.2 (m, 2H), 7.4-8.1 (m, 11H).

Example 13

Preparation of rel-(2S,3aS,7aR)-6-(biphenyl-4-ylsulfonyl)-N-hydroxy-1-[(4-methoxyphenyl)sulfonyl]octahydro-1H-pyrrolo[2,3-c]pyridine-2-carboxamide (13) (Compound of Formula (I) wherein $R^1$ is 4-methoxyphenyl; $R^2$ is —$SO_2$-biphenyl; $R^3$, $R^4$, $R^5$, $R^6$ are H)

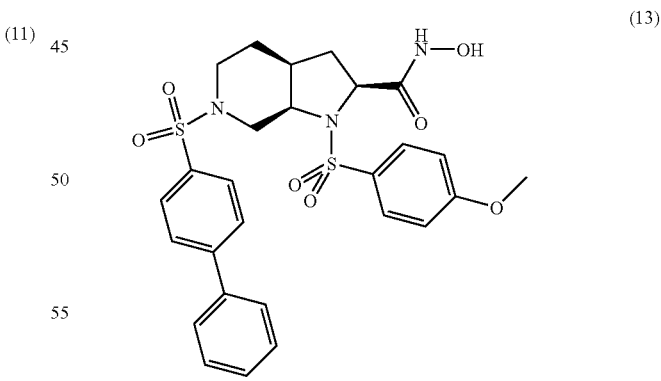

(13)

The same procedure as employed in the preparation of Example 3 but using 4-biphenylsulfonyl chloride (in step a) and 4-methoxy-benzenesulfonyl chloride (in step c) gave the title compound (13) as a white solid (18 mg). M+(LC-MS (ESI)): 572. $^1$H NMR (400 MHz, $CDCl_3$); 1.5-1.6 (m, 1H), 1.6-1.7 (m, 1H), 1.7-1.8 (m, 1H), 1.9-2.0 (m, 2H), 2.5-2.6 (m, 1H), 2.6-2.7 (m, 1H), 3.2-3.3 (m, 1H), 3.6-3.7 (m, 1H), 3.7-3.8 (m, 4H), 4.0-4.1 (m, 1H), 6.9-7.0 (m, 2H), 7.3-7.4 (m, 3H), 7.5-7.6 (m, 2H), 7.6-7.7 (m, 2H), 7.7-7.8 (m, 4H).

Example 14

Preparation of rel-(2S,3aS,7aR)-6-[2-(diethylamino)-2-oxoethyl]-N-hydroxy-1-[(4-methoxyphenyl)sulfonyl]octahydro-1H-pyrrolo[2,3-c]pyridine-2-carboxamide (14)

Step a) Formation of 1-tert-butyl 2-ethyl rel-(2S,3aS,7aR)-6-[2-(diethylamino)-2-oxoethyl]octahydro-1H-pyrrolo[2,3-c]pyridine-1,2-dicarboxylate (Compound of Formula IIa wherein $R^{11}$ is ethyl; $R^{13}$ is Boc; $R^3$, $R^4$, $R^5$, $R^6$ are H and $R^{14}$ is 2-diethylamino-2oxoethyl)

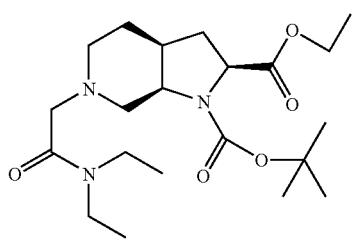

A solution was made of 1-tert-butyl 2-ethyl rel-(2S,3aS,7aR)-octahydro-1H-pyrrolo[2,3-c]pyridine-1,2-dicarboxylate obtained in Example 1 under step b) (100 mg, 0.335 mmol) in toluene (5 mL). Potassium carbonate (92.4 mg, 0.67 mmol) was added followed by 2-chloro-N,N-diethyl acetamide (0.352 mmol). t-butylammonium iodide (24.7 mg, 0.067 mmol) was then added and the reaction refluxed with stirring for 36 hours. The reaction mixture was allowed to cool before being quenched with water (10 mL) and the reaction mixture extracted with DCM (3×10 mL). The organic extracts were collected, dried over magnesium sulfate and filtered. The solvent was then removed in vacuo. The product was purified using silica gel chromatography using 2% methanol in DCM as the eluent.

Step b) Formation of rel-(2S,3aS,7aR)-6-[2-(diethylamino)-2-oxoethyl]-N-hydroxy-1-[(4-methoxyphenyl)sulfonyl]octahydro-1H-pyrrolo[2,3-c]pyridine-2-carboxamide (14) (Compound of Formula (I) wherein $R^1$ is 4-methoxyphenyl; $R^2$ is —CH$_2$C(O)—N(C$_2$H$_5$)$_2$; $R^3$, $R^4$, $R^5$, $R^6$ are H)

(14)

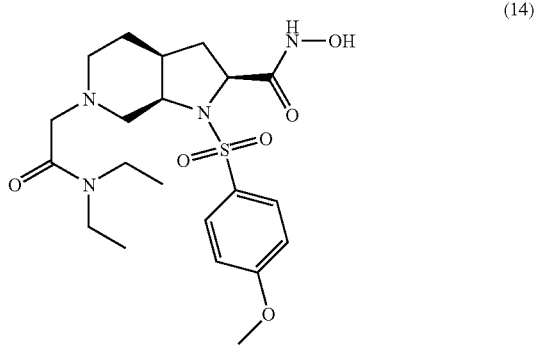

The same procedure as employed in the preparation of Example 3 but using 1-tert-butyl 2-ethyl rel-(2S,3aS,7aR)-6-[2-(diethylamino)-2-oxoethyl]octahydro-1H-pyrrolo[2,3-c]pyridine-1,2-dicarboxylate obtained in step a) above and 4-methoxybenzenesulfonyl chloride (in step c) gave the title compound (14) as a yellow solid (2.6 mg). M$^+$(LC-MS (ESI)): 469. $^1$H NMR (400 MHz, CD$_3$OD); 1.1 (t, 3H), 1.2 (t, 3H), 1.9-2.1 (m, 5H), 3.1-3.5 (m, 10H), 3.8 (s, 3H), 3.9 (m, 1H), 4.1-4.5 (m, 1H), 7.0 (d, 2H), 7.8 (d, 2H).

Example 15

Preparation of rel-(2S,3aS,7aR)-6-[2-(ethylamino)-2-oxoethyl]-N-hydroxy-1-[(4-methoxyphenyl)sulfonyl]octahydro-1H-pyrrolo[2,3-c]pyridine-2-carboxamide (15)

Step a) Formation of ethyl rel-(2S,3aS,7aR)-6-[2-(ethylamino)-2-oxoethyl]-1-[(4-methoxy phenyl)sulfonyl]octahydro-1H-pyrrolo[2,3-c]pyridine-2-carboxylate (Compound of Formula IIa wherein $R^{11}$ is ethyl; $R^{13}$ is —SO$_2$-4-methoxyphenyl; $R^3$, $R^4$, $R^5$, $R^6$ are H and $R^{14}$ is 2-(ethylamino)-2-oxoethyl)

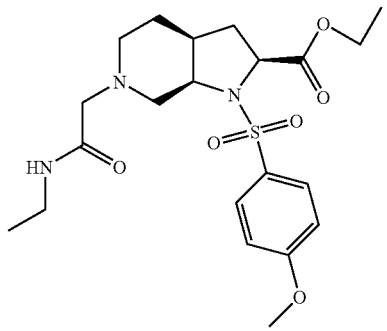

The same procedure as employed in the preparation of Example 14 but using (N-chloroacetyl)ethylamine (in step a) gave the title compound.

Step b) Formation of rel-(2S,3aS,7aR)-6-[2-(ethylamino)-2-oxoethyl]-1-[(4-methoxyphenyl)sulfonyl]octahydro-1H-pyrrolo[2,3-c]pyridine-2-carboxylic acid (Compound of Formula IIa wherein $R^{11}$ is H; $R^{13}$ is —SO$_2$-4-methoxyphenyl; $R^3$, $R^4$, $R^5$, $R^6$ are H and $R^{14}$ is 2-(ethylamino)-2-oxoethyl)

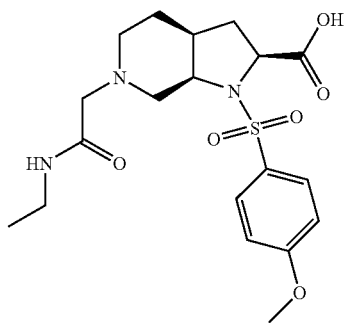

A solution of ethyl rel-(2S,3aS,7aR)-6-[2-(ethylamino)-2-oxoethyl]-1-[(4-methoxyphenyl)sulfonyl]octahydro-1H-pyrrolo[2,3-c]pyridine-2-carboxylate under step a) (62 mg, 0.13 mmol) was made in 1:1 THF:H$_2$O (20 vols). Lithium hydroxide monohydrate (65.5 mg, 1.56 mmol) was added and the reaction stirred at room temperature for 18 hours. The THF was removed in vacuo, and the aqueous layer extracted with EtOAc (3×10 mL). The organic extracts were collected, dried over magnesium sulfate and filtered. The solvent was then removed in vacuo, before being placed on a high vacuum line for 2 hours. The product was used in the next step with no further purification.

Step c) Formation of rel-(2S,3aS,7aR)—N-(benzyloxy)-6-[2-(ethylamino)-2-oxoethyl]-1-[(4-methoxyphenyl)sulfonyl]octahydro-1H-pyrrolo[2,3-c]pyridine-2-carboxamide (Compound of Formula Ia wherein $R^{12}$ is —CH$_2$-phenyl; —SO$_2$-4-methoxyphenyl; $R^3$, $R^4$, $R^5$, $R^6$ are H and $R^{14}$ is 2-(ethylamino)-2-oxoethyl)

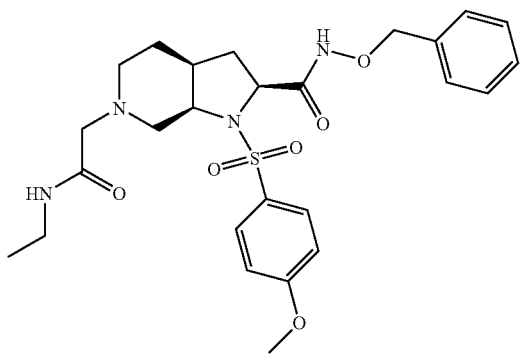

A solution of rel-(2S,3aS,7aR)-6-[2-(ethylamino)-2-oxoethyl]-1-[(4-methoxyphenyl)sulfonyl]octahydro-1H-pyrrolo[2,3-c]pyridine-2-carboxylic acid obtained under step b) (50 mg, 0.11 mmol) was made in anhydrous THF and the flask flushed with nitrogen. The mixture was cooled to −15° C. in an ice/salt bath, before n-Methylmorpholine (29.0 μl, 0.264 mmol) was added followed by isobutyl chloroformate (17.1 μl, 0.132 mmol). The reaction mixture was stirred −15° C. for 1 hour before being allowed to warm to room temperature. O-benzylhydroxylamine.hydrochloride (21.1 mg, 0.132 mmol) was then added and the reaction stirred at room temperature for 72 hours. The solvent was removed in vacuo and the product purified by reverse-phase preparative LC.

Step d) Formation of rel-(2S,3aS,7aR)-6-[2-(ethylamino)-2-oxoethyl]-N-hydroxy-1-[(4-methoxyphenyl)sulfonyl]octahydro-1H-pyrrolo[2,3-c]pyridine-2-carboxamide (15) (Compound of Formula (I) wherein $R^1$ is 4-methoxyphenyl; $R^2$ is —CH$_2$C(O)—NH(C$_2$H$_5$); $R^3$, $R^4$, $R^5$, $R^6$ are H)

(15)

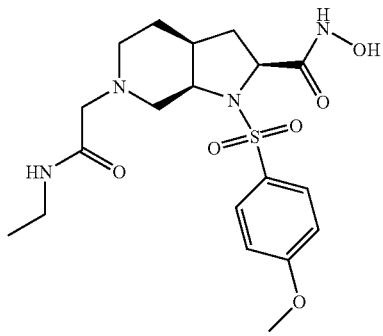

The same procedure as employed in the preparation of Example 3 but using rel-(2S,3aS,7aR)—N-(benzyloxy)-6-[2-(ethylamino)-2-oxoethyl]-1-[(4-methoxyphenyl)sulfonyl]octahydro-1H-pyrrolo[2,3-c]pyridine-2-carboxamide obtained under step b) above (in step e) gave the title compound (15) as a yellow oil (4.3 mg). M$^+$(LC-MS (ESI)): 441.

$^1$H NMR (400 MHz, CDCl$_3$); 1.1 (t, 3H), 1.3-1.9 (m, 5H), 3.0 (m, 3H), 3.2 (m, 2H), 3.6 (m, 4H), 3.8 (s, 3H), 4.1 (m, 1H), 6.9 (m, 3H), 7.7 (d, 2H).

Example 16

Preparation of rel-(2S,3aS,7aR)—N$^2$-hydroxy-1-[(4-methoxyphenyl)sulfonyl]-N$^6$-phenyloctahydro-6H-pyrrolo[2,3-c]pyridine-2,6-dicarboxamide (16)

Step a) Formation of 1-tert-butyl 2-ethyl rel-(2S,3aS,7aR)-6-(anilinocarbonyl)octahydro-1H-pyrrolo[2,3-c]pyridine-1,2-dicarboxylate (Compound of Formula IIa wherein $R^{11}$ is ethyl; $R^{13}$ is Boc; $R^3$, $R^4$, $R^5$, $R^6$ are H and $R^{14}$ is —CONH-Ph)

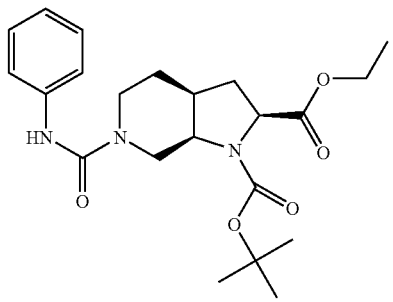

A solution of 1-tert-butyl 2-ethyl rel-(2S,3aS,7aR)-octahydro-1H-pyrrolo[2,3-c]pyridine-1,2-dicarboxylate (50 mg, 0.17 mmol) obtained in Example 1 under step b) and phenyl isocyanate (24 mg, 0.2 mmol) in 2 mL of THF was stirred at rt. After 5 h, 100 mg of aminomethyl polystyrene were added. After filtration, it was concentrated under reduced pressure. Column chromatography EtOAc/cHex (2/3) afforded the title compound (66 mg, 94%). HPLC purity: 98%. M$^+$(LC-MS (ESI)): 318. M$^-$(LC-MS (ESI)): 416. $^1$H NMR (CDCl$_3$) δ 7.46-7.32 (m, 2H), 7.07-6.88 (m, 3H), 4.36-4.07 (m, 3H), 4.02-3.91 (m, 1H), 3.89-3.60 (m, 2H), 3.43-3.27 (m, 1H), 2.60-2.38 (m, 1H), 2.39-2.22 (m, 1H), 2.06-1.80 (m, 3H), 1.53-1.35 (s, 9H), 1.33-1.04 (m, 3H).

Step b) Formation of rel-(2S,3aS,7aR)-6-(anilinocarbonyl)-2-(ethoxycarbonyl)octahydro-1H-pyrrolo[2,3-c]pyridin-1-ium chloride (the hydrochloride salt of compound of Formula IIa wherein $R^{11}$ is ethyl; $R^{13}$ is H; $R^3$, $R^4$, $R^5$, $R^6$ are H and $R^{14}$ is —CONH-Ph)

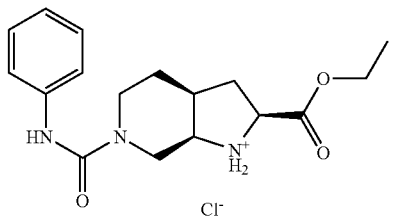

A solution of 1-tert-butyl 2-ethyl rel-(2S,3aS,7aR)-6-(anilinocarbonyl)octahydro-1H-pyrrolo[2,3-c]pyridine-1,2-dicarboxylate obtained under step a) (66 mg, 0.16 mmol) in 2 mL of DCM and HCl solution 4 M in 1,4-dioxane (0.79 mL, 20 eq.) was stirred overnight at rt. It was concentrated under reduced pressure. The title compound was obtained (48 mg, 93%). HPLC purity: 99%. M$^+$(LC-MS (ESI)): 319. M$^-$(LC- MS (ESI)): 317. ¹H NMR (CDCl₃) δ 8.08 (s, 1H), 7.62-7.42 (m, 2H), 7.32-7.14 (m, 3H), 7.05-6.89 (m, 1H), 4.62-4.39 (m, 2H), 4.32-4.19 (m, 2H), 4.13-3.97 (m, 1H), 3.93-3.82 (m, 1H), 3.70 (s, 3H), 3.51-3.37 (m, 1H), 3.12-2.92 (m, 1H), 2.63-2.38 (m, 2H), 2.22-1.92 (m, 3H), 1.32-1.07 (t, 3H).

Step c) Formation of ethyl rel-(2S,3aS,7aR)-6-(anilinocarbonyl)-1-[(4-methoxyphenyl)sulfonyl]octahydro-1H-pyrrolo[2,3-c]pyridine-2-carboxylate (Compound of Formula IIa wherein $R^{11}$ is ethyl; $R^{13}$ is —SO₂-4-methoxyphenyl; $R^3$, $R^4$, $R^5$ and $R^6$ are H and $R^{14}$ is —CONH-Ph)

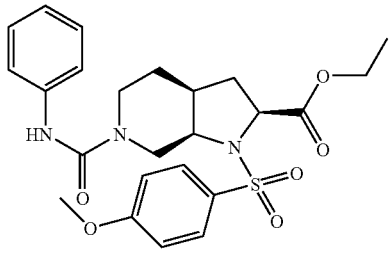

A solution of rel-(2S,3aS,7aR)-6-(anilinocarbonyl)-2-(ethoxycarbonyl)octahydro-1H-pyrrolo[2,3-c]pyridin-1-ium chloride obtained under step b) (48 mg, 0.15 mmol) and DIEA (0.2 mL, 7.85 eq.) in 2 mL of DCM was cooled at 0° C. At 0° C. 4-methoxybenzenesulfonyl chloride (130 mg, 4.15 eq) was added. It was stirred over night at rt. To remove the excess of 4-methoxybenzenesulfonyl chloride, 313 mg of aminomethyl polystyrene was added. After a day, the resins were removed by filtration, washed with DCM and the filtrate was concentrated under reduced pressure. Then, a column chromatography purified the desired product (40 mg, 53%). HPLC purity: 98%. M⁺(LC-MS (ESI)): 4888. M⁻(LC-MS (ESI)): 486. ¹H NMR (CDCl₃) δ 7.78-7.70 (d, 2H, J=8.77), 7.43-7.36 (d, 2H, J=7.54), 7.29-7.17 (m, 3H), 7.01-6.89 (m, 3H), 4.19-4.04 (m, 3H), 4.02-3.91 (m, 1H), 3.86 (s, 3H), 3.77-3.61 (m, 1H), 3.53-3.35 (m, 2H), 3.20-3.09 (m, 1H), 2.18-1.84 (m, 2H), 1.78-1.38 (m, 3H), 1.36-0.99 (t, 3H).

Step d) Formation of rel-(2S,3aS,7aR)-6-(anilinocarbonyl)-1-[(4-methoxyphenyl)sulfonyl]octahydro-1H-pyrrolo[2,3-c]pyridine-2-carboxylic acid (Compound of Formula IIa wherein $R^{11}$ is H; $R^{13}$ is —SO₂-4-methoxyphenyl; $R^3$, $R^4$, $R^5$, $R^6$ are H and $R^{14}$ is —CONHPh)

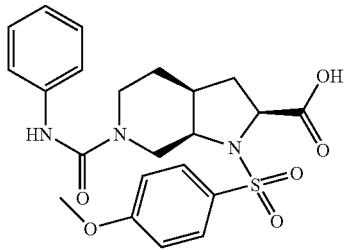

To a solution of ethyl rel-(2S,3aS,7aR)-6-(anilinocarbonyl)-1-[(4-methoxyphenyl)sulfonyl]octahydro-1H-pyrrolo[2,3-c]pyridine-2-carboxylate obtained under step c) (39 mg, 0.08 mmol) in 2 ml of EtOH was added NaOH 1M (0.48 mL, 6 eq.) at rt. It was stirred over night at rt. A work up was made with HCl 1N and EtOAc. The combined organic layer was dried over MgSO4 and concentrated under reduced pressure to give the title compound (32 mg, 87%). HPLC purity: 94%.

M⁺(LC-MS (ESI)): 460. ¹H NMR (CDCl₃) δ 7.81-7.70 (d, 2H, J=7.9), 7.37-7.28 (d, 2H, J=8.01), 7.25-7.17 (m, 3H), 7.02-6.92 (m, 2H), 4.21-4.12 (m, 1H), 4.09-3.91 (m, 2H), 3.83 (s, 3H), 3.52-3.37 (m, 2H), 3.12-2.65 (m, 2H), 2.19-2.09 (m, 1H), 2.04-1.89 (m, 2H), 1.69-1.40 (m, 2H).

Step e) Formation of rel-(2S,3aS,7aR)—N²-(benzyloxy)-1-[(4-methoxyphenyl)sulfonyl]-N⁶-phenyloctahydro-6H-pyrrolo[2,3-c]pyridine-2,6-dicarboxamide (Compound of Formula Ia wherein $R^{12}$ is —CH₂-Ph; $R^{13}$ is —SO₂-4-methoxyphenyl; $R^3$, $R^4$, $R^5$, $R^6$ are H and $R^{14}$ is —CONH-phenyl)

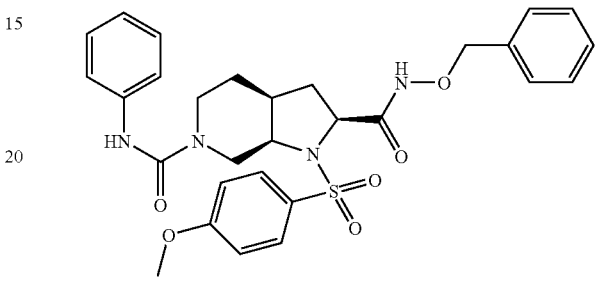

To a solution of rel-(2S,3aS,7aR)-6-(anilinocarbonyl)-1-[(4-methoxyphenyl)sulfonyl]octahydro-1H-pyrrolo[2,3-c]pyridine-2-carboxylic acid obtained under step d) (32 mg, 0.07 mmol) in 2 mL of THF, the NMM (8 mg, 1.2 eq.) was added. The mixture was cooled to −15° C. and isobutyl chloroformate (10 mg, 1.1 eq.) was added. The reaction was kept under these conditions and stirred for 20 minutes. Then, O-benzylhydroxylamine (10 mg, 1.2 eq.) was added. The reaction mixture was stirred at rt for 2 hours. The work up was made with H₂O and EtOAc. The organic layer was dried over MgSO4 and was concentrated under reduced pressure. A column chromatography AcOEt/cHex (4/1) gave the title compound (16 mg, 40%). HPLC purity: 100%. M⁺(LC-MS (ESI)): 465. M⁻(LC-MS (ESI)): 463. ¹H NMR (CDCl₃) δ 9.25 (s, 1H), 7.78-7.66 (d, 2H, J=8.25), 7.52-7.44 (d, 2H, J=6.42), 7.34-7.16 (m, 8H), 7.03-6.95 (m, 2H), 4.74 (s, 2H), 3.84 (s, 3H), 3.45-3.29 (m, 2H), 2.91-2.79 (m, 1H), 2.16-2.00 (m, 1H), 1.98 (s, 1H), 1.76-1.44 (m, 2H).

Step f) Formation of rel-(2S,3aS,7aR)—N²-hydroxy-1-[(4-methoxyphenyl)sulfonyl]-N⁶-phenyl octahydro-6H-pyrrolo[2,3-c]pyridine-2,6-dicarboxamide (16) (Compound of Formula (I) wherein $R^1$ is 4-methoxyphenyl; $R^2$ is —C(O)—NH-Ph; $R^3$, $R^4$, $R^5$, $R^6$ are H)

(16)

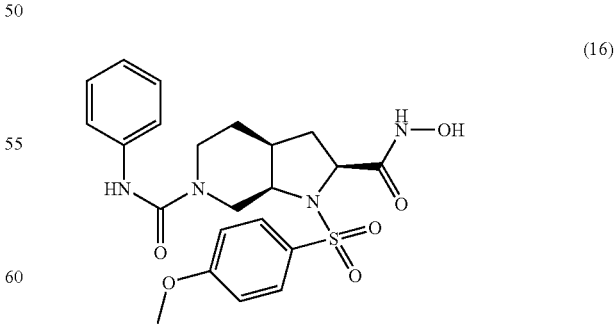

To a solution of rel-(2S,3aS,7aR)—N²-(benzyloxy)-1-[(4-methoxyphenyl)sulfonyl]-N⁶-phenyloctahydro-6H-pyrrolo[2,3-c]pyridine-2,6-dicarboxamide obtained under step e) in 5 mL of EtOH 10% Pd/C (3 mg, 0.1 eq) was added. The suspension was hydrogenated at rt for 3 h. The catalyst was removed by filtration through a Celite pad, washed with EtOH and the filtrate was concentrated to give the title compound (16) (12 mg, 89%). HPLC purity: 94%. M⁺(LC-MS (ESI)): 475. M⁻(LC-MS (ESI)): 473. ¹H NMR (CDCl₃) δ 9.46 (s, 1H), 7.96-7.62 (d, 2H, J=8.25), 7.52-7.35 (d, 2H, J=6.42), 7.31-7.13 (m, 2H), 7.04-6.83 (m, 3H), 4.94 (s, 1H), 4.24-3.99 (s, 1H), 3.81 (s, 3H), 3.67-3.24 (m, 2H), 3.07-2.83 (m, 1H), 2.34-2.07 (m, 2H), 1.66-1.42 (m, 3H), 1.29-0.99 (m, 3H).

Example 17

Preparation of rel-(2S,3aS,7aR)—N-hydroxy-1-[(4-methoxyphenyl)sulfonyl]octahydro-1H-pyrrolo[2,3-c]pyridine-2-carboxamide (17)

Step a) Formation 6-benzyl 1-tert-butyl 2-ethyl rel-(2S,3aS,7aR)-hexahydro-1H-pyrrolo[2,3-c]pyridine-1,2,6(2H)-tricarboxylate (Compound of Formula IIa wherein $R^{11}$ is ethyl; $R^{13}$ is Boc; $R^{14}$ is Z, $R^3$, $R^4$, $R^5$, $R^6$ are H)

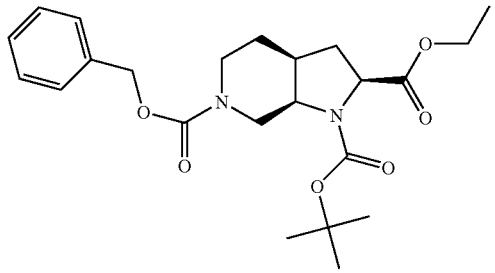

A solution of 1-tert-butyl 2-ethyl rel-(2S,3aS,7aR)-octahydro-1H-pyrrolo[2,3-c]pyridine-1,2-dicarboxylate obtained in Example 1 under step b) (500 mg, 1.68 mmol) and DIEA (373 mL, 2.2 eq.) in 20 mL of DCM was cooled at 0° C. At 0° C. 3-phenylpropionyl chloride (343 mg, 1.2 eq.) was added. It was stirred over night at rt. A work up was made with DCM and HCl 1N. The organic layer was dried over MgSO₄ and concentrated under reduced pressure. Then, flash chromatography EtOAc/cHex 20/80 afforded the title compound (519 mg, 72%). HPLC purity: 94%. M⁺(LC-MS (ESI)): 333. ¹H NMR (CDCl₃) δ 7.41-7.20 (m, 5H), 5.23-5.03 (m, 2H), 4.53-4.35 (m, 1H), 4.31-4.07 (m, 2H), 4.02-3.77 (m, 2H), 3.02-2.79 (m, 2H), 2.51-2.38 (m, 1H), 2.30-2.16 (m, 1H), 2.07-1.82 (m, 3H), 1.70-1.55 (m, 1H), 1.34 (s, 9H), 1.32-1.17 (m, 3H).

Step b) Formation of rel-(2S,3aS,7aR)-6-[(benzyloxy)carbonyl]-2-(ethoxycarbonyl)octahydro-1H-pyrrolo[2,3-c]pyridin-1-ium chloride (the hydrochloride salt of compound of Formula IIa wherein $R^{11}$ is ethyl; $R^{13}$ is H; $R^{14}$ is Z; $R^3$, $R^4$, $R^5$, $R^6$ are H)

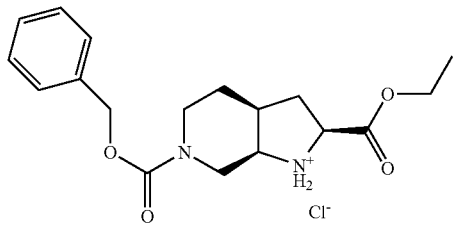

A solution of 6-benzyl 1-tert-butyl 2-ethyl rel-(2S,3aS,7aR)-hexahydro-1H-pyrrolo[2,3-c]pyridine-1,2,6(2H)-tricarboxylate obtained under step a) (519 mg, 1.20 mmol) in 13 mL of DCM and HCl solution 4M in 1,4-dioxane (6 mL, 20 eq.). It was stirred over night at rt. It was concentrated under reduced pressure. The title compound was obtained (488 mg, quantitative yield). HPLC purity: 96%. ¹H NMR (CDCl₃) δ 7.48-6.85 (m, 5H), 5.27-4.91 (m, 2H), 4.64-4.46 (m, 1H), 4.31-4.18 (m, 2H), 4.11-3.89 (m, 2H), 3.77-3.54 (m, 4H), 3.15-2.99 (m, 1H), 2.66-2.46 (m, 2H), 2.08-1.94 (m, 1H), 1.79-1.65 (m, 1H), 1.39-1.15 (m, 3H).

Step c) Formation of 6-benzyl 2-ethyl rel-(2S,3aS,7aR)-1-[(4-methoxyphenyl)sulfonyl]octahydro-6H-pyrrolo[2,3-c]pyridine-2,6-dicarboxylate (Compound of Formula IIa wherein $R^{11}$ is ethyl; $R^{13}$ is —SO₂-4-methoxyphenyl; $R^3$, $R^4$, $R^5$, $R^6$ are H and $R^{14}$ is Z)

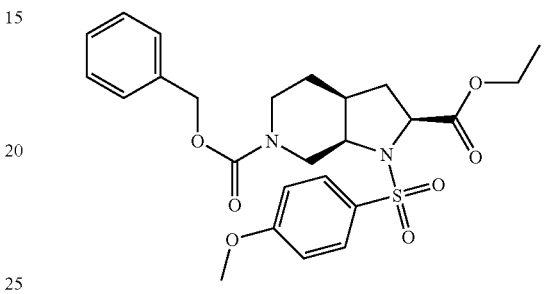

A solution of rel-(2S,3aS,7aR)-6-[(benzyloxy)carbonyl]-2-(ethoxycarbonyl)octahydro-1H-pyrrolo[2,3-c]pyridin-1-ium chloride obtained under step b) (488 mg, 1.32 mmol) and DIEA (0.5 mL, 2.20 eq.) in 17 mL of DCM was cooled at 0° C. At 0° C. 4-methoxybenzenesulfonyl chloride (301 mg, 1.1 eq.) was added. It was stirred overnight at rt. A work up with DCM and HCl 1N was made. The organic layer was dried over MgSO₄ and concentrated under reduced pressure. The title compound was obtained (211 mg, 32%). HPLC purity: 97%. M⁺(LC-MS (ESI)): 503. ¹H NMR (CDCl₃) δ 7.91-7.76 (d, 2H, j=7.55), 7.45-7.30 (m, 5H), 7.03-6.88 (d, 2H, J=7.55), 5.21-5.08 (m, 2H), 4.32-4.10 (m, 4H), 3.75 (s, 3H), 3.83-3.72 (m, 2H), 3.09-2.77 (m, 2H), 2.17-2.01 (m, 3H), 1.90-1.74 (m, 1H), 1.69-1.53 (m, 1H), 1.37-1.22 (t, 3H, J=5.66).

Step d) Formation of rel-(2S,3aS,7aR)-6-[(benzyloxy)carbonyl]-1-[(4-methoxyphenyl)sulfonyl]octahydro-1H-pyrrolo[2,3-c]pyridine-2-carboxylic acid (Compound of Formula IIa wherein $R^{11}$ is H; $R^{13}$ is —SO₂-4-methoxyphenyl; $R^3$, $R^4$, $R^5$, $R^6$ are H and $R^{14}$ is Z)

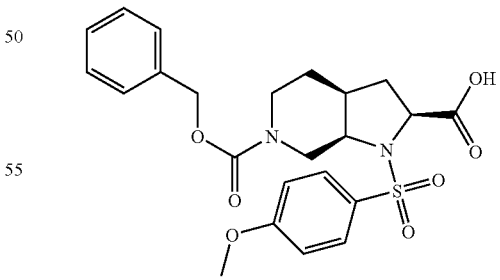

To a solution of 6-benzyl 2-ethyl rel-(2S,3aS,7aR)-1-[(4-methoxyphenyl)sulfonyl]octahydro-6H-pyrrolo[2,3-c]pyridine-2,6-dicarboxylate obtained under step c) (100 mg, 0.2 mmol) in 8 ml of ethanol, NaOH 1M (0.48 mL, 6 eq.) was added at rt. It was stirred over night at rt. The work up was made with 1N HCl and EtOAc. The combined organic layer was dried over MgSO₄ and concentrated under reduced pressure to give the title compound (85 mg, 91%). HPLC purity:

100%. M+(LC-MS (ESI)): 475. ¹H NMR (CDCl₃) δ 7.80-7.69 (d, 2H, j=6.60), 7.35-7.22 (m, 5H), 6.97-6.85 (d, 2H, J=6.92), 5.11-5.38 (m, 2H), 4.22-4.11 (m, 2H), 3.75 (s, 3H), 3.73-3.62 (m, 2H), 3.05-2.80 (m, 2H), 2.01-1.89 (m, 3H), 1.78-1.63 (m, 1H), 1.54-1.43 (m, 1H).

Step e) Formation of benzyl rel-(2S,3aS,7aR)-2-{[(benzyloxy)amino]carbonyl}-1-[(4-methoxyphenyl)sulfonyl]octahydro-6H-pyrrolo[2,3-c]pyridine-6-carboxylate (Compound of Formula Ia, wherein $R^{12}$ is —CH₂-Ph; $R^{13}$ is —SO₂-4-methoxyphenyl; $R^3$, $R^4$, $R^5$, $R^6$ are H and $R^{14}$ is Z)

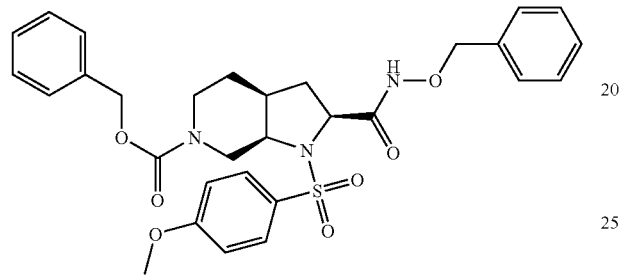

To a solution rel-(2S,3aS,7aR)-6-[(benzyloxy)carbonyl]-1-[(4-methoxyphenyl)sulfonyl]octahydro-1H-pyrrolo[2,3-c]pyridine-2-carboxylic acid obtained under step d) (85 mg, 0.18 mmol) in 2 mL of THF, the N-methylmorpholine (22 mg, 1.2 eq.) was added. The mixture was cooled to −15° C. and isobutyl chloroformate (27 mg, 1.1 eq.) was added. The reaction was kept under these conditions and was stirred for 20 minutes. Then, O-benzylhydroxylamine (26 mg, 1.2 eq.) was added. The reaction mixture was stirred at rt for 3 hours. The work up was made with H₂O and EtOAc. The combined organic layer was dried over MgSO₄ and was concentrated under reduced pressure. A column chromatography EtOAc/cHex (5/5) gave the title compound (66 mg, 74%). HPLC purity: 99%. M+(LC-MS (ESI)): 580. M⁻(LC-MS (ESI)): 578. ¹H NMR (CDCl₃) δ 9.30-9.01 (s, 1H), 7.71-7.61 (d, 2H, j=8.02), 7.41-7.17 (m, 10H), 6.95-6.83 (d, 2H, J=8.66), 5.16-5.00 (m, 2H), 4.95-4.76 (m, 2H), 3.90-3.88 (m, 1H), 3.80 (s, 3H), 3.67-3.46 (m, 2H), 3.03-2.78 (m, 2H), 2.14-2.02 (m, 1H), 2.00-1.83 (m, 3H), 1.78-1.48 (m, 1H), 1.44-1.31 (m, 1H).

Step f) Formation of rel-(2S,3aS,7aR)—N-hydroxy-1-[(4-methoxyphenyl)sulfonyl]octahydro-1H-pyrrolo[2,3-c]pyridine-2-carboxamide (17) (Compound of Formula (I) wherein $R^1$ is 4-methoxyphenyl; $R^2$ is H; $R^3$, $R^4$, $R^5$, $R^6$ are H)

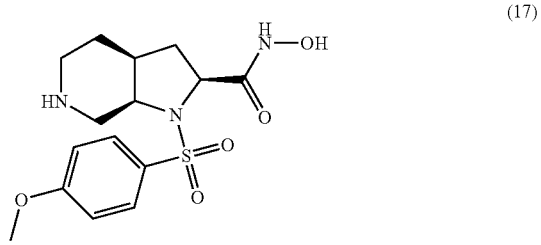

(17)

To a solution of benzyl rel-(2S,3aS,7aR)-2-{[(benzyloxy)amino]carbonyl}-1-[(4-methoxyphenyl)sulfonyl]octahydro-6H-pyrrolo[2,3-c]pyridine-6-carboxylate obtained under step e) in 10 mL of EtOH 10% Pd/C (12 mg, 0.1 eq) was added. The suspension was hydrogenated at rt for 1 day under 1 bars. The catalyst was removed by filtration through a Celite pad, washed with EtOH and the filtrate was concentrated to give the title compound (17) (18 mg, 44%). M+(LC-MS (ESI)): 356. ¹H NMR (DMSO) δ 10.80-10.62 (d, 1H, J=22.64), 7.84-7.67 (d, 1H, J=11.32), 7.84-7.67 (m, 2H), 7.18-7.02 (m, 2H), 3.88-3.69 (s, 3H), 3.12-3.04 (m, 1H), 2.85-2.62 (m, 2H), 1.96-1.82 (m, 2H), 1.66-1.42 (m, 3H), 1.29-0.99 (m, 3H), 0.87-0.70 (m, 1H).

Example 18

Preparation of benzyl rel-(2S,3aS,7aR)-2-[(hydroxyamino)carbonyl]-1-[(4-methoxyphenyl)sulfonyl]octahydro-6H-pyrrolo[2,3-c]pyridine-6-carboxylate (18)

Step a) Formation of rel-(2S,3aS,7aR)-6-[(benzyloxy)carbonyl]-1-[(4-methoxyphenyl)sulfonyl]octahydro-1H-pyrrolo[2,3-c]pyridine-2-carboxylic acid (Compound of Formula IIa wherein $R^{11}$ is H; $R^{13}$ is —SO₂-4-methoxyphenyl; $R^3$, $R^4$, $R^5$, $R^6$ are H and $R^{14}$ is Z)

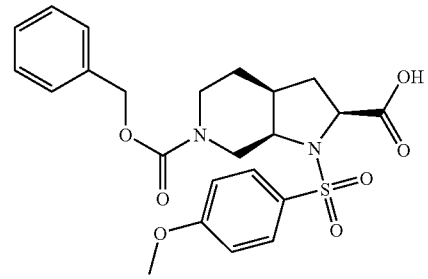

To a solution of rel-(2S,3aS,7aR)-6-[(benzyloxy)carbonyl]-1-[(4-methoxyphenyl)sulfonyl]octahydro-1H-pyrrolo[2,3-c]pyridine-2-carboxylic acid obtained in Example 17 under step d) (100 mg, 0.2 mmol) in 8 ml of EtOH, NaOH 1M (0.48 mL, 6 eq.) was added at rt. It was stirred over night at rt. The work up was made with HCl 1N and EtOAc. The combined organic layer was dried over MgSO₄ and concentrated under reduced pressure to give the title compound (85 mg, 91%).

HPLC purity: 100%. M+(LC-MS (ESI)): 475. ¹H NMR (CDCl₃) δ 7.80-7.69 (d, 2H, j=6.60), 7.35-7.22 (m, 5H), 6.97-6.85 (d, 2H, J=6.92), 5.11-5.38 (m, 2H), 4.22-4.11 (m, 2H), 3.75 (s, 3H), 3.73-3.62 (m, 2H), 3.05-2.80 (m, 2H), 2.01-1.89 (m, 3H), 1.78-1.63 (m, 1H), 1.54-1.43 (m, 1H).

Step b) Formation of benzyl rel-(2S,3aS,7aR)-2-[(hydroxyamino)carbonyl]-1-[(4-methoxy phenyl)sulfonyl]octahydro-6H-pyrrolo[2,3-c]pyridine-6-carboxylate (18) (Compound of Formula (I) wherein $R^1$ is 4-methoxyphenyl; $R^2$ is Z; $R^3$, $R^4$, $R^5$, $R^6$ are H)

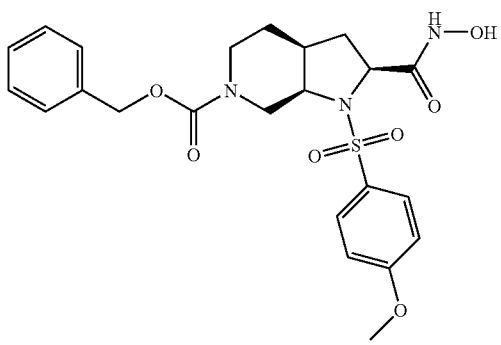

(18)

To a solution of rel-(2S,3aS,7aR)-6-[(benzyloxy)carbonyl]-1-[(4-methoxyphenyl)sulfonyl]octahydro-1H-pyrrolo[2,3-c]pyridine-2-carboxylic acid obtained under step a) (20 mg, 0.04 mmol) in 1 mL of DCM, HOBT (6.84 mg; 0.05 mmol; 1.20 eq.) was added and DCC (10.44 mg; 0.05 mmol; 1.20 eq.). It was stirred for 5 min at rt. Then, DIEA (0.02 ml; 0.08 mmol; 2.00 eq.) and finally, hydroxylamine hydrochloride (5.86 mg; 0.08 mmol; 2.00 eq.) were added. After 3h30, $NH_2$-column chromatography was made with DCM to give the title compound (18) (14 mg, 68%). HPLC purity: 93%. $M^+$(LC-MS (ESI)): 490. $M^-$(LC-MS (ESI)): 488. $^1$H NMR (MeOH) δ 7.73-7.71 (d, 2H, J=6.13), 7.28 (s, 5H), 7.00-6.97 (d, 2H, J=7.07), 5.02 (m, 2H), 4.05-3.92 (m, 1H), 3.89-3.86 (m, 1H), 3.77 (s, 3H), 3.67-3.52 (m, 2H), 3.23-3.03 (m, 3H), 2.24-2.12 (m, 1H), 2.10-1.93 (m, 3H), 1.88-1.58 (m, 1H), 1.54-1.41 (m, 1H).

Example 19

Preparation of 6-acetyl-N-hydroxy-1-[(4-methoxyphenyl)sulfonyl]-4,5,6,7-tetrahydro-1H-pyrrolo[2,3-c]pyridine-2-carboxamide (19)

Step a) Formation of 6-acetyl-1-[(4-methoxyphenyl)sulfonyl]-4,5,6,7-tetrahydro-1H-pyrrolo[2,3-c]pyridine-2-carboxylic acid (Compound of Formula IIa wherein $R^{11}$ is H; $R^{13}$ is —$SO_2$-4-methoxyphenyl; $R^3$, $R^4$, $R^5$, $R^6$ are H and $R^{14}$ is Ac)

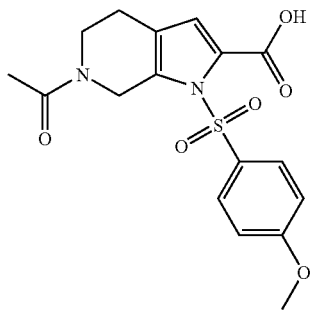

To a solution of ethyl 6-acetyl-1-[(4-methoxyphenyl)sulfonyl]-4,5,6,7-tetrahydro-1H-pyrrolo[2,3-c]pyridine-2-carboxylate obtained in Example 2 under step c) (500 mg, 1.23 mmol) in ethanol (22.5 mL) at room temperature was added sodium hydroxide solution (590 mg, 14.76 mmol, 12 eq., in 22.5 mL $H_2O$). The reaction mixture was stirred at rt for 48 hours and partitioned between 1 N HCl and EtOAc. The combined organic layers were dried over $Na_2SO_4$ and concentrated. Purification by preparative HPLC followed by lyophilisation gave the title compound (183 mg, 39%).

HPLC purity: 98%; LC-MS +Q1 379, −Q1 378. $^1$H NMR (300 MHz, $CD_3OD$) δ 2.19 (d, 3H, J=2.6 Hz), 2.59 (dt, 2H, J1=5.6 Hz, J2=27.5 Hz), 3.76 (dt, 2H, J1=6.0 Hz, J2=14.7 Hz), 3.89 (d, 3H, J=1.5 Hz), 4.95 (d, 2H, J=15.8 Hz), 6.82 (d, 1H, J=2.6 Hz), 7.05-7.13 (m, 2H), 7.97-8.04 (m, 2H).

Step b) Formation of 6-acetyl-N-(benzyloxy)-1-[(4-methoxyphenyl)sulfonyl]-4,5,6,7-tetra hydro-1H-pyrrolo[2,3-c]pyridine-2-carboxamide (Compound of Formula IIa wherein $R^{12}$ is —$CH_2$-Ph; $R^{13}$ is —$SO_2$-4-methoxyphenyl; $R^3$, $R^4$, $R^5$, $R^6$ are H and $R^{14}$ is Ac)

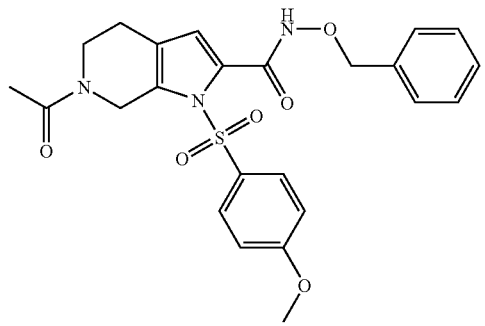

A solution of 6-acetyl-1-[(4-methoxyphenyl)sulfonyl]-4,5,6,7-tetrahydro-1H-pyrrolo[2,3-c]pyridine-2-carboxylic acid obtained under step a) (178 mg, 0.47 mmol) and N-methylmorpholine (61 µL, 0.56 mmol, 1.2 eq.) in THF (3 mL) was cooled to −15° C. and isobutyl chloroformate (67 µL, 0.52 mmol, 1.1 eq.) was added. The reaction was kept under these conditions and stirred for 30 minutes. O-benzylhydroxylamine (69 mg, 0.56 mmol, 1.2 eq.) was added. The reaction mixture was stirred at rt for 2 hours and was partitioned between water and EtOAc. The combined organic layers were dried over $Na_2SO_4$ and concentrated. Column chromatography (gradient c-Hex/EtOAc 20/80 to EtOAc in 25 minutes) afforded the title compound (100 mg, 44%).

HPLC purity: 98% $M^+$(LC-MS (ESI)): 484, $M^-$(LC-MS (ESI)): 482

$^1$H NMR (300 MHz, $CDCl_3$) δ 2.13 (s, 3H), 2.49 (br s, 2H), 3.64 (d, 2H, J=38.8 Hz), 3.87 (s, 3H), 4.79 (d, 2H, J=47.5 Hz), 5.07 (s, 2H), 6.27 (s, 1H), 7.00-7.03 (m, 2H), 7.33-7.44 (m, 3H), 7.48 (dd, 2H, J1=1.9 Hz, J2=7.5 Hz), 8.07-8.24 (m, 2H), 8.40 (br s, 1H)

$R_f$(c-Hex/EtOAc 20/80)=0.2.

Step c) Formation of 6-acetyl-N-hydroxy-1-[(4-methoxyphenyl)sulfonyl]-4,5,6,7-tetrahydro-1H-pyrrolo[2,3-c]pyridine-2-carboxamide (Compound of Formula (I) wherein $R^1$ is 4-methoxyphenyl; $R^2$ is Ac; $R^3$, $R^4$, $R^5$ and $R^6$ are H)

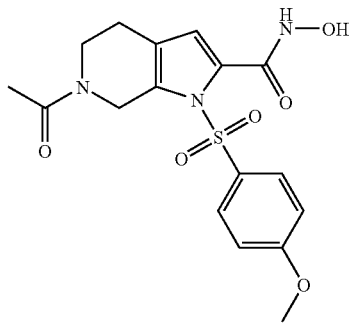

(19)

6-Acetyl-1-(4-methoxy-benzenesulfonyl)-octahydro-pyrrolo[2,3-c]pyridine-2-carboxylic acid benzyloxy-amide obtained under step b) (98 mg, 0.20 mmol) was dissolved in ethanol (2 mL) and 10% Pd/C (43 mg, 0.2 eq.) was added. The suspension was hydrogenated (1 Bar) at rt for 14 hours. The catalyst was removed by filtration through a Celite pad, was washed with ethanol and the filtrate was evaporated to give the title compound (19) (91 mg). HPLC purity: 70%.

Biological Assays:

The compounds of the present invention may be subjected to the following assays:

Example 20

Enzyme Inhibition Assays

Compounds of the invention were tested to assess their activities as inhibitors of MMP-1, MMP-2, MMP-9, MMP-14 and MMP-12.

MMP-9 Assay Protocol

Compounds of the invention were tested for inhibitory activity against 92 kDa gelatinase (MMP-9) in an assay using a coumarin-labeled peptide substrate, (7-methoxycoumarin-4-yl)acetyl-Pro-Leu-Gly-Leu-(3-[2,4-dinitrophenyl]-L-2,3diaminopropionyl)-Ala-Arg-NH2 (McaPLGLDpaAR) (Knight et al, *FEBS Lett*. 1992; 263-266).

Stock solutions were made up as follows: Assay Butter: 100 mM Tris-HCl pH 7.6 containing 100 mM NaCl, 10 mM CaCl$_2$, and 0.05% Brij 35.

Substrate: 0.4 mM McaPLGLDpaAR (from Bachem) (0.437 mg/ml) stock solution in 100% DMSO (stored at −20° C.). Dilute to 8 µM in assay butter.

Enzyme: Recombinant human 92 kDa gelatinase (MMP-9; APMA (4-aminophenyl mercuric acetate)-activated if necessary) appropriately diluted in assay butter.

Test Compounds were prepared initially as 10 mM compound solution in 100% DMSO, diluted to 1 mM in 100% DMSO, then serially diluted 3-fold in 100% DMSO across columns 1-10 of a 96-well microtitre plate Assay concentration range, 100 µM (column 1) to 5.1 nM (column 10).

The assay was performed in a total volume of 100 µL per well in 96-well microtitre plates. Activated enzyme (20 µL) was added to the wells followed by 20 µL of assay butter. Appropriate concentrations of test compounds dissolved in 10 µL of DMSO were then added followed by 50 µL of McaPLGLDpaAR (8 µM, prepared by dilution of DMSO stock in assay butter). For each as say ten concentrations of test compound were examined in duplicate. Control wells lack either enzyme or test compound. The reactions were incubated at 37° C. for 2 hours. The fluorescence at 405 nm was measured immediately with an SLT Fluostar fluorometer (SLT Labinstruments GmbH, Grödig, Austria) using 320 nm excitation, without stopping the reaction.

The effect of the test compound was determined from the dose response curve generated by the 10 duplicate concentrations of inhibitor. The $IC_{50}$ (the concentration of compound required to give a 50% decrease in enzyme activity) was obtained by fitting data to the equation, $Y=a+((b-a)/(1+(c/X)^d))$. (Y=inhibition achieved for a particular dose; X=the dose in nM; a=minimum y or zero % inhibition; b=maximum y or 100% inhibition; c=is the $IC_{50}$; d=is the slope). The result was rounded to one significant figure.

MMP-12 Assay Protocol

Compounds of the invention were tested for inhibitory activity against metalloelastase (MMP-12) in an assay using a coumarin-labelled peptide substrate, (7-methoxycoumarin-4-yl)acetyl-Pro-Leu-Gly-Leu-(3-[2,4dinitrophenyl]-L-2,3-diaminopropionyl)-Ala-Arg-NH$_2$ (McaPLGLDpaAR) (Knight et al, 1992, above). The protocol for this assay was as described for the MMP-9 assay above.

MMP-1 Assay Protocol

Compounds of the invention were tested for inhibitory activity against collagenase (MMP-1) in an assay using a coumarin-labelled peptide substrate, (7-methoxycoumarin-4-yl)acetyl-Pro-Leu-Gly-Leu-(3-[2,4-dinitrophenyl]-L-2, 3diaminopropionyl)-Ala-Arg-NH2 (Mca PLGLDpaAR) (Knight et al, 1992, above). The protocol for this assay was as described for the MMP-9 assay above.

MMP-14 Assay Protocol

Compounds of the invention were tested for inhibitory activity against collagenase (MMP-14) in an assay using a coumarin-labelled peptide substrate, (7-methoxycoumarin-4-yl)acetyl-Pro-Leu-Gly-Leu-(3-[2,4-dinitrophenyl]-L-2, 3diaminopropionyl)-Ala-Arg-NH2 (Mca PLGLDpaAR) (Knight et al, 1992, above). The protocol for this assay was as described for the MMP-9 assay above.

MMP-2 Assay Protocol

Compounds of the invention were tested for inhibitory activity against collagenase (MMP-2) in an assay using a coumarin-labelled peptide substrate, (7-methoxycoumarin-4-yl)acetyl-Pro-Leu-Gly-Leu-(3-[2,4-dinitrophenyl]-L-2, 3diaminopropionyl)-Ala-Arg-NH2 (Mca PLGLDpaAR) (Knight et al, 1992, above). The protocol for this assay was as described for the MMP-9 assay above.

The results are expressed in terms of $IC_{50}$ (the concentration of compound required to give a 50% decrease in enzyme activity) and are presented in Table 1 below.

TABLE 1

| | $IC_{50}$ on different MMPs: | | |
| --- | --- | --- | --- |
| Example | MMP-2 $IC_{50}$ (µM) | MMP-9 $IC_{50}$ (µM) | MMP-12 $IC_{50}$ (µM) |
| Example 1 | 2.1 | 1.7 | 1.1 |
| Example 2 | 0.095 | 0.15 | 0.13 |
| Example 4 | 0.64 | 0.78 | 0.64 |
| Example 5 | 0.85 | 1.5 | 0.98 |
| Example 7 | 0.79 | 1.1 | 0.61 |
| Example 8 | 0.05 | 0.041 | 0.05 |
| Example 10 | 1.6 | 1.8 | 0.95 |

TABLE 1-continued

IC$_{50}$ on different MMPs:

| Example | MMP-2 IC$_{50}$ (µM) | MMP-9 IC$_{50}$ (µM) | MMP-12 IC$_{50}$ (µM) |
|---|---|---|---|
| Example 11 | 0.37 | 0.87 | 0.08 |
| Example 12 | 1.7 | 1.6 | 1.2 |
| Example 14 | 1.2 | 1.5 | 0.93 |
| Example 16 | 0.32 | 0.43 | 0.34 |
| Example 18 | 0.49 | 0.68 | 0.40 |

Example 21

IL-2-Induced Peritoneal Recruitment of Lymphocytes

Administration of IL-2 intraperitoneally causes migration of lymphocytes into the intraperitoneal cavity. This is a model for the cellular migration that occurs during inflammation.
Protocol C3H/HEN mice (Elevage Janvier, France) were intraperitoneally injected with IL-2 (Serono Pharmaceutical Research Institute, 20 µg/kg, in saline).

Compounds of the invention were suspended in 0.5% carboxymethylcellulose (CMC)/0.25% tween-20 and were administered by s.c. or p.o. route (10 ml/kg) 15 min prior to administration of IL-2.

Twenty-four hours after administration of IL-2, peritoneal white blood cells were collected by 3 successive lavages of the peritoneal cavity with 5 ml phosphate buffered saline (PBS)-1 mM EDTA (+4° C.). The suspension was centrifuged (1700 g×10 min at +4° C.). The resulting pellet was suspended in 1 ml PBS-1 mM EDTA.

Lymphocytes were identified and counted using a Beckman/Coulter counter.
Experimental Design The animals were divided into 6 groups (6 mice each group):

Group 1: (baseline) received 0.5% CMC/0.25% tween-20 (vehicle of compound of the invention) and saline (vehicle of IL-2);

Group 2: (control IL-2) received 0.5% CMC/0.25% tween-20 and injection of IL-2;

Group 3: Experimental group (Compound of the invention Dose 1) received a compound of the invention and injection of IL-2;

Group 4: Experimental group (Compound of the invention Dose 2) received a compound of the invention and injection of IL-2;

Group 5: Experimental group (Compound of the invention Dose 3) received a compound of the invention and injection of IL-2;

Group 6: Reference group received reference compound dexamethasone and injection of IL-2.
Calculation Inhibition of lymphocyte recruitment was calculated as follows:

$$\% \text{ inhibition} = \frac{1 - (LyX - Ly1)}{(Ly2 - Ly1)} \times 100\%$$

Where Ly 1=Number of lymphocytes in group 1 (E3/µl), Ly 2=Number of lymphocytes in group 2 (E3/µl), Ly X=Number of lymphocytes in group X (3-5) (E3/µl). The results are presented in Table 2 below.

TABLE 2

Percentage of inhibition of IL-2-induced peritoneal recruitment of lymphocytes by compounds of the invention:

| Example | Dose range or doses (mg/kg) | Route | % inhibition |
|---|---|---|---|
| Example 8 | 3 | Subcutaneous | 33 |
| Example 11 | 10 | Subcutaneous | 38 |

Example 22

CCl$_4$-Induced Liver Fibrosis Model

Carbon tetrachloride (CCl$_4$) induces liver fibrosis when administered intraperitoneally (Bulbena O, Culat J, Bravo M L., *Inflammation* 1997 Oct.; 21(5):475-88). Compounds of the invention can be evaluated for their ability to prevent the CCl$_4$-induced formation of fibrotic tissue.
Animals Male Sprague-Dawley rats, 7 weeks old, weight approx. 300 g from Charles River/Iffa-Crédo, St-Germain/l'Arbresle, France.

Rats are acclimatised for 5 days before commencing experiments, in air-conditioned rooms, 2 animals per cage, Temperature: 22° C.±2, Relative humidity: 55%±10 Light: 12 hour cycle (7 a.m.-7 p.m.), Cage: Makrolon® cage 42.5× 26.6×15 on each fitted with a stainless steel cover-feed rack.

The study involves the following groups of 8 animals each, as indicated below.

Group 1: "Sham" animals receive CCl$_4$ vehicle (i.p.) and once daily, the vehicle of test substance (s.c.)

Group 2: Positive control group receives CCl$_4$ (i.p.), and once daily, the vehicle of the test substance (s.c.)

Group 3: Experimental group receives CCl$_4$ (i.p.), and once daily, 2 mg/kg s.c. of compound according to the invention.

Group 4: Experimental group receives CCl$_4$ (i.p.), and once daily, 10 mg/kg s.c. of the compound according to the invention.

Group 5: Experimental group receives CCl$_4$ (i.p.) and once daily, 20 mg/kg s.c. of the compound according to the invention.

Rats were labeled on their tails. The labels are checked and renewed, if necessary, after every CCl$_4$ injection.
Procedure CCl$_4$ (Prolabo) in olive oil is administered every 3 days for three weeks by intra-peritoneal injection (0.25 ml CCl$_4$/kg body weight, diluted in oil 1:1 vol:vol for a total volume of 0.5 ml/kg). Animals are weighed daily. If body weight decreased by more than 10% of the initial weight, the animal was excluded from the study.

Vehicles and compound are used as follows:

CCl$_4$ was administered in olive oil (Prolabo) at a 1:1 dilution;

The compound of the invention is suspended in 0.25% Tween-80 and 0.25% carboxymethylcellulose in sterile 0.9% NaCl. The solution is kept at 4° C. throughout the experiment and used each day to prepare the suspensions.

The compound of the invention is administered daily by subcutaneous (s.c.) injection at a volume of administration of 5 ml/kg. Groups 1 and 2 are dosed s.c. with 5 ml/kg of vehicle. Freshly prepared solutions are used on each day of the experiment. Administrations are carried out each day at the same time.

The treatment of groups of this study is started for each animal at the time of the first CCl$_4$ administration and is continued for 21 consecutive days. The last administration of test substances or vehicle is done 1 day before the sacrifice of the animals.
Results Death are reported, date and supposed cause are reported.
Serum Enzyme Levels Animals are killed 21 days following the first CCl$_4$ administration by isofurane inhalation. Blood is withdrawn individually at the time of sacrifice, i.e. one day after the last administration of test substance or vehicle. Blood is centrifuged at 4° C. Plasma is carefully collected and aliquoted in 3 fractions. Plasma aspartate amino transferase (ASAT) and alanine amino transferase (ALAT) levels are measured in order to assess liver necrosis. Increased ASAT and ALAT levels in serum are associated with liver impairment. Average ASAT and ALAT levels for control animals and those treated with the compound of the invention at three different dosages are reported.
Histological Evaluation of Liver Fibrosis Liver fibrosis is evaluated by measuring the area of fibrosis in the liver using microchotomy. Results are reported as percentage area that is fibrotic.

The liver is removed, the three lobes are dissected and samples are removed and either fixed in 10% formaldehyde or frozen at −80° C.

Liver sections are embedded in paraffin blocks. Sectioning and staining with Sirius red are performed. Quantification of the fibrosis in liver is carried out on a minimum of 3 sections taken from different locations in the liver. The quantitative analysis is performed using an image analyser (Imstar) and the software Morphostar.

Average area percentages of fibrosis in the livers of animals in the different groups are calculated.

Example 23

Chronic Obstructive Pulmonary Disease (COPD) Model

Compounds of the invention can be evaluated for their ability to prevent cigarette smoke-induced COPD.

Female AJ mice (Harlan, 17-25 g) are exposed daily to cigarette smoke (CS) for 11 consecutive days in groups of 5, in individual clear chambers. Animals are weighed prior to treatment, on day 6 of exposure and on day 12. The CS was generated using 1R1 cigarettes purchased from the Institute of Tobacco Research, University of Kentucky, USA and is allowed to enter the chambers at a flow rate of 100 ml/min.

In order to minimise any potential problems caused by repeated exposure to a high level of daily CS, the exposure of the mice to TS is increased gradually over the time to a maximum of 6 cigarettes from day 5 to day 11 (approximately 48 min exposure).

A sham group of mice is also exposed to air on a daily basis for equivalent lengths of time as controls (no CS exposure).
Treatment Compounds of the invention are prepared in 0.5% carboxymethylcellulose Na salt (CMC, Sigma reference C-4888) as vehicle.

Animals are orally dosed twice daily by gavage in a dose volume of 5 ml/kg, 1 h prior to air or CS exposure and 6 h after the cessation of the exposure.

Sham animals (n=10) received vehicle and are exposed to air for up to a maximum of 50 minutes per day. The control group (n=10) received vehicle and is exposed to CS (up to a maximum of 6 cigarettes per day). Additional groups are exposed to CS (from up to a maximum of 6 cigarettes per day) and treated with one of the test compounds or the reference compound.
Bronchoalveolar Lavage and Cytospin Analysis Twenty four hours after the last CS exposure, bronchoalveolar lavage is performed as follows:

The trachea is dissected under deep anesthesia (sodium pentobarbitone) and cannulated using a Portex nylon intravenous cannula shortened to approximately 8 mm. Phosphate buffered saline (PBS, Gibco) containing 10 units/ml heparin (0.4 ml) is gently instilled and withdrawn 3 times. The lavage fluid is placed in an Eppendorf tube and kept on ice prior to subsequent determinations. Then, lavage fluid is separated from cells by centrifugation. The supernatant is removed and frozen for subsequent analysis. The cell pellet is resuspended in PBS and total cell numbers were calculated by counting a stained aliquot (Turks stain) under a microscope using a haemocytometer.

Differential cell count is then performed as follows: The residual cell pellet is diluted to approximately 105 cells per ml. A volume of 500 µl is placed in the funnel of a cytospin slide and was centrifuged for 8 min at 800 rpm. The slide is air-dried and stained using 'Kwik-Diff' solutions (Shandon) following purchaser instructions. Slides are dried and coverslipped and differential cell count is done using light microscopy. Up to 400 cells are counted for each slide. Cells were differentiated using standard morphometric techniques.
Statistical Analysis The mean +/−S.D. is calculated for each experimental group.

Results are analyzed using a one-way analysis of variance (ANOVA), followed by a Bonferroni correction for multiple comparisons. Statistical significance is considered with $p<0.05$.

Example 24

Preparation of a Pharmaceutical Formulation

The following formulation examples illustrate representative pharmaceutical compositions according to the present invention being not restricted thereto.
Formulation 1—Tablets A compound of Formula (I) is admixed as a dry powder with a dry gelatin binder in an approximate 1:2 weight ration. A minor amount of magnesium stearate is added as a lubricant. The mixture is formed into 240-270 mg tablets (80-90 mg) of active octahydropyrrolo[2,3,c]pyridine derivative per tablet) in a tablet press.
Formulation 2—Capsules A compound of Formula (I) is admixed as a dry powder with a starch diluent in an approximate 1:1 weight ratio. The mixture is filled into 250 mg capsules (125 mg of active octahydropyrrolo[2,3,c]pyridine derivative per capsule).
Formulation 3—Liquid A compound of Formula (I) (1250 mg), sucrose (1.75 g) and xanthan gum (4 mg) are blended, passed through a No. 10 mesh U.S. sieve, and then mixed with a previously prepared solution of microcrystalline cellulose and sodium carboxymethyl cellulose (11:89, 50 mg) in water. Sodium benzoate (10 mg), flavor, and color are diluted with water and added with stirring. Sufficient water is then added to produce a total volume of 5 mL.
Formulation 4—Tablets A compound of Formula (I) is admixed as a dry powder with a dry gelatin binder in an approximate 1:2 weight ratio.

A minor amount of magnesium stearate is added as a lubricant. The mixture is formed into 450-900 mg tablets (150-300 mg of active octahydropyrrolo[2,3,c]pyridine derivative) in a tablet press.

Formulation 5—Injection

A compound of Formula (I) is dissolved in a buffered sterile saline injectable aqueous medium to a concentration of approximately 5 mg/ml.

The invention claimed is:

1. An octahydropyrrolo[2,3,c]pyridine compound according to Formula (I)

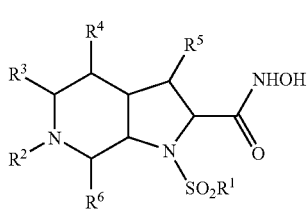

wherein:

$R^1$ is selected from the group consisting of
an aryl group,
an aryl group having at least one substituent,
a $C_3$-$C_8$-cycloalkyl group, and
a $C_3$-$C_8$ cycloalkyl group having at least one substituent, $R^2$ is selected from the group consisting of
hydrogen,
a $C_1$-$C_6$ alkyl group,
a $C_1$-$C_6$ alkyl group having at least one substituent,
a $C_2$-$C_6$ alkenyl group,
a $C_2$-$C_6$ alkenyl group having at least one substituent,
a $C_2$-$C_6$ alkynyl group,
a $C_2$-$C_6$ alkynyl group having at least one substituent,
an acyl group represented by —C(O)R where R is selected from the group consisting of a $C_1$-$C_{12}$-alkyl group, an aryl group, a heteroaryl group, a $C_3$-$C_8$-cycloalkyl group, a heterocycloalkyl group, and a $C_1$-$C_6$-alkyl group substituted with at least one of an aryl group, a heteroaryl group, a $C_3$-$C_8$-cycloalkyl group, and a heterocycloalkyl group,
an acyl group represented by —C(O)R where R is defined above and having at least one substituent,
an aminocarbonyl group,
an aminocarbonyl group having at least one substituent,
an alkoxycarbonyl group,
an alkoxycarbonyl group having at least one substituent,
a sulfonyl group, and
a sulfonyl group having at least one substituent;
each of $R^3$, $R^4$, $R^5$ and $R^6$ is independently selected from the group consisting of
hydrogen,
a halogen,
a $C_1$-$C_6$ alkyl group, and
a $C_1$-$C_6$ alkyl group having at least one substituent;
and wherein said substituent is selected from the group consisting of a $C_1$-$C_6$-alkyl group, a $C_2$-$C_6$ alkenyl group, a $C_2$-$C_6$ alkynyl group, a cycloalkyl group, a heterocycloalkyl group, a $C_1$-$C_6$-alkyl group substituted with an aryl group, a $C_1$-$C_6$-alkyl group substituted with a heteroaryl group, a $C_1$-$C_6$-alkyl group substituted with a cycloalkyl group, a $C_1$-$C_6$-alkyl group substituted with a heterocycloalkyl group, an amino group, an ammonium group, an acyl group, an acyloxy group, an acylamino group, an aminocarbonyl group, an alkoxycarbonyl group, a ureido group, an aryl group, a carbamate, a heteroaryl group, a sulfinyl group, a sulfonyl group, an alkoxy group, a sulfanyl group, a halogen, a carboxy group, a trihalomethyl group, a cyano group, a hydroxy group, a mercapto group, and a nitro group;

or a pharmaceutically acceptable salt thereof.

2. The octahydropyrrolo[2,3,c]pyridine compound according to claim 1, wherein $R^1$ is aryl.

3. The octahydropyrrolo[2,3,c]pyridine compound according to claim 1, wherein $R^1$ is phenyl.

4. The octahydropyrrolo[2,3,c]pyridine compound according to claim 1, wherein $R^2$ is selected from the group consisting of hydrogen,
—(CH$_2$)$_n$C(O)—(CH$_2$)$_m$—R$^8$ as the acyl group,
—(CH$_2$)$_n$C(O)NR$^8$R$^9$ as the aminocarbonyl group,
—C(O)—O—R$^{10}$ as the alkoxycarbonyl group, and
—SO$_2$—R$^{15}$ as the sulfonyl group;

each of $R^8$ and $R^9$ is independently selected from the group consisting of hydrogen, a $C_1$-$C_{12}$ alkyl group, a $C_2$-$C_6$ alkenyl group, a $C_2$-$C_6$ alkynyl group, an aryl group, a heteroaryl group, a $C_3$-$C_8$-cycloalkyl group and a heterocycloalkyl group;

$R^{10}$ is selected from the group consisting of a $C_1$-$C_6$ alkyl group, a $C_2$-$C_6$ alkenyl group, a $C_2$-$C_6$ alkynyl group, an aryl group, a heteroaryl group, a heteroalkyl group, a $C_3$-$C_8$-cycloalkyl group and a heterocycloalkyl group;

$R^{15}$ is selected from the group consisting of a $C_1$-$C_{12}$ alkyl group, a $C_2$-$C_6$ alkenyl group, a $C_2$-$C_6$ alkynyl group, an aryl group, a heteroaryl group, a $C_3$-$C_8$-cycloalkyl group and a heterocycloalkyl group; and each of m and n is independently 0, 1 or 2.

5. The octahydropyrrolo[2,3,c]pyridine compound according to claim 1, wherein each of $R^3$, $R^4$, $R^5$ and $R^6$ is hydrogen.

6. The octahydropyrrolo[2,3,c]pyridine compound according to claim 1, wherein $R^1$ is substituted phenyl;
$R^2$ is selected from the group consisting of hydrogen,
—(CH$_2$)$_n$C(O)—(CH$_2$)$_m$—R$^8$ as the acyl group,
—(CH$_2$)$_n$C(O)NR$^8$R$^9$ as the aminocarbonyl group,
—C(O)—O—R$^{10}$ as the alkoxycarbonyl group, and
—SO$_2$—R$^{15}$ as the sulfonyl group;

$R^8$ is selected from the group consisting of a $C_1$-$C_{10}$ alkyl group, a $C_2$-$C_6$ alkenyl group, a $C_2$-$C_6$ alkynyl group, an aryl group, a heteroaryl group, a $C_3$-$C_8$-cycloalkyl group and a heterocycloalkyl group;

$R^9$ is hydrogen;

$R^{10}$ is selected from the group consisting of a $C_1$-$C_6$ alkyl group, a $C_2$-$C_6$ alkenyl group, a $C_2$-$C_6$ alkynyl group, an aryl group, a heteroaryl group, a $C_3$-$C_8$-cycloalkyl group and a heterocycloalkyl group;

each of $R^3$, $R^4$, $R^5$ and $R^6$ is hydrogen;

m is 0, 1 or 2; and n is 0 or 1.

7. The octahydropyrrolo[2,3,c]pyridine compound according to claim 1, wherein $R^1$ is substituted phenyl;
$R^2$ is —SO$_2$—R$^{15}$;
$R^{15}$ is selected from the group consisting of a $C_1$-$C_6$ alkyl group, an aryl group, a heteroaryl group, a $C_3$-$C_8$-cycloalkyl group and a heterocycloalkyl group; and each of $R^3$, $R^4$, $R^5$ and $R^6$ is hydrogen.

8. The octahydropyrrolo[2,3,c]pyridine compound according to claim 1, wherein $R^1$ is substituted phenyl;
$R^2$ is selected from the group consisting of hydrogen,
—(CH$_2$)$_n$C(O)—(CH$_2$)$_m$—R$^8$ as the acyl group,
—(CH$_2$)$_n$C(O)NR$^8$R$^9$ as the aminocarbonyl group, —C(O)—O—$R^{10}$ as the alkoxycarbonyl group, and —$SO_2$—$R^{15}$ as the sulfonyl group;

$R^8$ is selected from the group consisting of a $C_1$-$C_6$ alkyl group, a $C_2$-$C_6$ alkenyl group, a $C_2$-$C_6$ alkynyl group, an aryl group, a heteroaryl group, a $C_3$-$C_8$-cycloalkyl group and a heterocycloalkyl group;

each of $R^3$, $R^4$, $R^5$ and $R^6$ is hydrogen;

$R^{10}$ is selected from the group consisting of a $C_1$-$C_6$ alkyl group, a $C_2$-$C_6$ alkenyl group, a $C_2$-$C_6$ alkynyl group, an aryl group, a heteroaryl group, a heteroalkyl group, a $C_3$-$C_8$-cycloalkyl group and a heterocycloalkyl group;

m is 0, 1 or 2; and n is 0 or 1.

9. The octahydropyrrolo[2,3,c]pyridine compound according to claim 1, selected from the group consisting of:

rel-(2S,3aS,7aR)-6-benzoyl-N-hydroxy-1-[(4-methoxyphenyl)sulfonyl]octahydro-1H pyrrolo[2,3-c]pyridine-2-carboxamide;

rel-(2S,3aS,7aR)-6-acetyl-N-hydroxy-1-[(4-methoxyphenyl)sulfonyl]octahydro-1H-pyrrolo[2,3-c]pyridine-2-carboxamide;

rel-(2S,3aS,7aR)—N-hydroxy-1-[(4-methoxyphenyl)sulfonyl]-6-(3-methylbutanoyl) octahydro-1H-pyrrolo[2,3-c]pyridine-2-carboxamide;

rel-(2S,3aS,7aR)-6-(3-cyclopentylpropanoyl)-N-hydroxy-1-[(4-methoxyphenyl) sulfonyl]octahydro-1H-pyrrolo[2,3-c]pyridine-2-carboxamide;

2-methoxyethyl rel-(2S,3aS,7aR)-2-[(hydroxyamino)carbonyl]-1-[(4-methoxyphenyl) sulfonyl]octahydro-6H-pyrrolo[2,3-c]pyridine-6-carboxylate;

rel-(2S,3aS,7aR)-6-dodecanoyl-N-hydroxy-1-[(4-methoxyphenyl)sulfonyl]octahydro-1H-pyrrolo[2,3-c]pyridine-2-carboxamide;

rel-(2S,3aS,7aR)-6-(cyclopentylcarbonyl)-N-hydroxy-1-[(4-methoxyphenyl) sulfonyl]octahydro-1H-pyrrolo[2,3-c]pyridine-2-carboxamide;

rel-(2S,3aS,7aR)—N-hydroxy-1-[(4-methoxyphenyl)sulfonyl]-6-(3-phenylpropanoyl) octahydro-1H-pyrrolo[2,3-c]pyridine-2-carboxamide;

rel-(2S,3aS,7aR)—N-hydroxy-1-[(4-methoxyphenyl)sulfonyl]-6-(methylsulfonyl) octahydro-1H-pyrrolo[2,3-c]pyridine-2-carboxamide;

rel-(2S,3aS,7aR)—N-hydroxy-1,6-bis[(4-methoxyphenyl)sulfonyl]octahydro-1H-pyrrolo[2,3-c]pyridine-2-carboxamide;

rel-(2S,3aS,7aR)-6-(biphenyl-4-ylcarbonyl)-N-hydroxy-1-[(4-methoxyphenyl) sulfonyl]octahydro-1H-pyrrolo[2,3-c]pyridine-2-carboxamide;

rel-(2S,3aS,7aR)-6-(biphenyl-4-ylsulfonyl)-N-hydroxy-1-[(4-methoxyphenyl) sulfonyl]octahydro-1H-pyrrolo[2,3-c]pyridine-2-carboxamide;

rel-(2S,3aS,7aR)-6-[2-(diethylamino)-2-oxoethyl]-N-hydroxy-1-[(4-methoxyphenyl) sulfonyl]octahydro-1H-pyrrolo[2,3-c]pyridine-2-carboxamide;

rel-(2S,3aS,7aR)-6-[2-(ethylamino)-2-oxoethyl]-N-hydroxy-1-[(4-methoxyphenyl) sulfonyl]octahydro-1H-pyrrolo[2,3-c]pyridine-2-carboxamide;

rel-(2S,3aS,7aR)—N2-hydroxy-1-[(4-methoxyphenyl) sulfonyl]-N6-phenyloctahydro-6H-pyrrolo[2,3-c]pyridine-2,6-dicarboxamide;

rel-(2S,3aS,7aR)—N-hydroxy-1-[(4-methoxyphenyl)sulfonyl]octahydro-1H-pyrrolo[2,3-c]pyridine-2-carboxamide; and benzyl rel-(2S,3aS,7aR)-2-[(hydroxyamino)carbonyl]-1-[(4-methoxyphenyl) sulfonyl]octahydro-6H-pyrrolo[2,3-c]pyridine-6-carboxylate.

10. A pharmaceutical composition comprising one or more octahydropyrrolo[2,3,c]pyridine compounds according to claim 1 and a pharmaceutically acceptable carrier, diluent or excipient therefor.

\* \* \* \* \*